(12) United States Patent
Mir

(10) Patent No.: US 11,066,701 B2
(45) Date of Patent: Jul. 20, 2021

(54) SUPER-RESOLUTION SEQUENCING

(71) Applicant: Kalim U. Mir, Cambridge, MA (US)

(72) Inventor: Kalim U. Mir, Cambridge, MA (US)

( * ) Notice: Subject to any disclaimer, the term of this patent is extended or adjusted under 35 U.S.C. 154(b) by 176 days.

(21) Appl. No.: 15/983,843

(22) Filed: May 18, 2018

(65) Prior Publication Data

US 2018/0327829 A1 Nov. 15, 2018

Related U.S. Application Data

(63) Continuation-in-part of application No. PCT/US2016/062813, filed on Nov. 18, 2016.

(60) Provisional application No. 62/256,981, filed on Nov. 18, 2015.

(51) Int. Cl.
*C12Q 1/6869* (2018.01)
*C12Q 1/6874* (2018.01)

(52) U.S. Cl.
CPC ......... *C12Q 1/6869* (2013.01); *C12Q 1/6874* (2013.01)

(58) Field of Classification Search
None
See application file for complete search history.

(56) References Cited

U.S. PATENT DOCUMENTS

2013/0085073 A1* 4/2013 Meuleman et al. . C12Q 1/6874
506/2
2014/0162892 A1* 6/2014 Mir ..................... C12Q 1/6874
506/9

OTHER PUBLICATIONS

Beater et al., "Simple and aberration-free 4color-STED-multiplexing by transient binding," Opt. Express 2015, 23(7):8630-8638, published Mar. 27, 2015. (Year: 2015).*

* cited by examiner

*Primary Examiner* — Kaijiang Zhang
(74) *Attorney, Agent, or Firm* — Morgan, Lewis & Bockius LLP

(57) ABSTRACT

A method for template-directed sequencing-by-synthesis of an array of target polynucleotide can include:
(a) providing an array of target polynucleotides in a fluidic vessel;
(b) contacting the array of polynucleotides with a solution comprising (i) polymerization complex and (ii) reversibly terminating and differently labeled A,C,G, and T/U nucleotides;
(c) incorporating one of the differently labeled nucleotides, using the polymerization complex, into a chain complementary to at least one of the array of polynucleotides;
(d) binding imaging tags to the differently labeled nucleotides of step (c);
(e) imaging and storing the identity and position of the imaging tags of step (d);
(f) reversing termination (b)-(e);
(g) repeating steps (b)-(e) and assembling a sequence for each of the array of target polynucleotides from the stored identity and position of the imaging tags, optionally as a homogeneous or one pot reaction. Additional methods of sequencing target polynucleotides are described herein.

17 Claims, 23 Drawing Sheets
Specification includes a Sequence Listing.

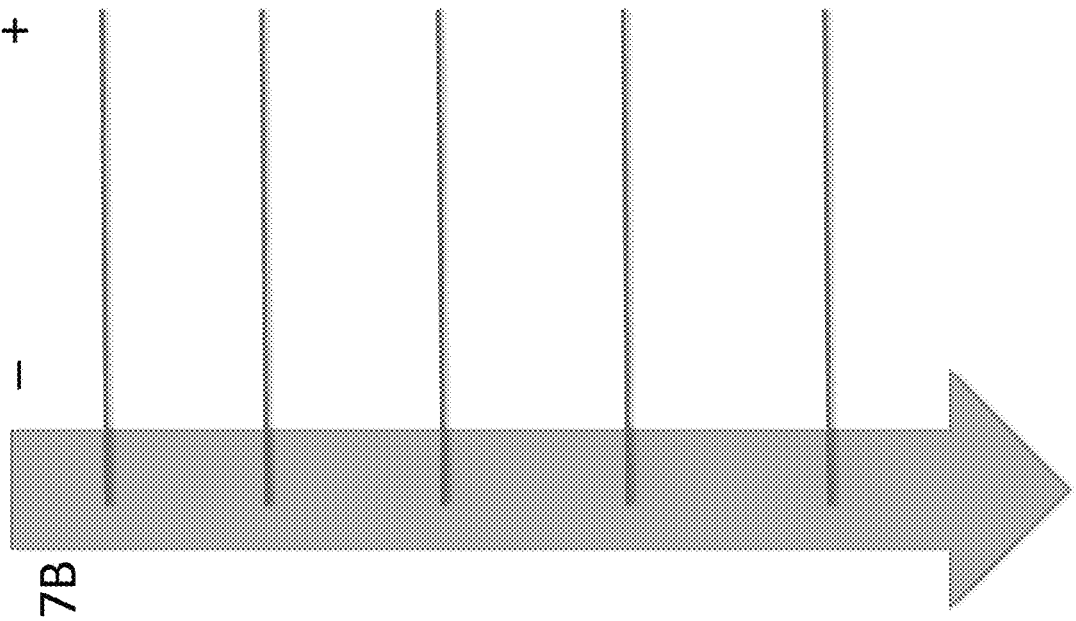
FIG. 7B Reagent Flow Voltage On
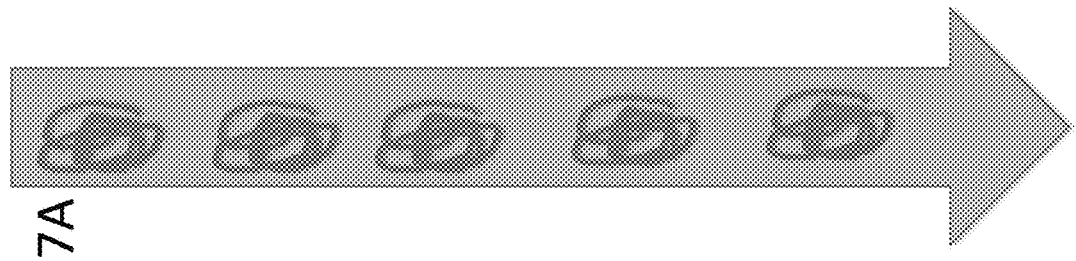
FIG. 7A Reagent Flow Voltage Off — YOYO-1 emission
— Cy3 absorption
— Texas Red absorption
— Atto674N absorption
— Alexa 700 absorption

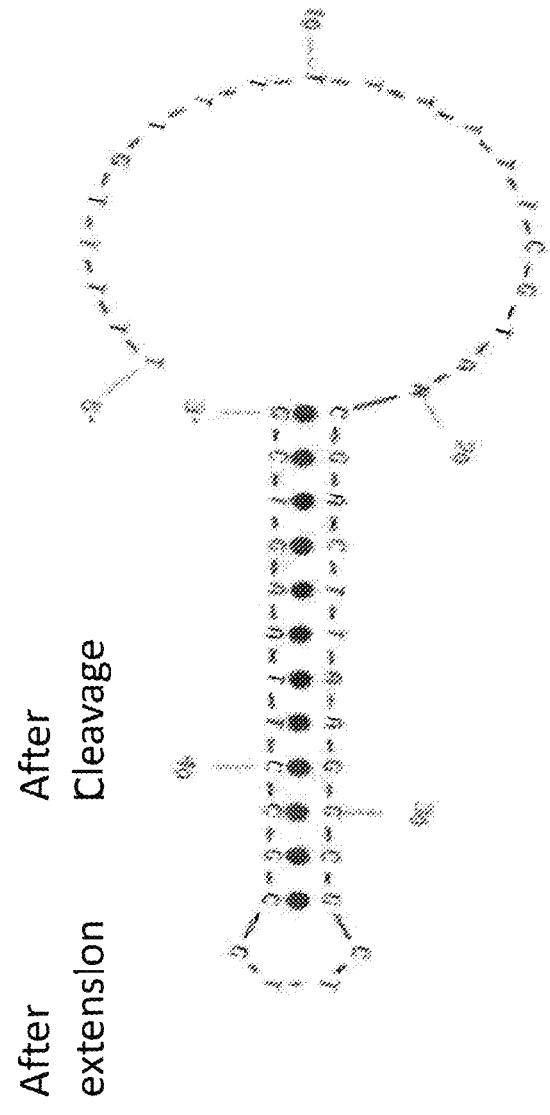
FIG. 14

R is a reversible terminator
L is a label attached at the the terminal phosphate of the nucleotide
The label is part of the natural leaving group

FIG. 21

DOCKING SITES

Partner 1a Nuc–TTATACATCTA-3' (SEQ ID NO:9)
Partner 1b Nuc–TTATCTACATA-3' (SEQ ID NO:11)
Partner 1c Nuc–TTTCTTCATTA-3' (SEQ ID NO:12)
Partner 1d Nuc–TTATGAATCTA-3' (SEQ ID NO:13)
Partner 1e Nuc–TTTTAGGTAAA-3' (SEQ ID NO:14)
Partner 1f Nuc–TTAATTGAGTA-3' (SEQ ID NO:15)
Partner 1g Nuc–TTAATTAGGAT-3' (SEQ ID NO:16)
Partner 1h Nuc–TTATAATGGAT-3' (SEQ ID NO:17)
Partner 1i Nuc–TTTAATAAGGT-3' (SEQ ID NO:18)
Partner 1j Nuc–TTATAGAGAAG-3' (SEQ ID NO:19)
Partner 1k Nuc–TTTTGATGATA-3' (SEQ ID NO:20)
Partner 1l Nuc–TTATAGTGATT-3' (SEQ ID NO:21)

IMAGERS

Partner 2a 5'–CTAGATGTAT-dye (SEQ ID NO:22)
Partner 2b 5'–TATGTAGATC-dye (SEQ ID NO:23)
Partner 2c 5'–GTAATGAAGA-dye (SEQ ID NO:24)
Partner 2d 5'–GTAGATTCAT-dye (SEQ ID NO:25)
Partner 2e 5'–CTTTACCTAA-dye (SEQ ID NO:26)
Partner 2f 5'–GTACTCAATT-dye (SEQ ID NO:27)
Partner 2g 5'–CATCCTAATT-dye (SEQ ID NO:28)
Partner 2h 5'–GATCCATTAT-dye (SEQ ID NO:29)
Partner 2i 5'–CACCTTATTA-dye (SEQ ID NO:30)
Partner 2j 5'–CCTTCTCTAT-dye (SEQ ID NO:31)
Partner 2k 5'–GTATCATCAA-dye (SEQ ID NO:32)
Partner 2l 5'–GAATCACTAT-dye (SEQ ID NO:33)

SUPER-RESOLUTION SEQUENCING

SEQUENCE LISTING SUBMISSION VIA EFS-WEB

A computer readable text file, entitled "SequenceListing.txt," created on or about May 18, 2018 with a file size of about 8 kb contains the sequence listing for this application and is hereby incorporated by reference in its entirety.

FIELD OF THE INVENTION

In various aspects and embodiments the present invention relates to methods of sequencing target polynucleotides.

BACKGROUND

Initially there were two successful approaches to DNA sequence determination: the dideoxy chain termination method, (Sanger et al, Proc. Natl. Acad. Sci., 74:5463-5467 (1977)) and the chemical degradation method (Maxam et al, Proc. Natl. Acad. Sci., 74:560-564 (1977)). These methods of sequencing nucleotides were both time consuming and expensive. The need for large-scale sequencing of individual human genomes, the genomes of other organisms and pathogens required lower-cost and more rapid alternatives to be developed.

This led to the advent of Sequencing by Synthesis (SbS) which has become the dominant next generation sequencing (NGS) technology (e.g. U.S. Pat. No. 5,302,509) and involves the identification of each nucleotide during or following its template-directed incorporation by a polymerase into an extending DNA strand. In one SbS approach, pyrosequencing (Ronaghi et al Science vol. 281, no. 5375 (1998)), the detection is bioluminescent based on pyrophosphate (PPi) release, its conversion to ATP, and the production of visible light by firefly luciferase. Thermo Fisher's Ion Torrent platform conducts sequencing in the same way but detects the liberation of a proton rather than PPi. These SbS methods add only one of the four nucleotides ACGT at a time and struggle to determine the numbers of bases when there is a homopolymer run in the target. Also as the signal is diffusible, such methods are limited in their throughput. A massive degree of parallelism becomes available when surface immobilized reactions are analysed in a range of other next generation sequencing methods. Moreover adding four nucleotides simultaneously and distinguishing them by labeling one or more of those nucleotides with different dyes is preferable and is part of the methods developed by Illumina Inc. and Pacific Biosciences Inc. In Illumina sequencing chain extension is controlled nucleotide by nucleotide using reversible terminators. U.S. Pat. No. 5,302,509 and Metzker et al (1994) disclose SbS strategies, which involve repetitive base addition cycles and use reversible terminators to prevent the addition of more than one base at a time. Illumina's nucleotides are double modified (Bentley et al Nature 456, 53-59 (2008)) so that there is a label on the base (which is cleavable) and a blocking group or terminator at the 3' end, which prevents the addition of further nucleotides. Once the incorporated nucleotide has been identified the terminator is removed to allow the next nucleotide to be incorporated. Mir et al (Nucl. Acids Res. (2009) 37 (1): e5.) describe a ligation based sequencing by synthesis approach and such a kind of approach is used in Applied Biosystem's SOLID sequencing technology. Illumina's SbS is conducted on clonal amplicon clusters and because it is difficult to get the reaction to go to completion the state of progress of different molecules of the population can become out of phase. At any given cycle one molecule in the population may be adding a different base compared to other molecule which leads to degradation of signal from each cluster. The number of molecules that have dropped out of synchrony (e.g., missed addition/removal) will increase in the population as the synthesis progresses, and very quickly molecules that are out of synch, out-number those that remain in synchrony. Because of this asynchronous noise—e.g., a mixture of signals from different bases—the sequence signal is obscured and cannot continue to be obtained without high error. However this problem is avoided when individual molecules rather than molecular ensembles are sequenced as described by Ely Michael Rabani in 1996 (WO1996027025A1), previously developed by Helicos Bio. Such sequencing on individual molecule makes sample preparation simpler (Helicos) and enables longer read lengths to be obtained (Pacific Biosciences).

A problem with Illumina's implementation of a reversible terminator approach is that several reagent exchange steps need to be made over clusters of target polynucleotides that are immobilized in a flow cell. The reagents reside outside the flow cell are delivered into the flow cell using a syringe pump at each step of the sequencing cycle and several wash steps are needed in between the functional steps of the sequencing cycle. This means that a large volume of reagents is consumed in a sequencing run which, the sequencing instrument has to be large enough to accommodate. As reagents are provided in excess, a large amount of costly reagent is wasted in the sequencing run. By contrast, Pacific Biosciences do not use a reversible terminator approach. The chain extension is viewed on individual target molecules near to real-time by attaching the label on a terminal phosphate, a natural leaving group of the incorporation reaction. The advantage of this is that reagents needed for sequencing can be loaded at the start of the reaction without further reagent exchange. However, this is at the cost of not being able to stop the reaction to definitively determine which base has been incorporated and consequently the error rate is high. Also there is light-induced damage to the complex due to the reaction having to be continuously illuminated and the method is low-throughput because only one field of view can be sequenced at a time using a single detector; the cost of increasing the number of detectors is prohibitive. Genia (acquired by Roche) sequencing purports to use PacBio-like chemistry with nanopore detectors but the throughput and error issues may well remain (Kumar, Fuller et al). One ambitious approach that does not use SbS is nanopore sequencing introduced by Oxford Nanopore Technology. However, so far the footprint of the nanopore detection is too large to achieve the required single base resolution; error rate is high and throughput is low.

In molecular assays field those that are one-pot on homogeneous have advantages because no fluid exchange or wash steps are needed. In imaging, the 2014 Nobel Prize for chemistry was awarded for super-resolution (superresolution) methods that allow imaging methods to go beyond the diffraction limit of light. These two approaches form the cornerstone of the inventions described in this invention.

SUMMARY OF THE INVENTION

The present invention provides sequencing methods that overcome the shortcomings of the methods disclosed in the prior art. The invention relates to SbS, which comprises a template-derived chain extension, where a sequencing cycle comprises determination of a single nucleotide in the growing chain. Each sequencing cycle comprises multiple steps and multiple sequencing cycles are conducted to sequence the template with the advantage that a massive number of templates can be sequenced in parallel within the same reaction volume. In general, the sequencing assumes that the target polynucleotide contains nucleotides that are complementary to the ones incorporated (a sequencing error is an example of a case where this assumption does not hold).

The method requires the target polynucleotide to act as a template for the template-derived chain extension, modified nucleotides, which are or can become detectably (e.g. fluorescently) labeled and a polymerization complex. In some embodiments the polymerization complex comprises a polymerizing agent such as a DNA Polymerase, and a 3'hydroxyl terminus e.g. from a primer annealed to a single-stranded target or a nick in one strand of a double stranded template. In this case the nucleotides are deoxyribonucleotides. In some embodiments the polymerization complex comprises a polymerizing agent such as a RNA Polymerase and a promoter sequence. In this case the nucleotides are ribonucleotides. In some embodiments the polymerization complex comprises a polymerizing agent such as a DNA ligase and a 3' hydroxy terminus or a 5'phosphate terminus. In this case the nucleotide is an oligonucleotide, optionally with a 5'phosphate depending on the 5' or 3' direction of chain extension. In some embodiments the method can be applied to bulk level sequencing as well as single molecule sequencing.

In certain embodiments SbS is monitored at the individual molecule level. In certain embodiments the single molecules are localized on a 2-D surface to high precision and this single molecule localization enables molecules that are normally too densely packed to be resolve by diffraction limited optics, to be "super-resolved". Hence, a much higher density of individually resolvable molecules can be sequenced in parallel compared to existing NGS methods. The fact that molecules are arrayed at high density means a much smaller footprint is required in the flow cell and much less reagent volume is required over the smaller reaction area. Because of this, a smaller amount of reagents need to be loaded onto the array and the area where the molecules are arrayed can be much smaller and the space needed to store reagents before and after they have passed over the dense lawn of templates is much smaller than non-super-resolution sequencing methods. Because the distances over which fluids will have to move are shorter than current flow cells, there will be some savings in time too. With this it will be possible to make a single, consumable fluidic device for sequencing in which all reagents and buffers are pre-loaded before the sequencing commences.

In some embodiments super-resolution methods require specific sets of compatible labeling methods to be used. In some embodiments the super-resolution method comprises Stimulated Emission and Depletion (STED) (ref). In some embodiments the super-resolution method comprises Stochastic Optical Reconstruction Microscopy (STORM) M. J. Rust, M. Bates, X. Zhuang Nature Methods 3: 793-795 (2006) and similar methods and variants thereof. In some embodiments the super-resolution method comprises: Points Accumultion in Imaging Topography (PAINT). In some embodiments the PAINT comprises a tag (or docking site) attached to the nucleotide and anti-tag (e.g. Imager) free in solution that binds to the tag (Sharonov, A. & Hochstrasser, R. M. Wide-field subdiffraction imaging by accumulated binding of diffusing probes. Proc. Natl. Acad. Sci. USA (PNAS) 103, 18911-18916 (2006). In some embodiments the PAINT comprises DNA PAINT (Jungmann, R. et al. Single-molecule kinetics and super-resolution microscopy by fluorescence imaging of transient binding on DNA origami. Nano Lett. 10, 4756-4761 (2010).)

Accordingly in some embodiments, the methods include the steps of:

(a) disposing the target polynucleotide within a fluidic vessel (b) contacting the target polynucleotide with a solution (reaction volume) comprising (i) polymerization complex and (ii) a set of modified nucleotides, (c) incorporating one of the modified nucleotides, using the polymerization complex, into a chain complementary to the target polynucleotide;

(d) detecting the signal for the type of nucleotide persistently proximal to the target polynucleotide sequence above or separate from signal for the type of nucleotides not persistently proximal to the target polynucleotide sequence using super-resolution detection and thereby identifying the type of the differently labeled nucleotide incorporated;

(e) cleaving the cleavable linker(s), thereby the label; and (f) repeating steps (b)-(e).

In some embodiments the sequencing of the target polynucleotide is conducted in a closed system with respect to solution exchange, in that after sample and reagent loading, the sequencing proceeds without exchange of reagents from outside the vessel, as has only to date been available for high-error real-time sequencing methods such as PacBio and ONT sequencing. However, in some embodiments of the present invention, in contrast to real-time sequencing, the incorporation of each labeled nucleotide into the growing chain is controlled one nucleotide at a time, so that sufficient time is available between successive nucleotide additions to determine the identity of the incorporated base and retain high accuracy within a closed system.

In some embodiments, the methods include the steps of:

(a) disposing the target polynucleotide within a fluidic vessel (b) contacting the target polynucleotide with a solution (reaction volume) comprising (i) polymerization complex and (ii) four types of differently labeled nucleotides, wherein each differently labeled nucleotide comprises the structure:

or

wherein N is a nucleotide, c is a cleavable linker, T is a terminator group chemically linked to N, and L is a label chemically linked to N, L(T) is a structure that acts as a label and a terminator wherein L is specific for A, C, G, T/U and c is a cleavable linker;

(c) incorporating one of the differently labeled nucleotides, using the polymerization complex, into a chain complementary to the target polynucleotide;

(d) detecting the signal for the type of nucleotide persistently proximal to the target polynucleotide sequence above signal for the type of nucleotides not persistently proximal to the target polynucleotide sequence and thereby identifying the type of the differently labeled nucleotide incorporated;

(e) cleaving the cleavable linker(s), thereby the label; and (f) repeating steps (b)-(e)

In some embodiments (b)-(e) is done without external reagent input into the vessel, thereby sequencing the target polynucleotide.

In several embodiments, the methods include the steps of:

(a) disposing the target polynucleotide within a fluidic vessel;

(b) contacting the target polynucleotide with a solution (reaction volume) comprising four types of differently labeled nucleotides, wherein each differently labeled nucleotide comprises the structure:

wherein N is a nucleotide, T is a terminator group chemically linked to N, and L is a label chemically linked to N and He is a cleavable linker that enables cleavage to be conducted homogeneously, without chemical reagent exchange from outside the vessel; providing one or more fluorescent label(s), said fluorescent label(s) attached to polymerizing reagent or incorporated into the target DNA polynucleotide;

(c) incorporating one of the differently labeled nucleotides, using the polymerase reagent, into a chain complementary to the target polynucleotide;

(d) providing a stimulus to initiate an energy transfer interaction and thereby identifying the type of the differently labeled nucleotide incorporated;

(e) providing a trigger to cleave the cleavable linker, thereby removing the cleavable terminator group and the cleavable label; and (f) repeating steps (b)-(e) as a homogeneous or one pot reaction, thereby sequencing the target polynucleotide (e.g., assuming that the target polynucleotide contains nucleotides that are complementary to the ones incorporated).

In some embodiments detection occurs when the nucleotide added is incorporated. In other embodiments detection occurs when the nucleotide added is bound to the polymerization complex without completion of incorporation. In some embodiments the same modification that includes the label functions as the reversible terminator so a separate modification is not required to attach the terminator to the nucleotide. In some embodiments the excitation illumination acts in the vicinity of the target polynucleotide and diminishes in the broader reaction volume. In some embodiments the cleavage trigger acts in the vicinity of the target polynucleotide and diminishes in the broader reaction volume. In some embodiments the unincorporated nucleotides are moved away from the surface where the cleavage trigger and/or excitation illumination occurs. In some embodiments the reaction mix is well agitated in order to remove spent reagents and to bring in fresh reagents to the sites of reaction. In some embodiment all the steps of the sequencing in the one pot reaction are conducted in a single reaction volume. In some embodiments the nucleotides are not directly labeled.

A general embodiment of the invention includes the following claims:

1. A method for template-directed sequencing of a polynucleotide template, the method comprising:

(a) providing the polynucleotide template in a fluidic vessel;

(b) contacting the polynucleotide template with a solution comprising (i) polymerization complex (comprising polymerase, primer and divalent catons) and nucleotides or nucleotide analogues comprising A,C,G, and T/U;

(c) using the polymerization complex to form an interaction of one of the nucleotides with one position in the sequence of the polynucleotide template such that a signal from a label associated with the polymerization complex or nucleotide is detected and its location recorded;

(d) detecting such signals for the one position in the sequence of (c), multiple times to obtain a consensus base call (e) repeating steps (b)-(d) where at each iteration a consensus base call for next position in the sequence is obtained 2. A method according to 1 where the signals are used to determine the location of the label associated with the polymerization complex or nucleotide and thereby the location of the sequence being determined 3. A method according to 1 where the localized signals are used to determine the location of the label associated with the polymerization complex or nucleotide and thereby the location of the sequence being determined within a high density of template sequences 3. A method according to 1 where the label is associated with the polymerase 4. A method according to 13 where the each nucleotide is added separately 5. A method according to 1 where the label is attached to the nucleotide 6. A method according to 1 where the signal is generated by the binding of a fluorescent label to the label attached to the nucleotide 7. A method according to previous claims where the signal is transient 8. A method according to one where the shift to the next position is done by forming a covalent bond between a nucleotide and the growing chain 9. A method according to previous claims where the signal from the sequences is localized to sub-diffraction accuracy which can be as low as a few nanometers or even sub-nanometer accuracy.

10. A method according to previous claims where the signal from the sequences is resolved within a high density of signals where such signals are separated by sub-diffraction distances, e.g. 200 nm 100 nm, 50 nm 20 nm, 10 nm, 5 nM, 1 nm.

Specific embodiments of the following include the following numbered 1 to 21:

1. Intercalator dye (intercalant) donor, acceptor and terminator on base (see FIG. 1):

In some embodiments of the invention the method of sequencing a target polynucleotide can include:

(a) incorporating a plurality of intercalating dye molecules into the target polynucleotide;

(b) contacting the target polynucleotide with a solution comprising a polymerase and four types of differently labeled nucleotides, wherein each differently labeled nucleotide comprises the structure:

wherein B is a purine or pyrimidine base, T is a photocleavable terminator group chemically bound to B, and L is a label comprising a fluorescence resonance energy transfer (FRET) partner to the intercalating dye molecules;

(c) incorporating one of the differently labeled nucleotides, using the polymerase, into a chain complementary to the target polynucleotide;

(d) illuminating the target polynucleotide with a first wavelength of electromagnetic radiation, inducing FRET on the intercalating dye and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

2. Intercalator dye donor, acceptor and terminator on sugar (see FIG. 1)

In some embodiments of the invention the method of sequencing a target polynucleotide can include:

(a) incorporating a plurality of intercalating dye molecules into the target polynucleotide;

(b) contacting the target polynucleotide with a solution comprising a polymerase and four types of differently labeled nucleotides, wherein each differently labeled nucleotide comprises the structure:

S-T-L, wherein S is a sugar, T is a photocleavable terminator group chemically bound to S, and L is a label comprising a fluorescence resonance energy transfer (FRET) partner to the intercalating dye molecules;

(c) incorporating one of the differently labeled nucleotides, using the polymerase, into a chain complementary to the target polynucleotide;

(d) illuminating the target polynucleotide with a first wavelength of electromagnetic radiation, inducing FRET on the intercalating dye and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

3. Intercalator dye donor, acceptor on base, terminator on sugar (see FIG. 1)

In some embodiments of the invention the method of sequencing a target polynucleotide can include:

(a) incorporating a plurality of intercalating dye molecules into the target polynucleotide;

(b) contacting the target polynucleotide with a solution comprising a polymerase and four types of differently labeled nucleotides, wherein each differently labeled nucleotide comprises the structure:

L-B—S-T, wherein S is a sugar, T is a photocleavable terminator group chemically bound to S, and L is a label attached to the base, such label is photocleavable (via a linker so that it can be removed) or is photoinactivatable (e.g., its fluorescence is diminished via photinactivation/photobleaching);

(c) incorporating one of the differently labeled nucleotides, using the polymerase, into a chain complementary to the target polynucleotide;

(d) illuminating the target polynucleotide with a first wavelength of electromagnetic radiation, inducing FRET between the intercalating dye and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group and removing the photocleavable label or inactivating the photoinactivatable label; and (f) repeating steps (a)-(e) as a homogeneous or one pot reaction, thereby sequencing the target polynucleotide.

In some embodiments, instead of using intercalating dyes in the above embodiments any DNA stain can be used or any entity that can act as a DNA stain can be used. For example the DNA stain may be a conjugated polymer. The stain may be a labeled spermine polymer. The DNA stain may be a DNA binding peptide or polypeptide. The DNA stain may be an antibiotic such as Actinomycin D.

In some embodiments one or more donors may be on the polymerase.

4. Label on polymerase donor, acceptor and terminator on base (see FIG. 2)

In some embodiments of the invention the method of sequencing a target polynucleotide can include:

(a) Attaching a FRET donor (directly or indirectly) to a polymerase;

(b) contacting the target polynucleotide with a solution comprising a polymerase and four types of differently labeled nucleotides, wherein each differently labeled nucleotide comprises the structure:

B-T-L, wherein B is a purine or pyrimidine base, T is a photocleavable terminator group chemically bound to B, and L is a label comprising a fluorescence resonance energy transfer (FRET) partner to the FRET donor attached directly or indirectly to the polymerase;

(c) incorporating one of the differently labeled nucleotides, using the polymerase, into a chain complementary to the target polynucleotide;

(d) illuminating the target polynucleotide with a first wavelength of electromagnetic radiation, inducing FRET between FRET partner attached directly or indirectly to the polymerase and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

5. Label on polymerase donor, acceptor and terminator on sugar (see FIG. 2)

In some embodiments of the invention the method of sequencing a target polynucleotide can include:

(a) Attaching a FRET donor (directly or indirectly) to a polymerase;

(b) contacting the target polynucleotide with a solution comprising a polymerase and four types of differently labeled nucleotides, wherein each differently labeled nucleotide comprises the structure:

S-T-L, wherein S is a sugar, T is a photocleavable terminator group chemically bound to S, and L is a label comprising a fluorescence resonance energy transfer (FRET) partner to the FRET donor attached directly or indirectly to the polymerase;

(c) incorporating one of the differently labeled nucleotides, using the polymerase, into a chain complementary to the target polynucleotide;

(d) illuminating the target polynucleotide with a first wavelength of electromagnetic radiation, inducing FRET between FRET partner attached directly or indirectly to the polymerase and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

6. Label on polymerase donor, acceptor on base and terminator on sugar (see FIG. 2)

In some embodiments of the invention the method of sequencing a target polynucleotide can include:

a) Attaching a FRET donor (directly or indirectly) to a polymerase;

(b) contacting the target polynucleotide with a solution comprising a polymerase and four types of differently labeled nucleotides, wherein each differently labeled nucleotide comprises the structure:

L-B—S-T, wherein S is a sugar, T is a photocleavable terminator group chemically bound to S, and L is a label attached to the base, such label is photocleavable (via a linker so that it can be removed) or is photoinactivatable (e.g., its fluorescence is diminished via photo inactivation or photobleaching) comprising a fluorescence resonance energy transfer (FRET) partner to the FRET donor attached directly or indirectly to the polymerase;

(c) incorporating one of the differently labeled nucleotides, using the polymerase, into a chain complementary to the target polynucleotide;

(d) illuminating the target polynucleotide with a first wavelength of electromagnetic radiation, inducing FRET on the intercalating dye and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group and removing the photocleavable label or inactivating the photoinactivatable label; and (f) repeating steps (a)-(e) as a homogeneous or one pot reaction, thereby sequencing the target polynucleotide.

In some embodiments the locations of the FRET donor and acceptor are reversed. For example the donor may be on the nucleotide and acceptor may be on the polymerase or in the duplex.

In some embodiments the FRET described above in embodiments 1-6 is replaced by photoactivation. In this case the FRET donor (Intercalator dye or label on the base) becomes a photo activator and the FRET acceptor (label on the nucleotide) becomes a fluor in an inactivated or darkened state. When the darkened fluor is in close proximity to the activator its fluorescence is switched on.

7. Label on polymerase donor, quencher and terminator on nucleotide (See FIG. 3)

In some embodiments of the invention the method of sequencing a target polynucleotide can include:

(a) attaching a Resonance Energy Transfer (RET) donor (directly or indirectly) to a polymerase;

(b) contacting the target polynucleotide with a solution comprising a polymerase and four types of differently labeled nucleotides, wherein each differently labeled nucleotide comprises the structure:

N-T-Q, wherein N is a nucleotide, T is a photocleavable terminator group chemically bound to N, and Q is a label comprising a quencher partner to the donor attached directly or indirectly to the polymerase;

(c) incorporating one of the differently labeled nucleotides, using the polymerase, into a chain complementary to the target polynucleotide;

(d) illuminating the target polynucleotide with a first wavelength of electromagnetic radiation, inducing energy/electron transfer between the donor and the incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

The quenching mechanism can be a special case for RET, where the energy is not dissipated as light by the acceptor.

The quencher and terminator can both be on the base or both be on the sugar. Alternatively, the quencher can be on the base and the terminator on the sugar. The cleavable linkage can be chemically cleavable and is cleavage is performed chemically.

8. BRET donor on polymerase, acceptor and terminator on nucleotide (See FIG. 4)

The present invention relates to a method of sequencing a target polynucleotide. In various aspects and embodiments, the methods include the steps of:

(a) providing a bioluminescent biomolecule, attached or fused to a polymerase (or ligase);

(b) contacting the target polynucleotide with a solution (reaction volume) comprising four types of differently labeled nucleotides, wherein each differently labeled nucleotide comprises the structure:

N-c-L(T)

or

T-c-N-c-L wherein N is a nucleotide, c is a cleavable linker, T is a terminator group chemically linked to N, and L is a label chemically linked to N, L(T) is a structure that acts as a label and a terminator wherein L is specific for A, C, G, T/U and c is a cleavable linker (c) incorporating one of the differently labeled nucleotides, using the polymerase with the attached/fused bioluminescent molecule, into a chain complementary to the target polynucleotide;

(d) providing substrates that enable the bioluminescent reaction to occur, and thereby identifying the type of the differently labeled nucleotide incorporated via bioluminescent resonance energy transfer (BRET) from the bioluminescent molecule to the label on the nucleotide and detecting the resulting electromagnetic radiation;

(e) cleaving the cleavable linker, thereby removing the cleavable terminator group and label; and (f) repeating steps (a)-(e), thereby sequencing the target polynucleotide.

In some BRET embodiments the linker is photocleavable linker and step (e) comprises illuminating the target polynucleotede. The acceptor and terminator can both be on the base or both on the sugar. Alternatively, the acceptor can be on the base and the terminator on the sugar. In addition, the BRET acceptor can be a quencher rather than an emitter of fluorescence.

10. Waveguides/plasmonic structures and label/terminator on nucleotide

In some embodiments of the invention the method of sequencing a target polynucleotide can include:

(a) inserting target polynucleotide into waveguide/plasmonic structure within which the majority of the excitation energy is confined (and/or within which the potential for enhanced excitation exists);

(b) contacting the target polynucleotide with a solution comprising a polymerase and four types of differently labeled nucleotides, wherein each differently labeled nucleotide comprises the structure:

N-$c$-L(T)

or

T-$c$-N-$c$-L wherein N is a nucleotide, c is a cleavable linker, T is a terminator group chemically linked to N, and L is a label chemically linked to N, L(T) is a structure that acts as a label and a terminator wherein L is specific for A, C, G, T/U and c is a cleavable linker (c) incorporating one of the differently labeled nucleotides, using the polymerase, into a chain complementary to the target polynucleotide;

(d) illuminating the target polynucleotide with a first wavelength of electromagnetic radiation, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

11. Direct detection of label on nucleotide In some embodiments of the invention the method of sequencing a target polynucleotide can include:

(a) positioning target polynucleotide at the focal plane of detection;

(b) contacting the target polynucleotide with a solution comprising a polymerase and four types of differently labeled nucleotides, wherein each differently labeled nucleotide comprises the structure:

N-$c$-L(T)

or

T-$c$-N-$c$-L wherein N is a nucleotide, c is a cleavable linker, T is a terminator group chemically linked to N, and L is a label chemically linked to N, L(T) is a structure that acts as a label and a terminator wherein L is specific for A, C, G, T/U and c is a cleavable linker (c) incorporating one of the differently labeled nucleotides, using the polymerase, into a chain complementary to the target polynucleotide;

(d) illuminating the target polynucleotide with a first wavelength of electromagnetic radiation, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

In some embodiments when the target polynucleotide is attached to a surface, the surface preferably has 3D gel architecture so that a higher concentration of polynucleotide can be loaded onto a location on a surface, without increasing its 2D footprint. This can help obtain a signal detectable over background.

12. Open-Closed Complex

The method of this embodiment comprises:

(a) disposing the target polynucleotide within an area of a fluidic vessel (b) contacting the target polynucleotide with a solution (reaction volume) comprising (i) polymerization complex and (ii) four types of differently labeled nucleotides, wherein each differently labeled nucleotide comprises the structure:

NP-L wherein NP is a nucleotide phosphate, L is a label chemically linked to NP and L is specific for A, C, G, T/U (c) forming a closed complex of the polymerase and one of the differently labeled nucleotides, on the target polynucleotide in the absence of divalent cation;

(d) detecting the signal for the type of nucleotide persistently proximal to the target polynucleotide sequence above signal from nucleotides not persistently proximal to the target polynucleotide sequence and thereby identifying the type of the differently labeled nucleotide being incorporated;

(e) bathing the polynucleotides with divalent cation, thereby allowing the nucleotide incorporation to complete, without incorporation of further nucleotides; and (f) repeating steps (b)-(e) without external reagent input into the vessel, thereby sequencing the target polynucleotide, (e.g., based on the assumption that the target polynucleotide contains nucleotides that are complementary to the ones incorporated).

A RET mechanism can be employed with the labels on the nucleotides being RET acceptors and an intercalator dye or a label or labels associated with the polymerizing agent being the RET donor. The RET acceptors can be quenchers.

13. Reagent Packet (FIG. 5)

In some embodiments of the invention the method of sequencing a target polynucleotide can include:

(a) providing a reagent packet sufficient for one sequencing cycle, each packet containing at least two fluidic sub-packets containing sequencing reagents (including nucleotides)

(b) sequentially contacting the target polynucleotide with the reagents in the sub-packets, (c) adding one labeled nucleotides from a group of one or more nucleotides, A, C, G, T/U (wherein the label and optionally a terminator is cleavable), using the polymerase, into an elongation/polymerization complex;

(d) stimulating the target polynucleotide with a wavelength of electromagnetic radiation or bio or chemiluminescence reagent, detecting the resulting electromagnetic emission and thereby determining the identity of the differently labeled nucleotide incorporated;

(e) cleaving the label (and terminator if present) on the nucleotide;

(f) commencing to the next reagent sub-packet; and (g) repeating steps (b)-(f) thereby sequencing the target polynucleotide.

Optionally wherein (e) and (f) may require the same physical trigger. In some embodiments the same packet (comprising a set of sub-packets) is passed over the target polynucleotides multiple times in the process of producing a sequencing read, once for each cycle (see FIG. 5).

14. Multiple Reagent Packets (FIG. 6)

In some embodiments the method of sequencing a target polynucleotide occurs via an elongation/polymerization complex and a packet comprising sub-packets which sequentially pass over the target polynucleotides. Such embodiments include the steps of:

(a) providing a series of fluidic sub-packets (or capsule or droplet), each sub-packet in the series containing reagents for one step of the sequencing cycle, each sequencing fluidic sub-packet separated by a non-reactive packet, gap or space comprising an agent that is substantially immiscible with the fluidic packets (e.g. air or oil) containing the sequencing reagents (b) contacting the target polynucleotide with the reagents in the sequencing packets such that when the target polynucleotide is contacted with a reagent sub-packet containing one or more labeled nucleotides (and optionally terminator), one of the labeled nucleotides is added into the elongation complex using the polymerase;

(c) illuminating the target polynucleotide with a wavelength of electromagnetic radiation (or if the polymerase is linked to a bioluminescent/chemiluminescent donor, providing co-factor for bioluminescence/chemiluminescence), detecting the resulting electromagnetic emission and thereby determining the identity of the differently labeled nucleotide incorporated;

(d) contacting the target polynucleotide with a reagent sub-packet containing a cleavage reagent (or a buffer that promotes photochemical cleavage) allowing the label on the nucleotide to be cleaved; and (e) repeating steps (b)-(d) thereby sequencing the target polynucleotide.

In some embodiments a different (but in most cases, identical) packet (comprising a set of sub-packets) is passed over the target polynucleotide for each cycle (see FIG. 6).

15. Shifting reagents between compartments in the fluidic device

In some embodiments the method comprises:

(a) disposing the target polynucleotide within an area of a fluidic vessel (b) contacting the target polynucleotide with a solution (reaction volume) comprising (i) polymerization complex and (ii) four types of differently labeled nucleotides, wherein each differently labeled nucleotide comprises the structure:

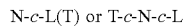

N-$c$-L(T) or T-$c$-N-$c$-L wherein N is a nucleotide, T is a terminator group chemically linked to N, and L is a label chemically linked to N, L(T) is a label that acts as a terminator wherein L is specific for A, C, G, T/U and c is a cleavable linker;

(c) incorporating one of the differently labeled nucleotides, using the polymerization complex, into a chain complementary to the target polynucleotide;

(d) moving the labeled nucleotides to an area of the vessel not containing the target polynucleotides and detecting the signal for the type of nucleotide persistently proximal to the target polynucleotide above signal from nucleotides not persistently proximal to the target polynucleotide and thereby identifying the type of the differently labeled nucleotide incorporated;

(e) cleaving the cleavable linker (s), thereby removing the terminator group and the label;

(f) moving the labeled nucleotides into the area of the vessel containing the target polynucleotides; and (g) repeating steps (b)-(f) without external reagent input into the vessel, thereby sequencing the target polynucleotide, (e.g., based on the assumption that the target polynucleotide contains nucleotides that are complementary to the ones incorporated).

The above embodiment can be carried out in a fluidic device comprising at least two compartments, one for the incorporation mix and one for the cleavage mix. The above mechanism can be combined with other embodiments of the invention (e.g., the aspects described above and below).

For 13, 14, and 15 optionally each of the four nucleotides is provided in a different sub-packet and are optionally not differently labeled from each other (but the order of delivery of the sub-packets containing them is known). In some embodiments the four nucleotides are not labeled but a different component of the complex is labeled, for example the polymerizing agent and again the order of delivery of the sub-packets containing them is known. Individual polynucleotides or clonal amplicons thereof are detected.

16. Moving target polynucleotide sequence in and out of flowstream (FIG. 7A and FIG. 7B)

In some embodiments of the invention the method of sequencing a target polynucleotide can include:

(a) attaching the target polynucleotide within a first zone on the surface of a fluidic vessel;

(b) contacting the target polynucleotide with a flowstream comprising (i) polymerization complex and (ii) four types of differently labeled nucleotides;

(c) using the polymerization complex to add one labeled nucleotide (optionally with reversible terminator) from the group comprising one or more labeled nucleotides, A, C, G or T/U into a chain complementary to the target polynucleotide with the constraint that only one labeled modified nucleotide can be added;

(d) providing an electrical field perpendicular to the flowstream causing the polynucleotide to stretch from the point of its attachment in the first zone to a second zone so that the majority of the molecule is no longer in the first zone in which the reagents described in (b) are present (e) detecting the added labeled nucleotide above signal from labeled nucleotides that are not added and recording the identity of the differently labeled modified nucleotide added;

(e) removing the label and the constraint that allowed only one labeled modified nucleotide to be added; and (f) repeating steps (b)-(e) without external reagent input into the vessel, thereby sequencing the target polynucleotide, (e.g., based on the assumption that the target polynucleotide contains nucleotides that are complementary to the ones incorporated).

In some embodiments the flowstream comprises a laminar flow.

17. Superesolution sequencing using Point Accumulation for Imaging in Nanoscale Topography (PAINT) (See FIG. 8)

In some embodiments of the invention the method of sequencing a target polynucleotide can include:

(a) positioning the target polynucleotide into surface/focal plane;

(b) contacting the target polynucleotide with a solution comprising (i) polymerase (initiation+extension complex) and (ii) four types of differently labeled nucleotides, wherein each differently labeled nucleotide comprises the structure:

N—X-LBP(T)

wherein N is nucleotide, X represents a chemical cleavable or photocleavable linker group chemically bound to LBP and LBP is a Label binding partner and acts as the terminator (T) or a separate terminator moiety is provided on the nucleotide also connected to the nucleotide via a chemical cleavable photocleavable linker

T-X—N—X-LBP wherein the label comprises the first partner of a binding pair comprising an oligonucleotide sequence as a docking site for a PAINT (e.g. DNA PAINT) imager and (iii) four distinct PAINT (e.g. DNA PAINT) imagers (c) using the polymerase to incorporate into a chain complementary to the target polynucleotide one of the differently labeled nucleotides comprising binding partner 1 onto which one of the four binding partner 2 imager strands is able to repetitively bind on and off;

(d) imaging/taking a movie under continuous illumination with a first wavelength of electromagnetic radiation, and detecting a persistent signal at specific locations on the surface (using single molecule localization algorithms), thereby identifying the identity of the differently labeled nucleotide incorporated at those locations;

(e) illuminating the target polynucleotide with a second wavelength of electromagnetic radiation or exposing the target polynucleotide to a chemical or biochemical reagent to induce the cleavage, thereby removing the chemical or photocleavable label/terminator group described in (b); and (f) repeating steps (b)-(e) thereby sequencing the target polynucleotide.

In some embodiments PAINT is carried out as a homogeneous or one pot reaction,

In some embodiments the PAINT technique is combined with the other aspects described above ore elsewhere in this document. In some embodiments the pronounced or persistent PAINT signal at template locations is sufficient to distinguish the signal over background. The PAINT technique provides the background rejection without utilization of RET or other surface signal enhancement methods, it only requires the persistent signals at locations on the focal plane or surface to be detected. In some embodiments FRET or BRET can be combined with PAINT, so that illumination with four separate lasers is not required.

18. Superesolution sequencing using Stochastic Optical Reconstruction Microscopy (STORM)

In some embodiments of the invention the method of sequencing a target polynucleotide can include:

(a) positioning the target polynucleotide into surface/focal plane;

(b) contacting the target polynucleotide with a solution comprising (i) polymerase (initiation+extension complex) and (ii) four types of differently labeled nucleotides, wherein each differently labeled nucleotide comprises the structure:

N—X-PL(T)

wherein N is nucleotide, X represents a chemical or photocleavable linker group chemically bound to PL and PL is a Label that is capable of photoswitching or blinking and acts as the terminator (T)

or a separate terminator moiety is provided on the nucleotide also connected to the nucleotide via a chemical cleavable or photocleavable linker

T-X—N—X-PL wherein PL is a label capable of photoswitching or blinking (c) using the polymerase to incorporate into a chain complementary to the target polynucleotide one of the differently labeled nucleotides;

(d) imaging/taking a movie under continuous illumination with a first wavelength of electromagnetic radiation, and detecting a persistent signal at specific locations on the surface (using single molecule localization algorithms), thereby identifying the identity of the differently labeled nucleotide incorporated at those locations;

(e) illuminating the target polynucleotide with a second wavelength of electromagnetic radiation, thereby removing the photocleavable label/terminator group described in or exposing the target polynucleotide to a chemical or biochemical reagent to induce the cleavage (b); and (f) repeating steps (b)-(e) thereby sequencing the target polynucleotide.

19. Superesolution sequencing by Transient Binding of Nucleotides

In some embodiments of the invention the method of sequencing a target polynucleotide can include:

(a) positioning the target polynucleotide into surface/focal plane;

(b) contacting the target polynucleotide with a solution comprising (i) polymerase (initiation+extension complex) and (ii) four types of reversible terminators (in some embodiments the reversible terminators are unlabeled, in others they are labeled)

wherein each reversible terminator nucleotide comprises the structure:

N—XT wherein N is nucleotide, X represents a chemical, biochemical cleavable or photocleavable group chemically bound to a terminator (T), which may be an actual or virtual terminator (c) using the polymerase to incorporate into a chain complementary to the target polynucleotide one of the reversible terminator nucleotides;

(d) Adding a nucleotide such nucleotides comprise the structure,

N-L

Wherein N is a nucleotide and L is a label (e) imaging/taking a movie under illumination with one or more wavelength of electromagnetic radiation, and detecting a persistent signal from the labeled nucleotides at specific locations on the surface (using single molecule localization algorithms), thereby identifying the identity of the differently labeled nucleotide incorporated at those locations;

(e) illuminating the target polynucleotide with a second wavelength of electromagnetic radiation or exposing the target polynucleotide to a chemical or biochemical reagent to induce the cleavage, thereby removing the chemical, biochemical or photocleavable label/terminator group described in (b); and (f) repeating steps (b)-(e) thereby sequencing the target polynucleotide.

In some embodiments of 19 the reversible terminators also labeled and provides an independent reading of the base ahead of the transient binding nucleotide or acts as a RET partner to the transiently binding nucleotide.

20. Superesolution sequencing by Transient Binding of Nucleotides

In some embodiments of the invention the method of sequencing a target polynucleotide can include:

(a) positioning the target polynucleotide into surface/focal plane;

(b) contacting the target polynucleotide with a solution comprising (i) polymerase (initiation+extension complex) and (ii) four types of labeled reversible terminators wherein each reversible terminator nucleotide comprises the structure:

wherein N is nucleotide, L represents a label attached to a phosphate of the nucleotide (T), which may be an actual or virtual terminator (c) using the polymerase to incorporate into a chain complementary to the target polynucleotide one of the reversible terminator nucleotides so that L is part of the leaving group;

(d) Allowing unincorporated labeled nucleotides to transiently bind to the next position in the chain without chemically getting incorporated due to the presence of the terminator at the end of the growing chain (e) imaging/taking a movie under illumination with one or more (used simultaneously or one after another) wavelength of electromagnetic radiation, and detecting a persistent signal from the labeled nucleotides at specific locations on the surface (preferably using single molecule localization algorithms), thereby identifying the identity of the differently labeled nucleotides transiently binding at those locations;

(e) illuminating the target polynucleotide with a second wavelength of electromagnetic radiation or exposing the target polynucleotide to a chemical or biochemical reagent to induce the cleavage, thereby removing the chemical, biochemical or photocleavable terminator group described in (b); and (f) repeating steps (b)-(e) thereby sequencing the target polynucleotide.

In some embodiments the transiently binding nucleotide is in a darkened state (for example Cy5 can be darkened by using NaBH4) prior to binding and is photoactivated by a label on the polymerization complex, including a label on the polymerase, a label on the incorporated terminator or a DNA stain in the template. In some embodiments of aspects 19 and 20 the transient binding is not used for superresolution but is used just for imaging (for example so that the labels are replenished).

21. Superesolution sequencing using Stimulated Emission Depletion (STED)

In some embodiments of the invention the method of sequencing a target polynucleotide can include:

(a) positioning the target polynucleotide into surface/focal plane;

(b) contacting the target polynucleotide with a solution comprising (i) polymerase (initiation+extension complex) and (ii) four types of differently labeled nucleotides, wherein each differently labeled nucleotide comprises the structure:

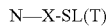

wherein N is nucleotide, X represents a chemical or photocleavable linker group chemically bound to SL and SL is a Label that is compatible with STED as the terminator (T)

or a separate terminator moiety is provided on the nucleotide also connected to the nucleotide via a chemical cleavable or photocleavable linker

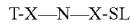

wherein SL is a label capable of STED (c) using the polymerase to incorporate into a chain complementary to the target polynucleotide one of the differently labeled nucleotides;

(d) scanning as STED beam with a first wavelength of electromagnetic radiation, and detecting signal at specific locations on the surface, thereby identifying the identity of the differently labeled nucleotide incorporated at those locations;

(e) illuminating the target polynucleotide with a second wavelength of electromagnetic radiation, thereby removing the photocleavable label/terminator group described in or exposing the target polynucleotide to a chemical or biochemical reagent to induce the cleavage (b); and (f) repeating steps (b)-(e) thereby sequencing the target polynucleotide.

In some embodiments the excitation beam is a single beam that excites a FRET donor and in some embodiments the depletion beam is a single beam that depletes the FRET donor. In some embodiments the STED beams are scanned at video rate or at a greater rate which is synchronised with the read-out of a CCD or CMOS camera.

Some super-resolution mechanisms described herein enable molecules to be superesolved, because labels in a closely packed field do not fluoresce at exactly the same times.

In some super-resolution PAINT methods the bases are coded by fluorescent wavelength, In some super-resolution PAINT methods the bases are coded by intensity of fluorescent signal rather than wavelength. In some PAINT methods of the invention the tag/anti-tag complex has a fast association rate due to physical conditions such as high concentration, high temperature, high pressure, active electrical or magnetic control of binding, agitation/mixing and a fast dissociation rate due to low stability of transient complex, high temperature and active or magnetic control. The fast dissociation rate means that there is a sort dwell time of the anti-tag imagers at a particular location but sufficient photons need to be collected for high precision localization. Consequently, much brighter imagers are used including multi-labeled structures and nanoparticles such as gold or silver nanoparticles.

In some super-resolution methods, the labels on the label on the nucleotides are not chosen for special super-resolution qualities, e.g. they are not chosen for compatibility with STED or STORM, instead an increase in resolution is achieved by taking advantage of the fact that each different colour is separately imaged and can be separately localized. In another embodiment, the nucleotides are imaged with high temporal resolution while they each binding to a molecule in the array of templates, and because the this binding is a stochastic process, each nucleotide within diffraction limited area will incorporate at slightly different times and can therefore be localized with high precision. Similarly, when sequencing is conducted in a real-time manner using terminal phosphate labeled nucleotides, where the labeled phosphate is part of the leaving group upon incorporation, even where the molecules are densely packed, the majority of nucleotides incorporation events within a diffraction limited spot can be temporally resolved and hence super-resolved.

In some embodiments the photocleavable label/terminator is replaced with a chemically cleavable label/terminator. In some embodiments the chemical cleavage is by generation of acid, using photo-generation or electrical acid generation methods. In some embodiments the chemical cleavage is not homogenous but involves exchange of reagents atop the array of sequencing templates. In some embodiments the cleavage is due to biochemical reagents. For example a peptide linker can be cleaved by protease or other kinds of moieties (diesterases or modifications that resemble DNA damage adducts for example) can be repaired by selected components of DNA repair systems, for example T4 Endonuclease IV and Exonuclease III are able to remove non-canonical moieties at the 3' end of nucleotides.

In some embodiments of this invention methods to overcome the effect of non-specific adsorption are described. These include passivation of surfaces and computational filtering of aberrant signals through the data stack. In some embodiments of this invention methods to overcome the effect of background signal from the bulk solution are described.

In embodiments of the invention, the various methods described for reducing the amount of reagents used in sequencing or reducing or eliminating the background fluorescence problem in a homogeneous reaction or super-resolution, are combined with the cleavable terminator nucleotides and polymerases described in this invention.

In some embodiments the super-resolution sequencing methods of this invention are carried out in a homogeneous format.

In some embodiments the cleavable linker is not a photocleavable linker but instead is cleavable by some other physical trigger. The physical trigger in some embodiments is an electrochemically generated (e.g., via a voltage being applied to an electrode) acid and the cleavable linker is cleavable by acid.

In some embodiments specific advantages of the mechanisms described in this invention are used in other sequencing scenarios, for example using neither homogeneous format nor super-resolution. One such case is a non-homogeneous sequencing reaction, where cleavage is conducted chemically with the exchange of reagents but where a DNA stain or intercalator dye is used as a fluorescent donor to four nucleotides bearing acceptors. The advantage of this over conventional SbS is twofold. Firstly just a single wavelength of light is needed for excitation. Secondly, non-specific adsorption of labeled nucleotides on the surface can be differentiated form those that are incorporated, as only the latter will be subject to FRET.

The method of the invention can be carried out on surface immobilized templates, or templates contained in micro- or nano-wells, channels, slits, droplets and beads.

In some embodiments, sequencing is conducted on templates that are closer than would be resolvable by diffraction limited optical imaging but are resolved by super-resolution imaging.

Such a super-resolution method for template-directed sequencing-by-synthesis of a polynucleotide comprises:

(a) providing four reversibly terminated nucleotides, A,C, G,T/U each modified with their own distinct label, each said label being capable of stochastic optical reconstruction (blinking, switchable, stochastic occurrence of binding etc.);

(b) incorporating reversibly terminated nucleotides, bearing said distinct labels across an array of templates;

(c) taking an image of the location of binding of each distinct label across the array (where a movie is taken to capture all the stochastic labels);

(d) reversing termination and removing label; and (e) repeat step b-d until read of desired length has been obtained.

The stochastic optical reconstruction method can be combined with all of the aspects described above.

In some embodiments the stochastic optical reconstruction method is carried out by using binding pairs and DNA PAINT (Jungmann et al Nano Lett. 2010, 10: 4756) as described in 17. Each nucleotide comprises a distinct oligonucleotide sequence which is a docking site for a distinct DNA PAINT imager strand. In some embodiments the stochastic optical reconstruction is carried out by recording the transient binding of nucleotides or polymerase. In some embodiments stochastic optical reconstruction is carried out by recording the blinking or photoswitching of molecular or particulate single emitters or point light sources.

While some super-resolution methods will still suffer from bleaching and photophysical effects. The DNA PAINT system will not suffer appreciably from such effects but remains susceptible to incorporation of the wrong base before detection has occurred. The transient nucleotide binding approach is robust to both detecting the correct base and for avoiding photophysical effects and has the potential for the greatest accuracy of any sequencing approach.

During the incorporation step it is desirable to have a high concentration of nucleotides and polymerizing agent in the vicinity of the target polynucleotide. However, during the detection step it is undesirable to have unincorporated and unloaded polymerizing agent (if labeled) in the vicinity of the target polynucleotides. This is particularly the case for the unincorporated nucleotides. This is because when the nucleotides are labeled, they cause unnecessary background fluorescence, which makes it hard to detect the incorporated nucleotides on the surface.

In some embodiments the fluid is sandwiched between a top and a bottom surface. The bottom surface contains the target polynucleotides. The bottom surface may contain features that promote the entry of the nucleotides to the bottom surface, for example the nucleotides bear a negative charge and the bottom surface may be provided with a positive bias to attract the nucleotides and the top surface may provide a negative bias. This is done during the incorporation step. Then the bias may be switched between the top and bottom surface depending on whether it is desirable to have the nucleotides in the vicinity of the polynucleotide target (during incorporation) or away from the polynucleotide target (during detection and cleavage). See FIG. 9A and FIG. 9B.

The positive potential on the second surface (not containing the templates being sequenced) is applied after incorporation, before cleavage is directed at the first surface, to prevent the unincorporated nucleotides from being cleaved. In this case the cleavage mechanism does not have a reach to the second surface, and does not cleave the nucleotides that have been attracted there. An electric field generated at the surface is a useful way for controlling the attraction and repulsion of nucleotides at the surface (Asanov 1998; Sosnowski 1997).

In the case of DNA PAINT, non-fluorescent nucleotides can be provided at the high concentrations (250 nM range) needed by polymerases to drive the incorporation reaction. However, the imaging step requires a concentration of the imager in the 1-10 nM range and at such concentrations, when using TIRF imaging, there is little background fluorescence and each single molecule/particle emitter interacting with the surface can be clearly seen. If the on-rate is increased by increasing concentration, then further measures such as FRET between the imager and a component of polymerization complex or quenching (e.g. the imager strand forms a molecular beacon) are needed to keep the background fluorescence low. Similarly, when sequence detection is done by recording transiently binding nucleotides, a FRET mechanism can be used when a high concentration of transiently binding nucleotides is used. For example the FRET can be between a label on the reversible terminator and the incoming transiently binding nucleotides. Alternatively it can be between intercalting dyes such as YOYO-1, Sytox Green, JOJO-1 or Sytox Orange intercalated in the template-primer duplex and a label on the transiently binding nucleotide (each of which can be distinctly labelled. Every FRET event in this context does not need to be robustly detected, because other FRET events can be captured as transiently binding nucleotides repeatedly bind on and off.

Auer et al Nano Lett. 2017, 17, 6428-6434 (which is incorporated herein by reference in its entirety) have implemented DNA PAINT at ultra-fast speeds using high concentration of fluorescently labelled imager strand but where background fluorescence is overcome by exciting the imager via FRET mechanisms. Auer et al achieved localization precision of 19.5 nm, an image resolution of 46 nm by using 500 nM of Imager 14 ms integration time with 1000 frames taken in 28 s. This independently shows what this invention claims, that sequencing (using the transient binding aspects) of this invention can be carried out at high speeds when a FRET mechanism is used. It is a remarkable aspect of the present invention that although a movie is taken rather than a single image and single molecules rather than clusers are detected, sequencing speeds faster than current Illumina sequencing by synthesis methods are possible.

The FRET mechanisms of this invention, especially the use of intercalator dyes can be extended to various end-point assays and analysis methods other than sequencing, such as Fluorescent In Situ Hybridization assays etc. In some embodiments the binding of a probe such as an antibody or an oligonucleotide can be tagged with a DNA PAINT docking strand and a super-resolution image of the binding of the probe to sample molecules disposed in 2D or 3D can be obtained at high speeds by FRET-based imaging of the Imager.

In some embodiments individual nucleotides are labeled with single fluors. In other embodiments individual nucleotides are labeled with multiple fluors. In some embodiments the multiple fluors are the same and enable an improved signal-to-noise. In some embodiments the multiple fluors may comprise two or more different varieties, and enable coding to be implemented. In some embodiments the different nucleotides are labeled with a single color, but the number of fluors on the nucleotide, is distinct for each nucleotide type (A, C, G, T/U). For example, A can have 2 fluors, C, 6 fluors, G, 18 fluors, and T/U 48 fluors.

In some embodiments all four nucleotides are not added simultaneously and therefore do not need to be labeled differently. In some such embodiments, each of the four nucleotide types are added a nucleotide at a time. For example a fluorescent nucleotide bearing a terminator can be added one at a time, after addition of A for example, the locations on the surface where the label is incorporated are detected and then the label is removed from the nucleotide. In another example the nucleotide (from the set that is added one nucleotide type at a time) is unlabeled and detection is via a mechanism such as pyrosequencing (using firefly luciferase for examples) or pH as in Ion Torrent sequencing, or heat as in Genapsys sequencing.

In such embodiments, the invention comprises:

(a) disposing the target polynucleotide within a fluidic vessel;

(b) contacting the target polynucleotide with a solution comprising (i) polymerization complex and (ii) a nucleotide;

(c) using the polymerization complex to add the nucleotide into a chain complementary to the target polynucleotide;

(d) detecting the added nucleotide at the locations it is added; and (f) repeating steps (b)-(e), each time with a different nucleotide and without external reagent input into the vessel, thereby sequencing the target polynucleotide.

If a and reversible terminator is used it is removed after step d; if one is not used a multiple of the nucleotide is added when there is a homopolymer in the target.

This embodiment can be combined with 13, 14, and 15 described above. For example in 13 and 14, separate sub-packets are provided for each of the four nucleotides, or in 15, different compartments are provided for the storage of the different nucleotides. After initiation of the reaction the whole of the reaction is conducted in a closed vessel.

In some embodiments the reaction is homogeneous for certain steps but semi- or non-homogeneous for other steps. In some embodiments the homogeneous or one-pot sequencing reactions described in this invention are carried out multiple times. For example, the homogeneous reaction is carried out to sequence a length of 10 nucleotides. The homogeneous reaction is then stopped and a new set of reagents is added to carry out a second homogeneous sequencing reaction. Then a third, and so on until the desired read-length has been obtained.

Favourably, the method involves analysing molecules as members of an array and to sequence many molecules in parallel. Many target polynucleotides or many segments of a single target polynucleotide can be sequenced simultaneously. The invention is readily automated, both for small-scale and large-scale operation.

DETAILED DESCRIPTION OF INVENTION

System and Kits

The invention is readily automated, both for small-scale and large-scale operation. One aspect of the invention is a kit for sequencing comprising, a polymerizing agent, special nucleotides and optionally labels, anti-fade comprising anti-oxidants and, a flow cell or chip. The invention also includes systems and apparatus/instrumentation for carrying out sequencing automatically according to the methods described in this document.

We will start by discussing specific sequencing approaches in detail and then critical components of the sequencing system that are relevant across the board for the sequencing methods of the invention. This is split into the following sections: Sequencing Methods; Closed Systems; Nucleotides and Polymerases; Arrays and Templates; Labels; Fluidic Systems; Imaging Methods.

Sequencing Methods

The processing of sequencing relies on the base pairing that occurs between nucleotides to form a double stranded polynucleotide molecule, according to the Watson-Crick base paring rules. At each position in a nucleotide molecule, one of the four nucleotides can be incorporated. The nucleotide incorporated into the extending primer or into an RNA copy is normally the correct base that pairs with the base in the target polynucleotide. The identity of the base in the template can be determined as the Watson-Crick complement of the base that is incorporated. So if a T is incorporated, an A should be present in the template.

In several embodiments of the present invention provides a method of sequencing a target polynucleotide comprising the steps:

(a) Carrying out template derived nucleotide synthesis utilizing a labeled and reversibly terminated nucleotide wherein the label and terminator is attached to the nucleotide via a cleavable linkage;

(b) detecting the presence or absence of said labeled nucleotide within the synthesized polynucleotide;

(c) cleaving said label and terminator from said nucleotide; and (d) repeating steps a-c.

Preferably the four nucleotides can be differentially labeled e.g. each has a different fluorophore. In this case the primer and template polynucleotides are contacted with two or more of the labeled nucleotides at the same time. If required any free nucleotides are removed and incorporated bases are detected. The use of four differentially labeled nucleotides can allow continuous (real-time) monitoring of the synthesis process or for the reaction to be conducted in a homogeneous or one-pot manner. The supply of all four nucleotides also reduces misincorporation. In one alternative embodiment sequencing may be of only two labeled bases and the other two bases are provided but are unlabeled. After sequence information is obtained of the first two bases the sequencing repeated with the other two bases labeled.

Some embodiments of the invention can be applied to direct sequencing of single molecules. It has been shown by PacBio and ONT, that single molecule analysis enables long sequencing reads to be obtained. The monitoring of individual molecules for sequencing by synthesis has the advantage over Illumina's cluster sequencing approach is that there is no phasing problem asynchronous extensions can be followed with ease. In some embodiments of the invention 1-3 cycles are conducted to read one to three bases. In some embodiments 3-30 cycles are conducted to read 3-30 bases. In other embodiments 30-300 cycles are conducted to read 30-300 bases. In other embodiments 300-3000 cycles are conducted to read 300-3000 bases. In some embodiments 3000-30,000 cycles are conducted to read 3000-30,000 bases. In some embodiments >30,000 cycles are conducted or real-time sequencing is implemented to read >30,000 bases.

Polymerases can be adapted to incorporate non-native nucleotides and the non-native nucleotide can be structured in a way that makes them easier to incorporate e.g. by attaching the dye via an appropriate linker. The chemical composition of the linker is chosen so that it minimally perturbs the polymerase function. The label is held at a distance greater than 1 nucleotide, 3 nucleotides, 6 nucleotides, 12 nucleotides and may be between 13-150 atoms, 19-140 atoms, 36-130 atoms, 54-120 atoms, 72-110 atoms or 90-100 atoms. The polymerase can also be engineered or evolved to deal with particular nucleotide modifications.

The fluorophore on the nucleotide may be bleached as required to detect subsequent incorporations more easily. Alternatively, the fluorophore and the label may be removed (e.g. by cleavage) or the fluorophore can be chemically modified to remove the fluorescence.

In another embodiment, synthesis can be done in a stepwise manner, by only allowing the synthesis to increase by only a single nucleotide at a time. This can be done by providing a block to nucleotide incorporation beyond a single nucleotide. This can be achieved by providing a removable blocker/terminator. The nucleotide may be blocked by any type of terminator, for example a photocleavable 2-nitrobenzyl based blocking group. The cleavable bond can be cleaved by means of light (if it is photocleavable) Li et al PNAS; 100(2):414-9 (2003).

In one embodiment the terminator is a group that can removed by an enzyme. This is preferably done by removing nucleotides from the 3' end. Such agents include exonucleases, such as T4 Endonuclease IV, exonuclease III, phosphodiesterases and includes DNA polymerases which possess 3'-5' exonuclease activity. As an alternative to repair of the 3' end, the nucleotide may be blocked from extension by a 3' phosphate. This can then be repaired to OH by Polynucleotide Kinases, making the end competent for extension. It can also be repaired by a 3' to 5' exonuclease in the presence of nucleotides.

Superesolution Biochemistry
Super-Resolution Compatible Chemistry

In some embodiments SbS can be conducted by any means including those described in this invention, those described in the literature or patents or those available commercially but by using fluorescent labels that are compatible with super-resolution imaging and using super-resolution detection and/or image processing methods. When STED compatible nucleotides are used super-resolution can be achieved by STED. When STORM compatible nucleotides are used the super-resolution is achieved by taking a movie (multiple frames, e.g. 5000-10,000 frames) and reconstructing the image using single molecule localization approaches.

Super-Resolution Compatible Binding Pairs

In some embodiment, the linkage attaching the label to the nucleotide comprises a binding pair. One member of the binding pair is linked to the nucleotide, preferably via a cleavable bond. The other member of the binding pair is attached to the label such as a fluorescent dye or nanoparticle. A binding pair consists of two molecules, e.g. DNA or proteins, which specifically bind to one another. The members of a binding pair may be naturally derived or wholly or partially synthetically produced. One member of the pair of molecules has an area on its surface, which may have spatial organization of protrusion, cavity or physiochemical (e.g. polar groups) features, which specifically binds to and is therefore complementary to a particular spatial organization of features of the other member of the pair of molecules. Thus, the members of the pair have the property of binding specifically to each other. Examples of types of binding pairs are antigen-antibody, biotin-avidin, hormone-hormone receptor, receptor-ligand, enzyme-substrate. The use of a linkage comprising a member of a binding pair means that the nucleotide added onto the primer may be labeled after it has been incorporated into the primer. The nucleotide is attached, preferably via a cleavable linker to one member of a binding pair. The detectable label is attached to the other member of the binding pair. The detectable label can then be attached indirectly to the nucleotide as the two members of the binding pair bind one another.

Each of the four types of nucleotides can be attached to a different binding pair member. The other members of the binding pair can be labeled differentially, e.g., each is attached to a different fluorophore or nanoparticle. This allows all of the nucleotides to be added at the same time. The nucleotide incorporated is then labeled with the respective fluorophore via the binding pair mechanism. For example adenine is attached to biotin, and cytosine is attached to digoxigenin. The fluorophore indicating the presence of adenine is attached to avidin, and that for cytosine is attached to anti-digoxigenin antibody. In some embodiments the binding pairs are oligonucleotides that bear complementary sequences, this easily allows one to code for four different nucleotides with four different binding pairs.

Thus in one aspect the present invention provides a method of sequencing a target polynucleotide comprising the steps of;

(a) carrying out template derived nucleotide synthesis using a nucleotide attached by a removable linkage to one member of a binding pair;

(b) contacting said nucleotide with a label attached to the other member of the binding pair under conditions such that the two members of the binding pair bind to one another;

(c) detecting the presence or absence or said label;

(d) removal of said label and said binding pair by removing said removable linkage between the first member of the binding pair and the nucleotide; and (e) repeating steps a-d.

In some embodiments the method comprises template-directed SbS of a polynucleotide comprising:

(a) providing four reversibly terminated nucleotides, A,C, G,T/U each modified with its own distinct tag, each said tag being partner 1 of a binding pair;

(b) incorporating reversibly terminated nucleotides, bearing said distinct tag across an array of templates;

(c) adding partner 2 of each binding pair, said partner 2 bearing a distinct label for each nucleotide;

(d) taking one or more images of the location of binding of each distinct label across the array;

(e) reversing termination and removing partner 1 and/ partner 2 of the binding pairs; and (f) repeating step b-e until read of desired length has been obtained.

PAINT with Binding Pairs

In some embodiments partner 2 is added under conditions that encourage transient binding. In some embodiments the transient on and off binding is recorded over multiple detection events (movie). When partner 2 binds to the incorporated partner 1 a signal can be detected and then when after a period partner 2 dissociates signal from partner 1 disappears. While the binding of partner 2 is absent for a given polynucleotide being sequenced, a partner 2 that is paired with partner 1 of an adjacent polynucleotide bins to that partner. The adjacent polynucleotide may be too closely spaced to the first polynucleotide for resolution to be achieved if partner 2 s are binding to the polynucleotides at the same time. However because there is a stochastic temporal aspect to the process, when the system is well tuned (in terms of concentration of binding partner 2 s, association and dissociation constants, temperature etc.), many molecules within a diffraction limited area can be resolved after the frames from a movie of typically 5-10,000 frames is analysed and the image reconstructed. Vertically through the stack of frames of the movie, it can be determined that there are many binding pair interactions per polynucleotides. In a typical experiment capturing 10,000 frames, 20 or substantially more binding pair interactions may occur, depending on how the system has been tuned. In some embodiments the a superesolution image is obtained from the multiple detection events via single molecule localization/stochastic optical reconstruction.

All the general nucleotide structures described in this invention can be applied to oligo-tagged nucleotides this includes the following class of nucleotides 1) Oligo tagged on base, acts as docking site for imager in DNA PAINT and is part of reversible virtual terminator 2) Oligo tagged on base acting as docking site for imager in DNA PAINT, with terminator at the 3' position 3) Oligo tagged on 3' position acting as a terminator and docking site for imager in DNA PAINT 4) Oligo tagged on 2' position acts as docking site for imager in DNA PAINT and is part of reversible virtual terminator Super-Resolution Sequencing Using Transiently Binding Nucleotides: Improving Accuracy by Querying the Base Multiple Times It should be borne in mind that compared with single molecule SbS, the next generation methods of sequencing which comprise library preparation and clonal amplification (e.g. Illumina sequencing) comprise two sets of polymerase copying reactions before the sequencing starts. One is during library preparation and the other is during cluster/polony/rolony amplification. These steps are susceptible to errors being introduced each time a polymerase makes a complementary strand. By contrast in the present invention where sequencing is being done on single molecules, without amplification, error due to polymerase misincorporation is limited to one possible occurrence, when the nucleotide is actually being incorporated during sequencing. Hence if the error rate of the polymerase is low, the sequencing error rate will also be low, e.g. 1 in 10, 0000; normally single molecule sequencing is also susceptible to error due to unfavorable dye photophysics (which typically lead to deletion errors) but the DNA PAINT approach overcomes this, because the signal is replenished multiple times. Even such low error can be overcome by some embodiments of the invention that include testing the nucleotide to be incorporated multiple times before incorporation occurs, as described in the following embodiments: In some embodiment the approach is to incorporate a reversible terminator (e.g. containing a modified 3' end) and then while the terminator is in place, adding fluorescent labeled nucleotides to interrogate the next base. The incorporation of the nucleotide complementary to the next base cannot be completed because the growing chain is terminated, nevertheless the correct base will associate for a longer period than the incorrect base and this difference can be detected. However, because of the blocked 3' end a covalent bond cannot be formed to consummate incorporation; the binding is transient and each correctly associating labeled nucleotide will be replaced by another. In this way the base in the target is interrogated multiple times by templating transient binding of complementary directly labeled nucleotides (in which the nucleotide is not cleavable), improving accuracy in the base call; if a wrong base binds it will dissociate faster than the correct base. Moreover because multiple binding events will be recorded a consensus can be obtained, which is likely to be in strong favor of the correct base, if enough events are detected (e.g. 10-20). The next step is to reverse termination, and then addition of the next reversible terminator followed again by transient binding of the fluorescent nucleotides. To reduce background fluorescence from the detectable fluorescent nucleotides are not incorporated, a lower concentration of nucleotides than normal may be used. Alternatively the reversible terminator may bear FRET partner, for example a donor or the polymerase can contain a FRET partner or the template can contain a nucleic acid stain or intercalating dye which is used as a FRET partner. A single wavelength donor can be used as a FRET partner for multiple acceptors used as distinct labels for each of the four fluorescent nucleotides. Because multiple FRET events due to multiple on/off binding of the fluorescent nucleotides are detected, the base calling due to the FRET is robust compared to when base calling relies on a single FRET event. The multiple on-off binding is catalyzed by Klenow fragment; other polymerases can alternatively be tested. The correct versus incorrect base binding to the interrogation position can be differentiated by slow and fast dissociation rates. Alternatively, if the nucleotides are fed in one type at a time, they need not be labeled; instead the polymerase can be labeled and its on-off dissociation can analyzed: slow dissociation of the polymerase if the correct base is transiently bound, high if the incorrect base is transiently bound. In one embodiment, which we shall call Sequencing by Anticipation, the base is initially called by the transient binding and subsequently the reversible terminator that is added also bears a base-specific label and confirms the base call (or the reversible terminator is added first and called and the transient nucleotide is added second). If the reversible terminator is negatively impacted by photophysics, the base can still be called on the basis of the subsequent transient binding nucleotides. Because the fluorescent transiently binding nucleotides are not consumed in the reaction, these can be shunted over the sample during the imaging step and then shunted back into a storage site on the flow cell and re-used in the next cycle. In some embodiments the termination is reversed by a physical trigger and is able to be conducted in a homogeneous manner.

In an alternative embodiment, unincorporable (e.g. β-X-2'-deoxynucleoside 5'-triphosphates (PCP-dNTPs)) transiently binding nucleotides are used and optionally the other nucleotide in this system is not a reversible terminator but a normal nucleotide whose further extension is halted by for example absence of divalent cation as described herein for closed complex sequencing.

In the case where the labeled nucleotide binds transiently the label does not need to be connected via cleavable linker. It can be a simply be a nucleotide modified on the base or any other compatible position. In this case the label can also be on the terminal phosphate position; in this case extra phosphates and the addition of manganese in the buffer promotes binding (Terminal phosphate labeled nucleotides: synthesis, applications, and linker effect on incorporation by DNA polymerases. Kumar S, Sood A, Wegener J, Finn P J, Nampalli S, Nelson J R, Sekher A, Mitsis P, Macklin J, Fuller C W. Nucleosides Nucleotides Nucleic Acids. 2005; 24 (5-7):401-8. Terminal phosphate-labeled nucleotides with improved substrate properties for homogeneous nucleic acid assays. Sood A, Kumar S, Nampalli S, Nelson J R, Macklin J, Fuller C W. J Am Chem Soc. 2005 Mar. 2; 127(8):2394-5.

The transient binding reaction can be conducted as a continuous real time reaction by providing a DNA repair reagents that can convert the reversible terminator back to a —OH. The conditions (e.g. concentration) for the DNA repair enzyme(s) are set so that the rate of reaction is low. This will enable the transient binding reagent to bind on and off multiple times before the termination is reversed. The DNA repair enzyme(s) are only capable of repairing the 3' end in the context of an extension complex, the reversible termination moiety of free nucleotides in solution are left intact. This system can be operated with two types of nucleotides as described, or with a single nucleotide type, for example a reversible terminator with a label on the terminal phosphate as well as a terminator on the 3' end (or a virtual terminator). When the nucleotide is incorporated the terminal phosphate label is a leaving group, leaving the chain extended by one nucleotide but terminated. Other terminal phosphate labeled 3' terminated nucleotides are able to then bind transiently multiple times at the 3' position but do not lead to a covalent linkage. Eventually the 3' end is repaired by the DNA repair enzyme(s) allowing a productive incorporation of a terminal phosphate labeled reversible terminator. The advantage of this real-time method over PacBio real-time sequencing is that there are several independent detection events for each nucleotide in the template. The apparent blinking in signal due to the on off binding, allows super-resolution of a dense lawn of molecules by PAINT. The fact that each base is queried multiple times leads to increase confidence in the accuracy of the base call. As an alternative to real-time DNA repair, this terminal phosphate labeled terminator approach can also be conducted in stepwise manner either by cleavage or repair of the terminator by cycling reagents or by clocking cleavage by light or generated-acid.

Multiple interrogation of the target base sequence can also be done by using a polymerase containing 3' to 5' exonuclease activity and tuning the concentration of nucleotides to be incorporated; so that before the extension proceeds to the next base the present base has been tested multiple times by exonuclease cleavage and reincorporation of a labeled base (e.g. directly labeled with a fluorophore). The labeled base may be a reversible terminator so that the sequencing proceeds one base at a time. The polymerase can be prevented from chewing back more than one nucleotide by providing a mixture of two types of nucleotides; the regular labeled sequencing nucleotides are supplemented with a phosphorothioate (e.g., a triphosphate analog with a phosphorothioate in place of the alpha-phosphate of the triphosphate chain, thereby preventing processive 3' to 5' exonuclease activity of polymerase) so that after several single base exonuclease excisions, a phosphorothiate nucleotide is incorporated, which cannot be removed by the exonuclease activity of the DNA polymerase. The several incorporations and removals, can include incorrect incorporations, but these will typically be outnumbered by the correct incorporations. The phosporothiate nucleotide does not need to bear a fluorophore and a cleavage cycle to remove a fluorophore is not needed. If the nucleotide does not bear a 3' terminator, no cleavage is needed. The modification on the base can act as the virtual terminator. Where termination is not complete and multiple nucleotides get incorporated, they can also be chewed back several times. This method can also be conducted in real time, when no cleavage mechanism is used. The ratio of labeled nucleotides to unlabeled phosphorothioate nucleotides determines the duration of each incorporation step. These methods, share with the DNA PAINT mechanisms described herein, the ability to be superesolved, because labels in a closely packed field do not fluoresce at exactly the same times.

Closed Systems

Key to some embodiments of this invention, is removal of background fluorescence (emanating directly from unreacted fluorescent nucleotides in solution, Raleigh scattering etc.). One means to do this is to separate the labeled target polynucleotides from unreacted fluors. The invention describes how to implement this in a number of ways. One is by removing the unreacted fluors (e.g. by washing) and another is by removing the labeled target polynucleotide from the location containing unreacted fluors. Another means to remove background is by using an evanescent field (e.g. created by total internal reflection) to limit excitation to close to a surface where the target polynucleotides are located. Finally, Raleigh scattering can be filtered from fluorescence by its time dependence. Raleigh scattering is short-lived and can be gated from the longer lifetime of fluorescence. In addition, the surfaces of the vessel, especially where the target polynucleotide is present should be non-sticky to the fluorescent labels and this can be achieved via passivation, e.g. lipid passivation.

Methods of this invention can be carried out in a mode where reaction components for the different steps of the reaction are provided at separate stages. The methods can also be carried out in a "homogeneous" mode, where all the components required for the reaction are provided in the reaction vessel from the start. Then cyclical electromagnetic modulation, for example for cleaving a linkage provides a clocking mechanism for shifting the sequence register.

Sequencing by Shunting Reagents within a Closed Vessel (See FIGS. 5 and 6)

In current Illumina SbS an excess of reagents are provided at each cycle. As not all of the reagents are used up at each cycle, a large amount of reagent is wasted, at a considerable cost. Further as enough solution for 250 lots of these reagents need to be stored if 250 cycles are to be conducted, sufficient space is needed on the instrument for storage. This necessitates a large instrument, which is not conducive to building an instrument suitable for clinical applications.

In some embodiment all the steps of the sequencing in the one pot reaction are conducted in a single container, but the container contains more than one reaction volume separated by an immiscible gaseous or liquid pocket, with each volume shuttled over the site of reaction at different steps of the reaction cycle. In some embodiments the container comprises a fluidic network and different reaction volumes are stored at different locations in the fluidic network. In some embodiments after the start of the sequencing process no new reagents are shuttled into the container or pot.

In some embodiments the one pot reaction contains a packet of reagents and this packet of reagents contains sub-packets of reagents and the packets (and thereby the sub-packets) are passed over the template polynucleotides multiple times (i.e. the solutions which contain reagents in excess are re-used.

In some embodiments, the one pot reaction contains multiple packets of reagents stored in the pot (FIG. 6), for example, if 100 sequencing cycles are to be conducted, 100 reagent packets are held in a fluidic circuit. Then each packed is delivered one after another. The packet for each cycle comprises a serial arrangement of sub-packets comprising reaction reagents or immiscible separation reagents or air gap: aqueous solutions separated by immiscible solutions or a gas (e.g. air, nitrogen or argon). The immiscible sub-packets may comprise an air pocket or may contain an immiscible fluid such as oil.

In some embodiments the compartments are aqueous in oil droplets or each aqueous packet is separated by an air gap or other medium, such that reagents for each packet cannot mix.

One sub-packet is for incorporation, one sub-packet for imaging buffer, one sub-packet for cleavage buffer; these sub-packets are interspersed with sub-packets containing wash buffers etc. The loop may start with priming solution or stretching solution.

In another embodiment the one pot reaction contains therein storage locations from which reagents are introduced and then removed again from the reaction site (the array of templates) and this is iterated to carry out the sequencing cycles. In this embodiment the reagents are not necessarily stored in packets, but certain components of the solution are moved to different locations in the vessel, for example where the reaction is occurring on surface bound templates on one of the surfaces of a flow cell, then some components of the reaction solution are moved to a surface not comprising the templates being sequenced. The components may be nucleotides, and these may be moved to prevent their terminator and or label being cleaved before the nucleotide has been incorporated.

The packets may be aqueous feeds into a fluidic channel punctuated by the immiscible pocket. The fluidic channel may be formed in tubing, capillary or it may be part of a monolithic fluidic structure such as a microfluidic device. Each packet in the channel is separated by an air pocket. One sequencing cycle comprises several different sequencing and wash reagents each separated from another via an air pocket. An air pocket also separates one cycle from the next. The different reagents and air pockets can be put into a continuous loop. In some cases the loop of reagents is repeated, with the same reagent sets contacting the elongation complex at every cycle. In other cases a large loop is provided where multiple iterations of the reagent sets are provided one set after the other, wherein each set comprises the reagents for one sequencing cycle, and each set contacts the elongation complex only once. For a 200 base read from the elongation complex, 200 reagent sets are needed.

In some embodiments different sub-packets are provided for each of the four bases which means the nucleotides do not need to be labeled (and a different component of the reaction is optionally labeled) or to be labeled differently if the order of the delivery of each of the four nucleotides is known. In some embodiments more than four nucleotides are delivered in separate sub-packet, where the nucleotides beyond the four provide a different a different functional purpose (see Transiently binding nucleotides section).

It should be noted that that a frequent changing of polymerizing reagent is justifiable if sequencing is done on a large number of molecules in parallel in small volumes. If the reactions are done in microfluidic channels the amount of reagents will be small and if a system of valves is incorporated onto a sequencing chip, the reagents, which will usually be provided in excess amounts, can be stored in designated chambers on the chip and re-used.

The system is not completely closed system, and resembles a Terrarium in that the system can be sealed or open to the atmosphere and allows heat and light to enter but does not require tending for an extended period, e.g., new reagents do not need to be added at every cycle.

Sequencing Using a Random Coil to Linear Chain Transition (See FIG. 7A and FIG. 7B)

In embodiments where one or more sequencing reactions are being conducted on a single long polynucleotide, such as 100 Kbp or longer length of genomic DNA, which would measure around 30 um in crystallographic length, different zones in the vessel over which the polynucleotide can be disposed can be used to carry out different steps of the reaction.

In some embodiments a DNA polymer can be spooled back and forth between a reaction area and a detection area to carry out the steps of a sequencing by synthesis cycle. The reaction area contains the reagents required for the reaction and detection area is devoid of the reaction reagents; in particular it is devoid of the fluorescently labeled nucleotides. When the incorporation and cleavage steps are conducted the target polynucleotide is bathed in a solution rich in incorporation and cleavage reagents. When the detection is conducted the target polynucleotide is bathed in a solution devoid of the incorporation cleavage reagents/medium.

In some embodiments the target polynucleotide is tethered to a planar surface from one of its ends. Without a flow or an electrophoretic potential, the polynucleotide forms a blob like random coil close to the site of attachment. When a flow or an electrophoretic effect is induced, the polynucleotide stretches out and the majority of the polynucleotide stretches away from the point of attachment. In some embodiments the labeled long strand is stretched beyond the area where nucleotides are flowed.

In an alternative embodiment during the biochemical steps the polynucleotide can be in a 3D area (e.g. microchannel of 100 um dimensions) where it is less confined. During the detection step, the polynucleotide is confined to a 1D or 2D area in the detection area. When the DNA is to be detected it is spooled into the detection area and when a reaction step is to be conducted it is spooled back into the reaction area.

Semi-Homogeneous Sequencing

In some embodiments of the present invention wash steps may be introduced between certain steps as required, and the invention is homogeneous for some steps and then becomes semi-homogeneous when fresh reagents are introduced again, after which steps may become homogeneous again. Particularly unreacted fluorescent nucleotides can be removed before the detection steps and after a cleavage reagent or cleavage buffer is introduced. In some embodiments some steps are semi-homogeneous in that introduced from a different location on the chip.

In some cases the homogeneous or one-pot sequencing reactions described in this invention are carried out multiple times. For example after starting the reaction with fresh reagents, five to ten cycles are conducted, after which reagents are refreshed for another five to ten cycles. Nevertheless the infrequent reagent exchange is different from the reagents that are exchanged in conventional sequencing by synthesis. In conventional sequencing by synthesis, reagents are exchanged between each step of sequencing, whereas in the present invention, a whole set of reagents comprising the homogeneous sequencing mix is exchanged in one go, so that all the steps of the sequencing cycle can be done with the same reaction mix.

In some embodiments even when cleavage is done photochemically, local generation of acid shunting of reagents from one location in the vessel to another is done, because the photocleavage process or acid cleavage process requires a specific chemical environment around the nucleotide in order to be efficient.

Homogeneous Sequencing without Energy Transfer

In some embodiments, especially where sequencing is conducted on a microarray spot or a clonally amplified spot of molecules (cluster/colonies, polonies, rolonies, and the like) where there is a high density of templates, the signal at the surface can be detected even in the presence of background signal. This is because signal becomes concentrated on the surface where the objective lens focuses. Out of focus signal is weak compared to the intensity of signal at the surface and the signal to noise ratio of the in-focus signal from the microarray or clonally amplified spot is sufficient for the label to be detected and the base to be called. Thus in some embodiments the signal from reacted binding pairs is distinguished over background from unreacted binding pairs due to its persistent or pronounced occurrence at a location on a surface. In some embodiments the separation of signal from noise occurs via applying an intensity threshold.

In some embodiments the templates are placed within a structure where signal is enhanced. Such a structure can be a zero-mode waveguide or a V-groove or a nanogroove, where illumination is confined or which comprises a plasmonic material or structure which enhances fluorescence.

The fluorescence of the labeled reactants floating in solution, distal from the signal enhancing structures is not enhanced and remain relatively dark compared to the reactants associating with the template and hence the single molecule signals proximal to the structures can be distinguished.

Nucleotides Coded with Quenchers

In some embodiments the reaction involves energy transfer (ET) pairs comprising a fluorescent donor and a quencher. In one such embodiment, the donor fluorophore is on the polymerase and the differently labeled nucleotides are differently labeled with different quencher groups or different numbers of the same quencher group. In one embodiment the donor and acceptor or the donor and quencher are present on the polymerase. The donor are located at different residues of the polymerase, such the finger opening closing action of the polymerase leads to a different levels of FRET signals or different levels of quenching. The four different nucleotides can be detected by adding them one at a time, and the FRET or quenching due to finger closing indicates how many nucleotides are added. In another embodiment all four nucleotide are added at the same time and the identity of the nucleotide is detected via the extent of FRET or quenching. In some embodiments the nucleotides are unlabeled. In some embodiments the nucleotides are reversible terminators.

In one embodiment the polymerase carries a fluorescent label and the reversible terminator nucleotides, depending whether they are A, C, G or T/U, carry different quenchers or different numbers of the same quencher (and hence different quenching potencies). When the reversible terminator quencher nucleotide is incorporated the decrease in fluorescence of the label on the polymerase is detected. The fluorescence at its decreased level is, in the majority of cases, sustained at an average level over time, allowing sufficient time to take enough data to be able to determine which quencher, and hence which nucleotide from A, C, G, T/U has been incorporated. For example, when the donor fluorophore is fluorescing at a level of 10 (arbitrary fluorescent units from software/camera) proximity of A quencher labeled nucleotide decreases fluorescence to 8+/−0.5, C decreases fluorescence to 6+/−0.5, G decreases fluorescence to 4+/−0.5 and T decreases fluorescence to 2+/−0.5. In some embodiments after such changes in fluorescence have been measured across an array, the termination is reversed allowing the next nucleotide to be incorporated. In some cases photophysics leads to photobleaching or dark states of the fluorescent labels, which means an incorporation event is not detected or there is ambiguity over which base has been incorporated. In some cases different molecules of an array of templates may bear donors on the polymerase which may have individual fluorescent character. For example their brightness of fluorescence may differ or their rate of blinking may differ. In some embodiments, rather than the decrease in fluorescence level from one absolute level range to another absolute level range, the change in fluorescence level range is detected. For example A decreases fluorescence 2×, C decreases fluorescence 3×, G 5× and T 10×.

The main advantage of coding the nucleotides with quenchers is that there is no background due to fluorescent nucleotides in solution. Also, only a single illumination wavelength is required for excitation. Further, there is no concern for the bleaching of labels on nucleotides.

In some cases the coding of the nucleotides is done by providing a mixture comprising quencher labels and fluorescence labels. For example, A is labeled with Quencher 1, C with Quencher 2, G with Fluorophore 1 and T with Fluorophore 2. Hence, to determine the nucleotide incorporated the degree of quenching is monitored as well as the shift in emission wavelength.

Quenched Nucleotides Coded by Fluorescence

The nucleotides may be in a non-fluorescent state, for example a quenched state, until they are incorporated, after which they fluoresce. This overcomes the problem of non-specific signal from unincorporated nucleotides, particularly those that stick to the slide or chip surface. This opens the way for using various types of simple slide surface chemistries. In addition, the combination of surfaces with low adsorption of fluorescent nucleotides with quencher nucleotides may be especially advantageous. As used herein, a quencher is a moiety which decreases the fluorescence emitted by the fluorescent label. This includes complete, and partial inhibition of the emission of the fluorescence. The degree of inhibition is not important as long as a change in fluorescence can be detected once the quencher is removed. The quencher can be attached to a terminal phosphate and the nucleotides may have one or more phosphates replaced with phosphorothioate or phosphoramidate. For example the nucleotide may be NH2-nucleotide or an α-S-nucleotide. The nucleotide may also be reversibly blocked at the 3' end. Although the term quenching is used here, instead of a quencher there may be a second dye attached and the first and second dyes may interact as FRET partners as donors and acceptors or electron transfer donors and acceptors (the acceptor could also be nucleotide base such as Guanine in this case).

Clocking of Sequencing Cycles

In the homogeneous embodiments of the invention a physical triggering or clocking mechanism is used to shift the detected incorporated nucleotide to the next nucleotide in the chain. In certain embodiments, the fluorophore is attached on the nucleotide via a photocleavable bond such as 2-nitrobenzyl and derivatives which have a high photocleavage efficiency by UV light. If this is attached at the 3' sugar then it acts as a reversible terminator. Also depending on the nature of the structure, it may also be attached at the nucleotide base or 2' end and function as a virtual reversible terminator; Lasergen (Stupi et al) have developed effective photocleavable virtual terminators which can be used with the methods of this invention. Alternatively the bond linking the terminator to the nucleotide may be acid cleavable, such as a PN bond or a 3' $ONH_2$ and photogeneratable acids (Gao et al J. AM CHEM. SOC vol. 120, 1998, pages 12698-126991998; Gao et al NUCLEIC ACIDS RES. vol. 29, no. 22, 15 Nov. 2001, pages 4744-502001) are used. In another embodiment, acids can be generated in a solution of electrolyte by an electrode to which a voltage is applied (Egeland et al ANAL CHEM. vol. 74, no. 7, 1 Apr. 2002, pages 1590-62002)).

In this scenario, the nucleotide is either quenched until it is incorporated or its fluorescence is only detectable over a threshold once it is in proximity of the surface or template and only one nucleotide is capable of being incorporated in one cycle. The fluorescence from the incorporated labeled nucleotide remains detectable (subject to photobleaching, which can be attenuated by provision of antioxidants) for a required period, before it is removed directly or indirectly by the action of light or a voltage applied to an electrode. Once the terminator is removed, the next nucleotide can be incorporated. Hence, this can be operated as a closed system, where the reagents required for the reaction are provided at the start, and the sequencing cycles are iterated or triggered/clocked by the action of physical signals.

Fluorescence Resonance Energy Transfer (FRET)

In fluorescence resonance energy transfer (FRET), a donor fluorophore molecule absorbs excitation energy and delivers this via non-radiative dipole-dipole interaction to a nearby acceptor fluorophore molecule in a distance-dependent manner (Stryer, L. and Haugland, R. P. 1967).

In one exemplary embodiment, the energy transfer moieties can be a FRET donor/acceptor pair. FRET is a distance-dependent radiationless transmission of excitation energy from a first moiety, the donor to a second, the acceptor. A change (ideally, on-off) in fluorescence from a donor or acceptor during a FRET event (e.g., increase or decrease in the signal) can indicate a change in distance between the donor and acceptor but it can also be sensitive to environment (pH, ionic strength, type of ion, oxygen saturation, and solvation polarity and orientation changes (Deuschle et al. 2005 Protein Science 14: 2304-2314; Smith et al. 2005 Protein Science 14:64-73

FRET efficiency is affected by quantum yield of the donor, the extinction coefficient of the acceptor, and the spectral overlap between donor and acceptor. High yield donors and high yield acceptors with good spectral overlap have been described (D. W. Piston and G. J. Kremers 2007 Trends Biochem. Sci. 32:407). Resonance energy transfer may be either an intermolecular or intramolecular event.

A nucleotide linked to a FRET acceptor may produce a detectable signal when it is in the close proximity of a polymerase linked to a FRET donor. Alternatively, a FRET donor and acceptor can both be attached to the same polymerase and a change in FRET signal is observed when there is conformational change in the enzyme, e.g. moving from fingers open to the fingers closed conformation (Santoso et al PNAS 2010; 107(2):715-20). The FRET donor and/or acceptor may be a fluorophore, luminophore, chemiluminophore, bioluminophore, or quencher (P. Selvin 1995 Methods Enzymol 246:300-334; C. G. dos Remedios 1995 J. Struct. Biol. 115:175-185; P. Wu and L. Brand 1994 Anal Biochem 218:1-13).

In some embodiments, the energy transfer moieties may not undergo FRET, but may undergo other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized (Laitala and Hemmila 2005 Anal. Chem. 77: 1483-1487).

Fluorescence resonance energy transfer can be used to cut out background fluorescence in single molecule experiments (Braslavsky et al PNAS 100, 2003, p 3960-42003). FRET in a DNA assay, termed iFRET has been introduced in which the donor dye is an DNA intercalating dye that is used to stain DNA (Howell W M et al. 2002). iFRET is reported to give fluorescence values that are 2.5 times greater than those obtained from the intercalating dye alone, and more than 40 times greater than those from conventional FRET. It is suggested that the reason for the difference may be that the iFRET system involves the channelling of an accumulation of energy from a chain of donor dye molecules (in contrast to a single donor in the FRET system) into the acceptor moiety, which is then able to re-emit energy unhindered. Double-strand, DNA-specific intercalating dye (e.g., SYBR Green I) has been used as a FRET donor, with a conventional FRET acceptor.

A FRET mechanism can be implemented with the SbS methods described in this invention. One embodiment of the present invention involves the detection at the single molecule level, using FRET between two or more FRET partners. The FRET partnership system comprises two or more partners each attached to a reaction component selected from the group comprising nucleotide, the template, the polymerizing agent or any other reagent involved in the polymerization reaction. Donor-acceptor fluorophore pairs are chosen so that the emission spectrum of the donor overlaps with the excitation spectrum of the acceptor; many different combinations of available fluorescent labels can be used.

In one preferred embodiment the FRET means of detection is utilized in a method wherein the labeled nucleotide is detected as it approaches the target DNA molecule. As the labeled nucleotide is brought into the proximity of the target polynucleotide during polymerization, the FRET reaction occurs between the label on the nucleotide and a FRET partner. This reaction can be detected. The FRET label is attached to the nucleotide through a terminal phosphate group. These phosphate groups are removed as the nucleotide is added during extension, so effectively the detection of the label, the extension, and the replacement of the labeled nucleotide with an unlabeled nucleotide occur almost simultaneously. When the nucleotide has been incorporated it is no longer labeled. The released pyrophosphate is free to diffuse out of FRET range. Preferably the repertoire of nucleotides, e.g. adenine, cytosine, guanine and thymine are each labeled in a way that their FRET signals can be distinguished from one another.

In another preferred embodiment FRET occurs between a DNA stain (e.g. an intercalating dye) bound to DNA and one or more FRET partners attached to another polymerization reaction component such as the nucleotide or polymerizing reagent. The bound DNA stain may act as FRET donor or acceptor. It is simple to add a DNA stain that incorporates at multiple positions along a template molecule so that it can contribute to a FRET reaction anywhere along the extending chain. One of the FRET partners may be the fluorescently labeled nucleotide, which is utilized to extend the polynucleotide being synthesized. The fluorescent label may be directly or indirectly attached to nucleotide, and it may be a nanoparticle. Preferably the DNA stain is not the first FRET Donor as this could lead to its wholesale photobleaching; although this can be minimized with judicious choice of antifade composition. Several DNA stains are available for staining double-stranded DNA and a few of these are also able to stain single-stranded DNAs relatively efficiently, e.g. SYBR Gold. However, many dyes can cause light-mediated strand breakage to occur; SYTOX Green is relatively resistant to this.

Alternatively, or additionally the FRET partner can be attached to the polymerase, for example the DNA polymerase. The FRET label may be in the form of a semiconductor nanocrystal/Quantum Dot or NanoDiamond, as these are resistant to photobleaching which is important when it is desirable to retain the same polymerase throughout synthesis.

Multiple FRET interactions can take place when the excitation and emission spectrum for FRET partners overlap. The first FRET partner is excited at one wavelength, and its emission wavelength overlaps with the excitation wavelength for the second FRET partner. The second FRET partner has an emission wavelength which overlaps with the excitation wavelength for a third FRET partner. In this way a chain of energy transfers can take place, when the FRET partners are within FRET range and the first donor has been excited. This can result in a large stokes shift e.g., large separation of excitation from emission. This allows the signal to be read at a wavelength far removed from to the original excitation wavelength, which is advantageous for eliminating bleed-through from the excitation source into the detection channel. Importantly, this method also ensures that all of the components (the target polynucleotide, the labeled nucleotide and the polymerase) are all in close proximity. In some instances an anti-stokes shift may be utilized. Howell et al describe a system in which the intercalating dye acts as donor. For example a single molecule system may involve SYBR green 1 as the donor and a Rox labeled nucleotide as the acceptor or YOYO-1 and Atto647N as acceptor. As Quantum Dots can be excited at various wavelengths, when they are used as the acceptor, donors emitting at various wavelengths can be used, e.g. YOYO-1, DAPI or SYBR gold. Alternatively, the incorporated fluorescent nucleotide or a fluorescent nanoparticle can act as the donor and an intercalating dye such as POPO-3 can be used as the acceptor (Nakayama et al 2003). The Quantum Dot can be excited at a wavelength far removed from the acceptor dye. The signal produced would be due to the localized excitation by the Quantum Dot of a few fluorescent dyes in its locality. Following detection of the FRET signals, an image of the polynucleotide polymer can be taken by exciting the DNA stain directly.

Because energy transfer to the acceptor is from a highly localized source, background fluorescence from anything beyond the FRET range, which is about 10 nm, does not contribute to background fluorescence. Hence, FRET enables reactions to be monitored continuously without the need for washing away of unbound fluorescent dyes or nanoparticles. This enables addition of more than one nucleotide to be detected in real-time. The system can be homogeneous in that all that is needed for the reaction can be placed in the reaction vessel at the start of synthesis. It is desirable to retain some form of agitation or mixing of the reaction solution to enable pyrophosphate to diffuse out of FRET range after it has been released.

In accordance with the above in one aspect the invention provides a method of sequencing a target polynucleotide, comprising the steps of:

(a) carrying out template derived polynucleotide synthesis utilizing a nucleotide labeled with a FRET partner and at least one other polymerization reaction component labeled with a FRET partner;

(b) determining the nucleotide incorporated by detecting FRET interactions; and (c) repeating steps (a) and (b).

Preferably this method is used to carry out real-time monitoring of the sequence. In some embodiments the FRET signals are super-resolved.

A nucleotide that may be temporarily resident within the FRET range of a polymerizing agent or a template molecule, may or may not get incorporated depending on whether it is the correctly matched nucleotide for the position in question. This temporary resident of the FRET locality must be distinguished from a nucleotide that is actually incorporated. This can be done by utilizing information gathered prior to the reaction about, for example, the longevity or strength of the FRET signal depending on whether it originates from a nucleotide temporarily resident within the FRET locality or a properly incorporated nucleotide. One way of measuring incorporation in the context of the present invention is by detecting quenching/de-quenching or preferably a wavelength shift with a FRET partner which occupies a different reaction component than the nucleotide itself. For example, the emission due to the FRET partner on the template may be modified by a FRET Partner on a phosphate of the nucleotide. When the nucleotide is incorporated and pyrophosphate is released, the FRET interaction is abolished and hence a fluorescent property of the FRET partner on the template is modified, e.g., it emits fluorescence at a shifted wavelength. The first donor in this scheme may be a Quantum Dot attached to the polymerizing agent and the whole process may be designed to have multiple FRET interactions which are able to be monitored in real time.

In various aspects, the invention includes a method of sequencing a target polynucleotide comprising:

(a) incorporating a plurality of intercalating dye molecules into the target polynucleotide;

(b) contacting the target polynucleotide with a solution comprising a polymerase and four types of differently labeled nucleotides, wherein each differently labeled nucleotide comprises the structure:

B-T-L, wherein B is a purine or pyrimidine base, T is a photocleavable terminator group chemically bound to B, and L is a label comprising a fluorescence resonance energy transfer (FRET) partner to the intercalating dye molecules;

(c) incorporating one of the differently labeled nucleotides, using the polymerase, into a chain complementary to the target polynucleotide;

(d) illuminating the target polynucleotide with a first wavelength of electromagnetic radiation, inducing FRET on the intercalating dye and incorporated differently labeled nucleotide partners, and thereby identifying the type of the differently labeled nucleotide incorporated;

(e) illuminating the target polynucleotide with a second wavelength of electromagnetic radiation, thereby removing the photocleavable terminator group; and (f) repeating steps (a)-(e) as a homogeneous or one pot reaction, thereby sequencing the target polynucleotide.

The energy transfer donor as described thus far in this invention is a DNA stain, comprising a intercalator dye or multiples thereof, a groove binding dye or multiples thereof, or any other energy transfer capable agent able to bind along the length of a DNA template in a substantially uniform manner.

The energy transfer donor may be a fluorescent molecule or a non-fluorescent molecule. The energy transfer donor may be excited by a certain wavelength of light or as the result of a chemical or biological reaction (chemiluminescent and bioluminescent).

In some embodiments, an essential characteristic of the sequencing scheme is that energy transfer donor must always be in the proximity of the leading edge of the growing chain so that energy transfer can detect each new nucleotide incorporation. The intercalator dye when preinserted into the DNA duplex (e.g., by prior incubation) or when available in solution to insert between the base pairs of the growing chain maintains its proximity to the newly incorporated nucleotide. As an alternative to providing the energy transfer donor as a DNA stain, this requirement can also be satisfied by having the energy transfer donor as a label that is attached to the polymerase binding agent (e.g. the polymerase). Such an agent due to its functional role in the synthesis retains its proximity to the newly incorporated nucleotide; if a first polymerase-binding agent becomes dissociated from the growing chain, another that may intercede and continue growing the chain can resume as the energy transfer donor.

In some embodiments the donor is an entity located on the polymerase. In other embodiments the donor is attached to an entity attached to the polymerase. In some embodiments the entity is a fluorescent nanoparticle (e.g. Quantum Dot). In some embodiments the entity is a fluorophore, chromophore or organic dye. In some embodiments the donor is a polypeptide fused to the polymerase, such as the Green Fluorescent Protein (GFP) or similar fluorescent protein.

Although the term FRET has been used above, in the methods of the invention the term can be replaced with Energy Transfer, as the mechanism may not necessarily involve Fluorescence, but more broadly be any Energy Transfer mechanism. Such Energy Transfer mechanisms may include Bioluminescence energy transfer, chemiluminescence energy transfer and other energy transfer methods that are not necessarily well defined. For example, energy transfer from intercalating dye interspersed along a DNA chain involves antennae like phenomena, which is distinct from single particle donor in FRET. Also, in addition to the transfer of energy, the transfer can be of electrons, particularly when the detection is of a quenching event. In some cases described in this invention, a homogeneous reaction is conducted without energy or electron transfer.

In one embodiment two energy transfer partners are attached to the polymerase, each of which may independently act as energy transfer donor to the label on the nucleotides and/or may transfer energy between each other. For example one location on an RNA polymerase can be labeled with Cy3B which when excited with green light can transfer energy to Atto 647N (Santoso et al PNAS 2010 107(2):715-20.).

In one embodiment the energy transfer donor is attached indirectly to the polymerase via attachment of a second protein to the polymerase. In one such embodiment the polymerase is labeled with biotin. The biotin can be attached to the protein in vitro via the same chemical methods described above for attachment of fluorescent labels. The biotin can also be attached via in vivo biotinylation (e.g. using AviTag, Genecopoeia). The biotin can also be attached via in vitro translation using the TNT Quick coupled transcription/translation/Transcend system (Promega) for example.

The divalent protein, streptavidin can then be attached to the polymerase via the streptavidin-biotin interaction. The streptavidin can be purchased with labels attached (Atto-tec) or labels can be added prior to attachment to the polymerase. The labeled streptavidins include Fluorescent nanoparticle-Streptavidin (Qdot streptavidin, Fluoropshere streptavidin; Life Technologies), Atto488-streptavidin (Atto-tec). Labels such as the ultra-bright Cy3b can be conjugated onto streptavidin. Neutravidin or avidin can be used instead of Streptavidin. Typically, energy transfer donors can become attached to the Streptavidin. The moieties on the polymerase to which the energy transfer donor is attached needs to be exposed on the surface of the protein and be accessible to the labelling chemistry. When the polymerase has multiple numbers of exposed moieties to be labeled, multiple labels can be added, or due to low reaction efficiency only a subset of the moieties may get labeled and it may be difficult to determine which locations have been labeled.

The reagents used in the present invention are specifically nanoparticles of 20 nm diameter and less or 40 nm diameter or less as significantly larger beads would be too bulky to efficiently carry out the required molecular processes. When nanoparticles are being used as a FRET donor, it is very important to ensure that they are well passivated to prevent non-specific binding of fluorescent nucleotides, which would give spurious FRET signals In one embodiment, the energy transfer donor moiety can be a nanoparticle or a fluorescent dye attached to the polymerizing agent. In some embodiments, the nanoparticle can have other or additional surface coatings which can modify the properties of the particle, for example, increasing or decreasing solubility in water or other solvents. The nanoparticle can be water dispersible. The nanoparticle can be a non-blinking nanoparticle. The nanoparticle can be photo-stable. The nanoparticle may be designed to not interfere with polymerase activity, including polymerase binding to the target molecule, polymerase binding to the nucleotide, polymerase catalysing nucleotide incorporation, or the polymerase cleaving the nucleotide and/or releasing the cleavage product.

In some embodiments the emission of the donor overlaps with the excitation spectrum of the acceptor. FIG. 1 shows how emission from an intercalator overlaps with four potential acceptors (each acceptor can exclusively label one of the four nucleotides). However, as the FRET donor can be very close to the acceptor, the degree of overlaps of the acceptor and donor do not need to be substantial. Energy transfer cassettes can be utilized where for example the intercalator dye donor or the label on the polymerase transfer energy to 2 distinct acceptor dyes. Each of the two distinct dyes is part of two distinct structures. One of the structures of the distinct dye comprises a further acceptor to which the distinct dye acts as an energy transfer relay; the other structure does not comprise the further acceptor. In this way there is not a need for the donor emission wavelength to overlap the excitation wavelengths of four distinct dyes, only two are needed, which each themselves either emit light or transfer it to a further acceptor which emits light. The dyes in the nucleotides of this invention can be attached via a linkage that can be photo-cleaved, as described elsewhere in this specification. Detection of energy transfer and calling bases: an energy transfer event can be detected both by detecting the increase of emission wavelength from the acceptor but also the decrease in emission wavelength from the donor. The coincidence (anti-correlation) of drop in donor emission with a concomitant increase in emission of one of the acceptors, confirms that a FRET event has occurred. This can be done by using optics that split the image on the basis of wavelength (e.g. the Quadview, Photometrics). Ideally each of the emission wavelengths is cleanly separated into one of the quadrant images. However, in most cases the emission of the acceptor dyes is although distinct, overlaps in some part of their emission spectra. Such closely spaced emission wavelengths can be distinguished by using the image splitting optics to generate a signature for each emitter. FIG. 1 shows a distinct signature for each of the fluorophores labelling A, C, G or T, based on the magnitude of the signal in each of the four detection channels.

Additional FRET techniques known in the art can be adapted and applied to the present invention. For example, the application by Beechem (application Ser. No. 14584829; Application Date: 29 Dec. 2014), which is incorporate herein by reference in its entirety.

Open-Closed Complex Sequencing

In another case some components may be associated with the surface not comprising the templates being sequenced. Such components may be released after a certain action has taken place on the templates. This action may be the formation of a closed complex of the polymerase with the target polynucleotide and the nucleotide, before incorporation has completed and resulted in a covalent attachment and this action is conducted in the absence of divalent cations. The imaging across the array is done of the labeled nucleotides attached to the polymerase complex, using the methods of this invention (e.g. FRET from intercalating dye to label on nucleotide). After imaging the divalent cations are released, so that they can move to the closed complex and allow incorporation to be completed. At the same time the nucleotides are moved away from the surface to limit the cases where more than one nucleotide is added per cycle.

In some embodiments movement of the divalent cations and the nucleotides is an active process. This can be done by shunting different solutions from one part of the vessel to another. It can also be done electrically. It is convenient that the divalent cations and the nucleotides bear opposite charges, so that by switching electrical bias from the top surface to the bottom surface promotes their movement in opposite directions. Upon completion of incorporation all but one of the phosphates on the nucleotide are part of the leaving group of the reaction. This enables the fluorescent label or the first binding pair to be provided on a phosphate that is not incorporated. This can be on the beta or gamma phosphate or when additional phosphates are provided in the nucleotide it can be on one of the additional phosphates. For example labeled quanta-, penta- and hexa-phosphate modified nucleotides are more easily handled by the polymerase. With the completion of incorporation, the divalent cations are then removed again, so that the closed complex can be formed again to sequence the next base. The movements of the divalent cations and nucleotides can be controlled by applying an electrical bias to the surfaces. For example where the templates being sequenced are on a first surface, movement is of divalent cations, to the negative potential on the second surface (not containing the templates being sequenced) away from the templates. The electrical biases can be classed as physical trigger for the purposes of this invention. The electrical trigger may be a switch of electrical bias, which causes certain chemical moieties to be attracted or repelled. In an alternative embodiment, the divalent cations are caged during formation of the closed complex and after detection of the incorporated base are uncaged by light. Chelators such as 1-(2-nitro-4,5-dimethoxyphenyl)-N,N,N',N'-tetrakis[(oxycarbonyl)methyl]-1,2-ethanediamine (DM-nitrophen) are known to sequester divalent cations such as $Mg^{2+}$ and release them upon exposure to UV light in the 350 nm range. Kaplan JH1, Ellis-Davies G C. Photolabile chelators for the rapid photorelease of divalent cations. Proc Natl Acad Sci USA. 1988 September; 85(17): 6571-5. This enables the reaction to be carried out in a homogeneous format and to be clocked to the next base by light.

Arrayed Primer Extension

In some embodiments the sequencing is done on an array of oligonucleotides, with a free 3' end tiling through a sequence of interest and just a single base extension is needed and also when a particular known mutations are to be targeted (Methods Mol Biol. 2008; 444:161-7. doi: 10.1007/978-1-59745-066-9_12); the single molecule implementation of this arrayed primer extension, according to the methods of this invention has particular advantages when a rare mutation in a background of wild type, as is often the case in cancer, needs to be addressed. This can be done on circulating tumour DNA. Here in each spot or feature of a microarray one can detect, with high confidence and count the frequency of each allelic variant at each targeted location in the nucleic acid. Depending of the number of molecules in the microarray feature or spot, a variant as rare as for example, 1 in 10,000 or 1 in 100,000 can be detected depending on the size of the spot and the density of the molecules within the spot; the superresolution aspects of this invention can be applied in the case of a standard microarray in which the DNA probe is relatively tightly packed; methods for making microarrays are described in DNA Microarrays: A practical approach Ed. M Schena, O U P, 1999).

Polymerases and Nucleotides

The Polymerase must be one that can tolerate the incorporation of a modified nucleotide. Different polymerases are able to tolerate different sites of labelling on the nucleotide. In the embodiment of this invention where the energy transfer acceptor and/or terminator is on the base, Klenow and 9° North and variants thereof can be suitably employed. In some embodiments 9° North is modified (sold commercially by NEB as Therminator). In the embodiment of this invention where energy transfer acceptor and/or terminator is on the 3' or 2' position of the sugar, 9° North variants with modifications at specific locations can be suitably employed. Suitable DNA polymerase from *Thermococcus* species 9° N-7 include mutants: 9° N (D141A/E143A/A485L) DNA Polymerase gene; 9° N (D141A/E143A/Y409V/A485L) DNA Polymerase gene; 9° N (D141A/E143A/L408S/Y409A/P410V) DNA Polymerase gene. In some embodiments the polymerase which is used is naturally or engineered to be highly processive and remains attached to the growing template through many cycles. In some other embodiments the polymerase is naturally or engineered to be non-processive, and is able to easily dissociate after adding one or a few nucleotides. Such a polymerase can act catalytically, in that once it dissociates from one growing complex it can attach onto another primed template and polymerize and thereby effect the addition of nucleotides to multiple growing chains.

In the case when the energy transfer donor is attached to or associated with the polymerase, the polymerase must be able to tolerate the attachment. In the case of attachment of streptavidin to which donors are appended, Klenow polymerase is able to tolerate the attachment, as are Phi29 polymerase and similar polymerases.

Screening of different labelling positions, linker type and length can be done determine the optimal orientation/flexibility in which the donor on the polymerase is placed so that it can best interact with the acceptor on the nucleotide. The distance between any site on the polymerase and the nucleotide being incorporated is typically close enough for robust FRET signal to be detected.

Quite often enzyme preparation have functionalities in addition to the one that is desired. For example, an enzyme may have an exonuclease as well as polymerase activity. Or the enzyme preparation may have a contaminating activity present. Measures may need to be taken to prevent adverse effects due to such non-desired activities. Commercially available DNA polymerases, such as Therminator, Klenow, Bst, Bsu and 9° N DNA polymerases, Taq (e.g. ampliTaq), Pol475 (Birebird Biomolecular) have been reported to work well with the reversible terminating nucleotides. Methods for engineering polymerases have resulted in good results and engineering mechanisms such as "conserved by difference" (Chen et al Proc. Natl. Acad. Sci. USA 107, 1948-1953) can be used to adapt polymerase to needs. TOPOTAQ (Fidelity systems) is resistant to common inhibitors of DNA polymerases, such as DNA stains such as SYBR green 1 and II and SYBR gold. Nucleotides may bear a terminator or be free from a terminator, in the latter case sequencing can be conducted in a continuous manner, by transient nucleotide binding or the closed complex approach can be used.

Polymerizing reagents include DNA polymerases, RNA polymerases, RNA transcriptases, reverse transcriptases, or ligases, as well as chemical reagents that enable template directed polymerization. Favorable polymerases include those based on 9° N polymerase (New England Biolabs). As used herein "polymerizing reagent" also includes molecules or complexes that are capable of enforcing high fidelity base pairing according to well defined rules, regardless of whether they catalyse the addition of a single nucleotide. They can be natural, such as those listed above, or artificial such as abzymes and ribozymes. The polymerizing reagent may comprise one or more chemical reagents. For example, template directed ligation can be mediated by chemical reactions (Xu et al, 2001; G. von Kiedrowski, 1986).

Differentially Labeled Nucleotides Comprising a Base, Terminator, and Label

In some embodiments, such as those that shunt reagents from one location in the vessel to another, the nucleotides may contain chemically cleavable reversible terminator groups at the 3' end such as 3'-O-azidomethy reversible terminator, 3'-O-allyl reversible terminator or 3'-ONH2 reversible terminator. In some embodiments the terminator may bear a fluorescent group or a binding partner. In other cases the label or binding partner may be at a separate location on the nucleotide. In addition the terminator may be a modification at another position on the nucleotide, which while does not chemically block extension, may inhibit extension. So while the 3'OH functional group is retained, structures on the base that hinder further extension after their incorporation, such nucleotides have been described by Lasergen, Genovoxx and Helicos and are termed Virtual Terminators. The Helicos nucleotides are available from SeqLL Inc (Woburn, Mass., USA) and comprise an efficient single molecule label (Atto647N) attached via a linker that contains a disulfide bond and a features that prevent the addition of more than one nucleotide per cycle. Base labeling is done at the following positions on the nucleotides at the 7-deaza position for dATP and dGTP and at the C5 position for dCTP and dUTP.

In some embodiments the linker contains negatively charged carboxy groups.

In some embodiments the label is super-resolution compatible (e.g. for STED-20 or STORM-17). In some embodiments the label is not a directly detectable label but is a binding partner, a Tag, to which a corresponding partner or anti-Tag which is detectable is able to bind (and is compatible with PAINT-17). In some embodiments the tag and anti-tag are oligonucleotides. In some embodiments the oligonucleotides are non-Watson Crick base pairs.

In some embodiments the label is directly attached to the nucleotide without a cleavable linker (for use in the transient binding strategy-19). This transiently binding nucleotide is unable to form a covalent linkage because the 3' of the extending chain is blocked by a reversible terminator. Alternatively in some embodiments such a nucleotide is transiently binding because its 5' is modified to prevent it forming a covalent linkage with the 3' end of the extending chain.

In some embodiments the nucleotide may be photoswitchable (Singer M I, Jäschke A J Am Chem Soc. 2010 Jun. 23; 132(24):8372-7. doi: 10.1021/ja1024782.

Virtual reversible terminator nucleotides with multiple fluorophores attached are available from Genovoxx and these can be used to increase the signal to noise and enables sequencing to be done with a simple illumination source and low cost camera. In some embodiments the label and/or virtual terminator can be attached at the 2' Sugar position. In embodiments where the label is attached to a terminal phosphate additional phosphates can be added to the nucleotide terminus to improve incorporation. In some embodiment, nucleotides bearing multiple binding sites for imager strands which bind on and off simultaneously, can give a very bright, long lasting signal, but without super-resolution. The imager binding sites can be contiguous or can be separated by a nucleotide sequence or linker. The intervening nucleotide sequences can be made double stranded prior to the imaging reaction. In some embodiments when the aim is not to do super-resolution imaging, the long-lived imager strands can be bound to the nucleotides before the nucleotides are incorporated.

Photocleavable Nucleotide Structures:

In various embodiments, at least one of the differentially labeled nucleotides comprises a structure/compound selected from this section (Differentially Labeled Nucleotides Comprising a Base, Terminator, and Label).

In one embodiment, a nucleotide and nucleoside compounds are provided comprising a deoxyribose or ribose sugar and a base, wherein the base is covalently linked to a photocleavable terminating, 2-nitrobenzyl group. The 2-nitrobenzyl group can be substituted with groups that increase termination of DNA synthesis as well as the rate of deprotection. In addition, the 2-nitrobenzyl group can be detectable by attaching a reporter group, such as a dye or a binding pair. The dye can be linked to 2-nitrobenzyl group by a bifunctional linker. Compounds according to the invention can be represented by the following formula:

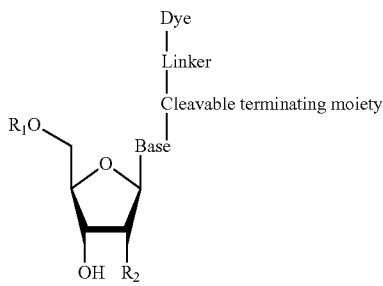

wherein $R_1$ is H, monophosphate, diphosphate or triphosphate, $R_2$ is H or OH, base is cytosine, uracil, thymine, adenine, or guanine, or naturally occurring derivatives thereof, cleavable terminating moiety is a group imparting polymerase termination properties to the compound, linker is a bifunctional group, and dye is a fluorophore.

Compounds according to the invention can be designed as fluorescent, photolabile reversible terminators useful in DNA synthesis sequencing. The compounds can be optimized reversible terminators, modified to have fast and efficient deprotection behaviour and good fluorescent properties in aqueous solutions.

In some embodiments 7-Deaza Purine nucleotide versions of the nucleotides described herein are used instead of adenine and/or guanine versions of the nucleotides.

The synthesis and use of labeled nucleotides including the structures disclosed are described, for example, in U.S. Pat. Nos. 8,889,860, 8,497,360, 8,361,727, 8,198,029, 8,148,503, 7,964,352, 7,897,737, and 7,893,227. The disclosure of these patents are incorporated herein by reference in their entirety. Version of structures described in these inventions and others described in the literature and patents for SbS can be tagged with fluorophores for some of the embodiments of this invention (including as FRET partners). Moreover, the SBS nucleotide structures can be modified with an oligonucleotide instead of a flour. Lightning terminators from Lasergen (as are those described by Ju and co-workers e.g. Li et a 1100(2):414-9 (2003)) are particularly favourable nucleotides for the methods of this invention as their light cleavability would support a homogenous reaction and the addition of a fluorescent label can be substituted with the addition of an oligonucleotide to carry out binding pair and DNA PAINT interactions. Nucleotides based on the dual modified structures described in Nature 456, 53-59 (2008) can also be used in the methods of this invention, as FRET partners (e.g. with YOYO-1 as donor) or by substituting the fluor with an oligonucleotide tag.

The nucleotides that are available are not always 100% pure. Sometimes the other bases contaminate. Therefore where a labeled reaction gives a particular signal which would be expected to be due to a particular base, in a minority of cases this might in fact be due to a different base. This needs to be taken into account in the error model.

Modified bases, even after cleavage leave molecular remnants or "scars" in the growing chain which hinder progression of the polymerase; recent photochemically cleavable nucleotides developed by Lasergen leave minimal scars.

The term "nucleotide" as used herein means any of the standard deoxyribonucleotides, or ribonucleotides. The nucleotide can be attached to a tag or label. Alternatively the nucleotides include any modified nucleotides or variations which pair with other bases according to defined rules, such as the Watson-Crick base pair rules.

The nucleotides typically comprise suitable sugar moieties, such as carbocyclic moieties (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284: 2118-2124; and U.S. Pat. No. 5,558,991). The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars. In one aspect, the 3'-position has a hydroxyl group, for strand/chain elongation. In another aspect the 3'-position has a reversible terminator attached and/or an energy transfer acceptor attached. In a further aspect the 2'-position has a reversible terminator attached and/or an energy transfer acceptor attached.

The nucleotides typically comprise a hetero cyclic base which includes substituted or unsubstituted nitrogen-containing parent heteroaromatic ring which is commonly found in nucleic acids, including naturally-occurring, substituted, modified, or engineered variants. The base is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, N6-Δ2-isopentenyladenine (6iA), N6-Δ2-isopentenyl-2-methylthioadenine (2 ms6iA), N6-methyladenine, guanine (G), isoguanine, N2-dimethylguanine (dmG), 7-methylguanine (7 mG), 2-thiopyrimidine, 6-thioguanine (6sG), hypoxanthine and 06-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, 04-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in: Practical Handbook of Biochemistry and Molecular Biology, pp. 385-394, CRC Press, Boca Raton, Fla., and the references cited therein.

The organic dye can be any dye compatible with emitting a detectable wavelength of light and which can be incorporated by the polymerase. The use of a single donor requires each of the distinct acceptors on each of the four bases to work as energy transfer acceptors partnered with the donor. This is used to call the identity of the base from the wavelength of the emitted light. It is possible to have four distinct dyes that respond to the donor. For example when the donor is YOYO-1 or Sytox Green intercalated into the target duplex, the acceptors can be Cy3/Cy3B, Alexa 594, Atto 647N and Cy5.5 or similar dyes in each of the wavelength ranges. Another example is when the donor is Cy3b attached to the polymerase and the acceptors are Cy634, AF647, AF676, and AF700. Alternatively, the 4 acceptors do not comprise dyes with 4 completely distinct wavelengths.

The cleavable bond can be cleaved following the detection of the presence or absence of the labeled nucleotide. The label can be attached in such a way that it blocks the incorporation of further nucleotides. This ensures that the only one labeled nucleotide is incorporated. Thus the cleavable label may have dual functionality, blocking the addition of more than one nucleotide, as well as reporting the identity of the nucleotide.

The cleavable bond can be cleaved by means of light (if it is photocleavable). A photocleavable 2-nitrobenzyl based linker at on the base as a photoreversible blocker/label has been described by Stupi et al (Angew. Chem. Int. Ed. 51:1-5 (2012)). If the cleavable bond is a disulphide bridge it can be cleaved using a mild reducing agent such as 2-Mercaptoethanol, (dithiothrietol) dithiothrietol (DTT) and Tris(2-carboxyethyl)phosphine hydrochloride TCEP. If the removable bond comprises a diol then it can be selectively cleaved using saturated aqueous NaIO4. If the removable bond is an amide or amineoxy ($ONH_2$) it can be cleaved by mild acid that can be generate as a photo-generated acid. The chemical treatment is preferably mild. For example, the phosphoramidate bonds formed within the resulting polynucleotides can be specifically cleaved with dilute acetic acid, for example 0.1M. In some instances measures are required to ensure that the extending primer remains complexed to the template after mild acid treatment. For example the primer may be covalently linked to the template or both primer and template may be linked to a surface, in intimate contact with each other.

There are two types of termination concepts. The first is as modification at 3' of the sugar that does not support chain extension. The second is the concept of the "virtual" terminator, where the termination is not chemical but is refractory towards further nucleotide addition, for example through steric hindrance.

Firebird offers triphosphates with a 3'-ONH2 reversible terminator and a diol linker carrying a free amino group, to which can be attached a fluor or other tag moiety. The diol is cleaved in seconds by aqueous periodate. Nucleotides with Labels attached to the 3' end can be incorporated (Hutter, D., et al labelled nucleoside triphosphates with reversibly terminating aminoalkoxyl groups. Nucleos. Nucleot. Nucl. Acids 29, 879-895 (2010)).

Some embodiments of the invention comprise a composition of nucleotide comprising a DNA nucleotide comprising, three or more phosphate groups, a sugar ring, each of the four bases A, C, G, T/U, a cleavable linker and an oligonucleotide tag attached via the cleavable linker. In some embodiments a separate terminator is provider on the 3' end of the sugar, In other embodiments the cleavable linker and oligonucleotide tag are of dimensions and structure that allow reversible termination. In some embodiments after cleavage the structure has less than 200 atoms attached to the base. In other embodiments it is less than 30.

Arrays and Templates

Template derived polynucleotide synthesis" as used herein means forming a polynucleotide molecule utilizing a polymerizing reagent that specifically incorporates nucleotides using the target nucleotide sequence as a template. The polymerizing reagent specifically incorporates nucleotides consistent with the well know Watson Crick base pairing rules to generate a complementary strand to the template The incorporation may be of nucleotide analogues, nucleotide mimics or other molecules which can be templated by a polynucleotide and in which pairing is by well-defined rules (Eckardt et al 2002; Czlapinski, et al, 2001). For example, high-fidelity templating of DNA base shape mimics without forming Watson Crick Bonds has been reported (Delaney et al, 2003). Vice versa, the template may be any molecule which can template polynucleotide synthesis.

The target polynucleotide and synthesized polynucleotide can each independently be strands of RNA or DNA. The DNA can be genomic DNA, or cDNA. The RNA can be mRNA, microRNA, lncRNA or genomic RNA, such as that from a virus.

The synthesis process can involve annealing a primer to the template polynucleotide. The primer can then be extended by template derived synthesis. The primer consists of 5-100 nucleotides, preferably 10-75, 15-65, 20-55, 25-50, or 30-45 nucleotides. The primer may be labeled. A primer may be made and then hybridized to the target polynucleotide. The primer may be composed of nucleotide analogues or mimics or any modification that improves its function as a primer. Alternatively nicks can be made in double stranded molecules using for example, Deoxyribonuclease 1 (DNAse 1), Nicking endonuclease, Nicking mutant of Cas9 or related protein coupled with a guide RNA. Synthesis, and thus sequencing can start at each nick site and the non-template strand become progressively displaced (in the case of strand displacing polymerases such as Phi29 and Bst 1) or chewed away (in the case polymerases with a 5' to 3' exonuclease activity such as Taq polymerase). Whether a nick seeds displacement synthesis in a sense or antisense strand is revealed by the direction of migration of the sequencing signal detected over many sequencing cycles. The strand and local sequence context of the nick is known when it is produced by a nicking endonuclease that cleaves only one strand of its recognition site. In a further alternative, a primer is generated by the polymerizing agent itself such as TthPrimPol polymerase as described in WO/2014/14039 which is incorporated herein in its entirety.

The template polynucleotide is preferably attached or tethered to a solution (e.g. solid surface or a gel). The template can be attached indirectly to a surface or via a polymerizing reagent, which is attached to the surface, or it can be captured by a capture probe/primer. The capture may be of a single stranded target or a cohesive termini or "sticky end" of a double stranded template. The capture may also be of a double stranded region by, for example, RecA mediated strand exchange or blunt ended ligation.

RNA promoters native to the template DNA can be used for RNA synthesis by RNA polymerase. Alternatively, extrinsic promoters for specific polymerases can be incorporated by being part of a capture probe or by transposon directed integration into sites along the polynucleotide. T7 and T3 RNA polymerase promoters are preferred extrinsic promoters.

The methods of this invention are preferably undertaken on surfaces because it is easier to organize and repeatedly monitor reactions on a surface than reactions freely diffusing in solution.

The term "array" as used herein relates to a spatial arrangement of two or more (typically thousands, millions, billions) template molecules on a surface that can be interrogated from one cycle to the next by their persistent localization address at specific 2-D coordinates.

The array can be a random array wherein the nucleotides are attached to the surface randomly. Alternatively the arrays can be spatially ordered. The nucleotides can be arranged in a grid pattern, with regular spacing between each nucleotide. The nucleotides can be located in a "spot" along with a plurality of other templates of the same sequence. Alternatively the arrays can comprise DNA clusters. Also the arrays can be composed of tandem copies of the same sequence within a single polymer as can be created by Rolling Circle Amplification (RCA) (Smirnov et al).

The polynucleotides can be attached directly or indirectly to the surface. For example an enzyme, such as a ligase or polymerase, utilized in the process can be attached to a solid surface. The enzyme binds the target polynucleotide, thus anchoring it to the solid surface.

Alternatively the polynucleotides can be captured by oligonucleotides which are attached to the surface. The capture can be by hybridization of a single stranded oligonucleotide to a single stranded target or a single stranded region of a double stranded target. Alternatively, the polynucleotide or the surface immobilized capture probe may comprise a sticky end or both may have a sticky end. The template and synthesized strand can be permanently linked to the surface by a ligation reaction. Alternatively the permanent fixing can be mediated by including a Psoralen moiety opposite a thymine residue and cross-linking with UV light.

The array is preferably formed in a flow cell. The array may be present within a fluidic or microfluidic conduit. The arrays may also be on the bottom of microtitre plate or on flat bottomed microfuge tubes. These preferably have a bottom composed of high optical quality material.

Molecules can be attached to a solid surface by a number of methods that are well known to the person skilled in the art (such as those described by Fodor et al SCIENCE vol. 251, 1991, page 767 (1991), Hegner et al (1993), or Finzi and Gelles (1995). Suitable methods of using oligonucleotides nucleotides to form an array, and attaching polynucleotides to an array are described in WO02/061126 and WO01/57248.

The surface is preferably glass, silica or a polymer such as PMDS, Cyclic Olefin, Polystyrene, or a Fluoropolymer. The substrate is preferably a glass slide, cover slip, silicon wafer, microfabricated chip or multi-well plate, such as a flat bottomed optical grade 96 well plate. The polynucleotides may be attached to material that coats the surface. For example aminosilane coated surfaces supplied by Corning Inc (USA) or Asper Biotech (Estonia) can be used. The polynucleotides may be attached to beads, particles, or structures such as nanobars or nanorods which may contribute to the generation or modulation of a FRET signal. The surface may be metalized with for example silver or gold particles to enhance a fluorescent or a Raman signal (Malicka Anal Biochem. vol. 315, no. 2, 15 Apr. 2003, pages 160-9 2003).

In addition, the surface or particles thereon may carry charge or be electrically biased or may be heated in order to control the sequencing process (Schifferli et al NATURE vol. 415, no. 6868, 10 Jan. 2002, pages 152-5-S, 2002). An electric field generated at the surface is a useful way for controlling the attraction and repulsion of nucleotides at the surface (Asanov et alAnal Chem. 70:1156-63 (1998); Sosnowski PNAS. 94:41119-231997 (1997)).

The arrays may be created on surfaces which are compatible with enzymatic reactions and have low absorption of fluorescent reaction components. The surface can be coated with agarose, polyacrylamide, sol-gel, polyelectrolyte multilayers, Bovine serum albumin/biotin/streptavidin coating or various types of polymer matrix. Hydrogel coated surfaces such as Slide H from Schott or CodeLink from Surmodics can be used.

Non-specific binding to surfaces can be reduced by treatment of surfaces with BSA or Caesin. Unlabeled nucleotides and various types of nucleic acids, such as yeast tRNA and salmon sperm DNA can be used for blocking surface. There are various commercial surface blockers such as Block-Aid ((ThermoFisher) available. It can also be achieved, particularly for certain nanoparticles by surface treatment with CsCl or $MgCl_2$ In some embodiments the molecules being detected are arrayed at high density and super-resolution methods are used to localize and resolve signals that are closer than can be resolved by standard diffraction limited optical methods. For a label that emits at 600 nm, the diffraction limit is in the range of 300 nm; the methods of the invention allow molecules that are between around 1 and 300 nm apart to be resolved as well as molecules that are further apart. Although the methods of the present invention are preferably carried out on a solid surface, they can also be carried out using other method for displaying polynucleotide. This includes nanoslitsm, nanochannels and nanopits (Cao et al 2002; Tegenfeldt et al Anal Bioanal Chem. vol. 378, no. 7, 2004, pages 1678-1692 2004; Reisner et al Proc Natl Acad Sci USA. 2009 Jan. 6; 106(1): 79-84) in which the molecules can be confined without then being attached to a surface, particularly when the polynucleotides are long. In some embodiments the polynucleotides can be displayed in a 2-D lattice such as a DNA origami structure. In this case the handles emanating from the origami can attach the polynucleotides to be sequenced. The nanometer-scale spacing that is possible with DNA Origami and other DNA nanostructures enables the maximum use of space under a given resolution. For example, if the resolution of imaging is 20 nm, then polynucleotides can be placed precisely 20 nm apart using an origami grid.

Primers

In a double stranded molecule or when a primer is annealed to a single stranded molecule, there are two 5' ends and two 3' ends. Measures need to be taken so that there is only the possibility of chain growth at a single 3' end or a single 5' end depending on mode of synthesis. Otherwise extension from a non-desired terminus may complicate the analysis of the desired termini. When the target is immobilized on a surface by one of the ends, this end no longer participates in extension. For example a polynucleotide template can be immobilized to a surface via its 3' end and so then the only 3' end available for extension is the 3' end of the primer. In other instances the template may be captured by an immobilized primer in which case the 3' end on the template polynucleotide needs to be inactivated. This can be done by for example by ligating a blocked oligonucleotide to the end or extending with a Terminyl transferase, using ddNTPs prior to annealing to the primer.

Templates

In some embodiments template strands can be attached to a suitable surface without them being modified. For example the ends of double stranded DNA can attached to a vinyl-silane surface in pH 5.5 0.5M MES buffer. Also poly RNA is able to attach to a surface coated with oligo d(T). In other embodiments the template is modified, for example by tailing using Terminyl Transferase can be used to tail a template polynucleotide with a homopolymer sequence (using a dNTP) to facilitate annealing to an appropriately designed primer (e.g. an oligo d(T)). Poly (A) Polymerase can also be used for adding As to RNA. Single stranded polynucleotides can form intramolecular structure which can obstruct the binding of a primer or the progression of a polymerase. Also sometimes the template can fold in such a way that non-contiguous sequences are juxtaposed, which can lead to error in sequencing. To avoid this, extension can be carried out with a thermostable enzyme at a relatively high temperatures at which the intramolecular interactions are short lived and unstable. For example, ligation or polymerase extension can be done at 65° C. Thermocycling can also be done which is particular useful for a ligation based approach. In addition certain polymerases are compatible with denaturants such as Urea and DMSO. In addition single strand binding proteins such as $E.\ coli$ single-strand binding protein (SSB) and T4 gene 32 protein can be added; these have been shown to facilitate polymerase action. If denaturants are added then the primer and template must be held by bonds that can withstand the denaturation steps. For example, the primer may comprise LNA which can form highly stable interactions. Alternatively they can be held together by bonds in addition to Watson-Crick bonds. For example, a covalent linkage or a streptavidin-biotin interaction, However, the problem of secondary structure can be prevented from occurring if the target is substantially or completely double stranded. This is the case if the primer extension is initiated from a nick. Strand displacement synthesis can be conducted by methods known in the art (e.g. Paez et al 2004).

In some embodiments the polynucleotides of the invention are rendered in a substantially non-globular form, are untangled, substantially elongated and preferentially fully elongated or stretched. Polynucleotides that are at least substantially elongated, enable multiple sequencing start sites to be created thereon, either by using DNAse 1 or nicking endoucnelase to create multiple 3' ends along the length of ds polynucleotide. If the polynucleotide is single stranded oligonucleoides bearing 3' ends can be bound at multiple locations along the length of polynucleotide. Preferably the elongated polynucleotides are aligned in a single direction on a flat surface, allowing signals from sequencing reactions, as described in this invention, along their length to be detected.

Polynucleotide Repair

A polynucleotide can become damaged during extraction, storage or preparation. Nicks and adducts can form in a native double stranded genomic DNA molecule. A DNA repair solution may be introduced before or after DNA is immobilized. Such repair solution may contain DNA endonuclease, kinases and other DNA modifying enzymes. Such repair solution may comprise polymerases and ligases. Such repair solution may be the pre-PCR kit form New England Biolabs (Ipswich, Mass., USA).

Capture

In some embodiments the target polynucleotide can bind by one of its ends t specific surfaces. For example a vinyl surface at pH5.5 can bind to the ends of double stranded DNA. If the polynucleotides are modified to contain biotin for example, they can be bound to streptavadin or neutraidin coated surfaces. This can be done by tailing the polynucleotide using terminal teransferase or poly (A) polymerase. Polynucletids can also be captured to a surface by DNA binding proteins attached to the surface. If a complete repertoire or specific set of single stranded oligonucleotide probes are arrayed or spread out onto a surface they can serve as capture probes for polynucleotides, in the latter case specific for targeted molecules. When the target is captured by sequence-specific single stranded oligonucleotides sequencing can immediately proceed in a targeted way and this can be done directly on a single strand of the native genomic DNA without prior processing or poly RNA.

The method of the present invention can be adapted to obtain RNA expression data, by counting the number of sequences of the same identity. Once a certain length of sequence information has been obtained, it can be used to identify the RNA species. Thus in one embodiment the target polynucleotide comprises mRNA. The mRNA can be hybridized to primers which are designed to hybridize to any mRNA molecule. For example, primers can be designed to hybridize to all sample mRNA species at a specific point in the mRNA primary structure. This point could be the polyadenylation signal, AAUAAA, the Poly A tail at the 3' end or at the 5' end or the cap structure at the 5' end or a specific sequence clamped onto the 5' or 3' end. Preferably the primers are attached to a solid surface, and more preferably form an array. The method can also be used to count other kinds of RNA such as long-non coding RNA (IncRNA) and microRNAs. In such methods a tag can be ligated onto the end of the RNA or homopolymer tail be (added via yeast Pol (A) polymerase) which hybridizes to the capture probe or the ends of the RNA can be captured directly.

In some embodiments the RNA is converted into cDNA first. In some embodiments the sequencing method can also be implemented directly on RNA, without first converting to cDNA. The nucleotides of this invention can be incorporated by polymerases such as reverse transcriptase and DNA Polymerase 1 (e.g. Klenow fragment) acting directly on an RNA template.

In some embodiments the RNA is tailed and attached directly to the surface. A primer is then annealed and synthesis proceeds. In other embodiments the RNA is tailed and the tail hybridizes to an oligo probe attached to the surface, said oligo also acts a primer for the synthesis. In other embodiments specific RNA are captured by sequence specific probes, which then also act as primers to sequence adjacent to the capture site.

Thus in one aspect the present invention provides a method of sequencing RNA comprising:

a) contacting probes designed to hybridize to RNA molecules within a sample under conditions whereby the RNA will hybridize to said probes;

b) disposing the complex on a surface; and c) sequencing said RNA utilizing the probes as primers, using a method as described herein.

Labels

The label can be a tag, such as an oligonucleotide that is indirectly detected. The label can also be dye or particle that is directly detected.

The label can be optically detectable tag such as a fluorescent tag. The fluorescent tag may be a dye molecule such as a fluorophore, for example the Cy dyes (Cy3, Cy3b and Cy5), ROX (carboxy-x-rhodamine), TAMRA (tetramethylrhodamine), Oregon Green®, Vistra Green™, Fluorescein, PicoGreen®, BODIPY® series and Texas Red®, the Alexa Dyes, the Atto Dyes, the Dyo dyes and the EVO dyes etc. Relevant fluorophores are commercially available, for example, from Atto-tech (Germany), Biotium (USA), GE (USA) or Thermofisher (USA). Labels can be differentiated on the basis of lifetime as well as wavelength of emission. Alternatively the label can be a tag which can be identified due to its physiochemical properties, e.g. electronic properties or an electric charge. Alternatively a Raman signal can be detected, for example Surface Enhanced Resonant Raman Scattering (SERRs) (Kneipp 1999; Zander 2002) can be implemented.

The label can also be a nanoparticle, or microsphere. The nanoparticles may be optically active. For examples SERS particles, PRPs (Plasmon Resonant Particles), Quantum Dots, or latex particles with embedded dye, such as Fluospheres and Transfluospheres (Molecular Probes). The label can be a reporter and/or a terminator label. A reporter is a label that functions to report the identity of the nucleotide that is incorporated. A terminator or blocker is a label that prevents the addition of more than one nucleotide until it is removed. In some cases fluorescence may be intrinsic to the nucleotide base; some base analogues have enhanced fluorescence. The fluorescence can be enhanced by proximity related effects with metals or plasmonic structures.

The label can be attached directly through a covalent bond to the nucleotide, or via a linkage. The linkage preferably comprises a cleavable bond, for example a photocleavable bond, or a bond which is cleavable by flowing in chemical reagents such as a mild chemical treatment, for example using a reducing agent to cleave a disulphide bridge or a weak acid to cleave an amide bond. The linkage can comprise a binding pair.

Also, the label and quencher may be selected from the group consisting of fluorophores, quenchers, shift reagents, spin labels, radioisotopes, and magnetic resonance contrast agents. The quencher is favorably a dark quencher including black hole quenchers.

The fluorescent label is any fluorescent label that is capable of being quenched which includes the fluorescent label, such as fluorophores mentioned elsewhere in this document. The fluorescence that is quenched may also emanate from a nanoparticle. The fluorescent label or fluorophore and quencher moiety may interact via a mechanism selected from the group consisting of fluorescence resonance energy transfer, an electron transfer quenching mechanism and a ground-state complex quenching mechanism.

Also the fluorescent label may be selected from the group consisting of optionally substituted pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, Texas reds, ATTO dyes, EVO Dyes, DYO Dyes, Alexa dyes and BODIPY dyes.

Also the quenching moiety is selected from the group consisting of optionally substituted phenyls, naphthyls, anthracenyls, benzothiazoles, benzoxazoles, or benzimidazoles, pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, dabcyls, nitrotyrosines, malachite greens, Texas reds, dinitrobenzenes, ATTO dyes, EVO Dyes, DYO Dyes, Alexa dyes and BODIPY dyes. DABCYL, BHQ1, BHQ2, QSY7, QSY9, QSY21, QSY35, ATTO540Q, ATTO580Q, ATTO612Q, DYQ660 and DYQ661, rhodamine, tetramethyl rhodamine, pyrene butyrate, eosine nitrotyrosine, ethidium, fluorescein, Malachite green, Texas Red, dinitrobenzene and trinitrobenzene.

The label can be optically detectable tag such as a fluorescent tag. The fluorescent tag may be a dye molecule such as a fluorophore, for example the Cy dyes (Cy3, Cy3b and Cy5), ROX (carboxy-x-rhodamine), TAMRA (tetramethylrhodamine), Oregon Green®, Vistra Green™, Fluorescein, PicoGreen®, BODIPY® series and Texas Red®, the Alexa Dyes, the Atto Dyes, the Dyo dyes and the EVO dyes etc. Relevant fluorophores are commercially available, for example, from Atto-tech (Germany), Biotium (USA), GE (USA) or Thermofisher (USA). Labels can be differentiated on the basis of lifetime as well as wavelength of emission. Alternatively the label can be a tag which can be identified due to its physiochemical properties, e.g. electronic properties or an electric charge. Alternatively a Raman signal can be detected, for example Surface Enhanced Resonant Raman Scattering (SERRs) (Kneipp 1999; Zander 2002) can be implemented.

The label can also be a nanoparticle, or microsphere. The nanoparticles may be optically active. For examples SERS particles, PRPs (Plasmon Resonant Particles), Quantum Dots, or latex particles with embedded dye, such as Fluospheres and Transfluospheres (Molecular Probes). The label can be a reporter and/or a terminator label. A reporter is a label that functions to report the identity of the nucleotide that is incorporated. A terminator or blocker is a label that prevents the addition of more than one nucleotide until it is removed. In some cases fluorescence may be intrinsic to the nucleotide base; some base analogues have enhanced fluorescence. The fluorescence can be enhanced by proximity related effects with metals or plasmonic structures.

The label can be attached directly through a covalent bond to the nucleotide, or via a linkage. The linkage preferably comprises a cleavable bond, for example a photocleavable bond, or a bond which is cleavable by flowing in chemical reagents such as a mild chemical treatment, for example using a reducing agent to cleave a disulphide bridge or a weak acid to cleave an amide bond. The linkage can comprise a binding pair.

Also, the label and quencher may be selected from the group consisting of fluorophores, quenchers, shift reagents, spin labels, radioisotopes, and magnetic resonance contrast agents. The quencher is favorably a dark quencher including black hole quenchers.

The fluorescent label is any fluorescent label that is capable of being quenched which includes the fluorescent label, such as fluorophores mentioned elsewhere in this document. The fluorescence that is quenched may also emanate from a nanoparticle. The fluorescent label or fluorophore and quencher moiety may interact via a mechanism selected from the group consisting of fluorescence resonance energy transfer, an electron transfer quenching mechanism and a ground-state complex quenching mechanism.

Also the fluorescent label may be selected from the group consisting of optionally substituted pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, Texas reds, ATTO dyes, EVO Dyes, DYO Dyes, Alexa dyes and BODIPY dyes.

Also the quenching moiety is selected from the group consisting of optionally substituted phenyls, naphthyls, anthracenyls, benzothiazoles, benzoxazoles, or benzimidazoles, pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, dabcyls, nitrotyrosines, malachite greens, Texas reds, dinitrobenzenes, ATTO dyes, EVO Dyes, DYO Dyes, Alexa dyes and BODIPY dyes. DABCYL, BHQ1, BHQ2, QSY7, QSY9, QSY21, QSY35, ATTO540Q, ATTO580Q, ATTO612Q, DYQ660 and DYQ661, rhodamine, tetramethyl rhodamine, pyrene butyrate, eosine nitrotyrosine, ethidium, fluorescein, Malachite green, Texas Red, dinitrobenzene and trinitrobenzene. The term "nanoparticle" as used herein means an individual particle which has a maximum dimension in any one direction of less than a micron. The nanoparticles of use in the present invention are preferably spherical, and/or preferably have a diameter of 20 nm or less. The nanoparticle can be a core/shell nanoparticle. The nanoparticle can include a core comprising semiconductor material(s). The core can include materials (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb. The nanoparticle can include at least one shell surrounding the core. The shell can include semiconductor material(s). The nanoparticle can include an inner shell and an outer shell. The shell can include materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb. In one embodiment, the nanoparticle comprises a core having CdSe. In another embodiment, the nanoparticle comprises an inner shell having CdS. In another embodiment, the nanoparticle comprises an outer shell having ZnS. The outermost surface of the core or shell can be coated with tightly associated ligands which are not removed by ordinary solvation. In some embodiments, the nanoparticle can have a layer of ligands on its surface which can further be cross-linked to each other The fluorescent nanoparticle can be a particle which has a large number of fluorophores embedded within or on its surface (e.g. latex particles). Alternatively, fluorescence emission or modulation may be an inherent property of the particle as is the case for semiconductor nanocrystals (Quantum Dot Corp., USA; Evident Technologies, USA), gold nanoparticles (Nanoprobes Inc., USA), plasmon resonant particles (PRPs) (Seashell Technologies, USA), Resonance light-scattering particles (RLP) or $TiO_2$ nanoparticles (Paunesku 2003). Depending upon their size and/or material composition, semiconductor nanocrystals emit in different regions of the electromagnetic spectrum, even when excited with the same wavelength. Special coating procedures are applied to stabilize them in solution and make possible their conjugation with different objects. The advantage of nanocrystals is their high brightness of emission, high stability against photobleaching and their narrow emission spectrums, which facilitates multi-plexing. Semiconductor nanocrystals, of various emission wavelengths, with surfaces coated with streptavidin or biotin are available from Quantum Dot Corp. The streptavidin-biotin interaction can be mediated in the vendor supplied incubation buffer or other commonly used buffers.

Nanoparticles can also be attached to a modified nucleotide via a thiol (sulfhydryl/mercaptan) group. Thiol groups can be attached to metals, in particular, gold. Alternatively, a linker can be used to attach the thiol to the nucleotide. The linker may contain a cleavable bond which is photocleavable or cleavable by a mild reducing agent. Several thiol moieties may branch off from a single nucleotide thus increasing the strength of interaction with the nanoparticle. Alternatively the nucleotide base may be labeled with an amino-allyl group.

Amine coated Quantum Dots are available from Quantum Dots Corp. (USA) and a kit is provided for linking them with biomolecules.

As an alternative to linking the nucleotide to a nanoparticle through a thiol group, the binding pair linkage system described above can be used. The nucleotides can be attached to one member of a binding pair (e.g. biotin) through a cleavable linker and the nanoparticle may be coated with the other half of the binding pair, e.g. streptavidin. A photocleavable-Biotin-NHS reagent is commercially available from AmberGen which can react with amine groups in the nucleotides. A SNHS—SS-BIOTIN is available from Uptima and Pierce Biotechnology (EZ-Link Sulfo-NHS—SS-Biotin) which can be attached to amines on DNA bases and is cleavable by a mild reducing agent.

Nanoparticles relevant to the invention can range in size from just a few nanometers in diameter to a few hundred nanometers. Although counter-intuitive imagers with nanoparticle labels on imagers are able to bind on and off at the rates useful for the PAINT methods of the invention. In addition polymerases and nucleotides to which nanoparticles are attached are able to participate in polynucleotide template-directed polymerization.

Fluidic System

In some embodiments of the invention the sequencing biochemistry is conducted in fluidic conduit or flow cell surfaces can be suitably presented, reagents can be loaded and optionally stored, so that samples can be loaded and transported to sites where cycles of sequencing biochemistry and imaging are carried out and optionally thermally and electrically controlled. The device contains macro interfaces for loading of samples. The device contains a suitable optically transparent area for imaging and a surface for coupling to the illumination and optionally cleavage source. The flow cell can be designed to be a good optical match to the objective lens bringing in the light source. The system may be designed to be valve free, or it may have a system of valves controlling the movement of fluids. For DIY implementation of the invention a simple flow cell can be constructed by sandwiching double-sided tape between a glass slide and a coverglass (typically type 1.5 and suitable for TIRF imaging). Alternatively the sticky slide system from Ibidi can be used. Reagents can be moved through these home-made set-ups, manually. Alternatively pressure driven flow or a syringe pump can be hooked up to the inlets and outlets of these devices.

Imaging Methods

The images of the polynucleotides are projected onto the array of a Charge-couple device (CCD) or CMOS camera, which enables a population of single molecules distributed 2-dimensionally on a surface to be imaged (digitized and stored in memory) simultaneously. The images stored in memory are then subjected to image analysis algorithms. These algorithms can distinguish signal from background, monitor changes in signal characteristics including intensity, and perform other signal processing functions. The memory and signal processing may be performed off-line on a computer, or in specialized digital signal processing (DSP) circuits controlled by a microprocessor.

Typically, wide-field illumination schemes may involve illumination with a lamp, LED, a defocused laser beam or by an evanescent field generated by Total Internal Reflection of a laser beam. The field that can be viewed is determined by the magnification of the objective, any magnification due to the C-mount and, the size and number of pixels of the CCD chip. Single molecule imaging can be done with a 20×, 40×60×, 100× or 150× objective and matched to a camera with an appropriate number of pixels. The larger the size of each pixel increases the amount of light that can be gathered. To view large regions of a slide, a large array camera can be used, for example 4-16 megapixels (larger pixel numbers are now found in consumer cameras), to view several $cm^2$ multiple images must be taken. A low noise high sensitivity camera is used to capture images. There are several camera models that can be used including Hamamatsu ImageEM, Andor iXon X3, Evolve (Photometrics) Cooled Micromax camera (Roper scientific) controlled by MetaMorph (Molecular Devices), NIS-Elements etc. The software can be run on a Dell Precision or Lenovo D30 with the latest processer and sufficient RAM for the image sizes being generated.

The integration of an focus holding or focus clamp capability within the procedure to maintain focus as the slide is translated, is useful especially when Total Internal Reflection Fluorescence microscopy (TIRF) is employed. Software can be used to control z movement for the purpose of autofocusing. To avoid photobleaching it is advisable to use a shutter (e.g. from Prior Scientific) to block off illumination while moving from one location to another. A controller can be used to control x-y stage, the filter wheels and shutter, (e.g. Prior Scientific ProScan).

A single molecule reader especially designed for genomics, using Time-Delay Integration was developed by Upper Austrian Research (Linz, Austria)) (Hess et al 2004), providing significant improvement of signal to noise and speed. In the case where Time-delayed Integration (TDI) imaging or a line scanner is used a continuous image strip is obtained (Hesse et al Single-molecule reader for high-throughput bioanalysis. Anal Chem. 2004 Oct. 1; 76(19):5960-4.). One embodiment of the invention comprises, reading at a fast speed so that multiple blinking/on-off binding events are captured on adjacent pixels, before the travel of the stage translates the imaging to the next shifted location on the surface. An algorithm is then used to extract that temporal information on adjacent pixels (say, 1000 pixels) and the spatial information which is obtained in the next batch of pixels (the next 100 pixels). The advantage of this approach is that a large area will be covered rapidly.

Total Internal Reflection Fluorescence Microscopy (TIRF)

TIRF enables very high contrast, low background images to be obtained, for example using off the shelf system for Objective style TIRF (such as those produced by Olympus, Leica, Zeiss or Nikon) to generate an exponentially decaying evanescent wave. Objective style TIRF can be used when the sample is on a thin cover slip. However, it is not compatible when the sample is on a microscope slide. For this either Prism type TIRF (AJ Lacey) or a condenser based TIRF using a high NA condenser (Olympus, Japan) must be used to create TIRF. An evanescent wave can also be created by focusing the laser beam into the edge of a slide or cover glass as well a using a structure such as a grating in the substrate. Although the above describes use of the system on an inverted microscope, an upright microscope can also be configured in an appropriate way, for example as described by Braslavsky et al (2003).

Multi-Color Single Molecule Imaging

When the sequencing strategy involves the sequential addition of each of the four nucleotides all labeled with a single fluorophore such as Cy3, then a single image is taken after each base addition. However, if each nucleotide is differentially labeled (e.g., each nucleotide type is labeled with a different fluorophore) and added simultaneously, then the signal from each of the different fluorophores needs to be distinguished. This can be done by taking four separate images by switching excitation/emission filters. Alternatively, an image (Wavelength) splitter such as the Dual View (Optical Insights, Santa Fe, N. Mex.) or W View (Hamamatsu, Japan) which direct the light through two separate bandpass filters with little loss of light between them, can be used for imaging two different wavelengths onto different portions of a CCD chip. Alternatively the light can be split into four wavelengths and sent to the four quadrants of a CCD chip (e.g., Quad view from Optical Insights). This obviates the need to switch filters using a filter wheel. A MetaMorph drop-in for single image dual or multi-emission optical splitters can also be employed. Image splitting can be used to monitor FRET.

Four fluorescent labels need to be used that can be properly distinguished from each other. Ideally crosstalk between one dye and another should be kept below about 30-40% in order to be able to adequately separate them via thresholding and software manipulations. One combination that is used is Fluorescein, Cy3, Texas Red and Cy5. Other combinations that are easier to separate include Fluorescein, Cy3, Cy5 and Cy7, or Coumarin, Fluorescein, Cy3 and Cy5, or dyes with similar wavelengths to the each of these. As there are several varieties of Quantum Dots available commercially with wavelengths ranging from 525 nm to 800 nm (Quantum Dot Corp, Palo Alto, USA), there are several combinations that can be differentiated. Chroma ScienTechnology are able to custom design filter combinations that can resolve these four colors. There are already commercial combinations available that can separate 4 wavelengths, e.g. the 8400 series Quad Filter Set with single band excitation filters for DAPI/FITC/TRITC/Cy5™ (Chroma Technology, Brattleboro USA).

It is advantageous to use a single wavelength as a light source and not have to use filters, both for the simplicity of the set-up and because there is inevitably some loss of light when filters are used. In some embodiments the four different labels are coded by repetitive on-off hybridization kinetics; four different binding pairs with different association-dissociation constants are used. In some embodiments the nucleotides are coded by fluorescence intensity. The nucleotides can be fluorescent intensity coded by having different number of non-self quenching fluors attached. The individual fluorophores typically need to be well separated in order not to quench and a rigid linker or a DNA nanostructure is a good way to achieve this. One alternative embodiment for coding by fluorescence intensity is to use dye variants that have similar emission spectra but their quantum yield or other measureable optical character differs, for example Cy3B (558/572) is substantially brighter (Quantum yield 0.67) than Cy3 (550/570) (Quantum yield 0.15) but have similar absorption/emission spectra. A 532 nm laser can be used to excite both dyes. Other dyes that can be used include Cy3.5 (591/604) which while has an upshifted excitation and emission spectra, will nonetheless be excited by the 532 nm laser but will emit weaker than Cy3 even though both have similar quantum yields, Cy3.5 is being excited by a sub-optimal wavelength. Atto 532 (532/553) has a quantum yield of 0.9 and would be expected to be the brightest as the 532 nm laser hits it at its sweet spot.

It is advantageous to use DNA PAINT in combination with such encoding, because, the multiple independent detection events, will enable the intensity be better determined.

Continuous and Multiplexed Imaging

Where real-time sequencing is carried out, the translation of sample with respect to camera may be too slow to detect each molecular event. Therefore a method for collecting single molecule data on a surface by taking images simultaneously with an array of detectors can be implemented. Alternatively, the sequencing steps can be controlled by photo-clocking as described above.

Beyond the Diffraction Limit of Light: Super-Resolution and Super-Localization

By conventional means the diffraction limit of light does not allow molecules that are closer than half the wavelength of emitted light to be distinguished as separate point sources of light. Near field methods such as the Near-field Scanning Optical Microscope (NSOM) can go well beyond the diffraction limit but are not easy to implement. However, there are several far-field approaches for sub-diffraction imaging.

Firstly, where the characteristic of an emitting object such as quantum dot or a dye are known, it is possible to use the point spread function of the dye to resolve two closely spaced signals. Secondly, there are a number of hardware approaches that have been described and are commercially available, these include scanning optical microscopy, 4 Pi, STED, and SIM. In the case of STED, specific compatible sets of fluorophores must be used. Thirdly it is possible to localize and resolve the signals by allowing them to photobleach, a stochastic process (J Biomed Opt. 2012 December; 17(12): 126008). Fourthly, if the photons emanating from neighbouring emitters can be identified, then it is possible to overcome the diffraction limit. This can be done when two closely spaced signals are emissions at different wavelength, according to which they can be separated.

A number of molecular approaches have also been described that involve single molecule localization and stochastic optical reconstruction which can be defined as the pinpointing of the location of molecules in a dense array when signals from the molecules of the array do not arise at the same time, their photons can be collected separately because they are temporally separated.

The steps of single-molecule-localization-based super-resolution imaging are: (i) taking a sub-diffraction limit density of molecules, (ii) enabling a subset of the molecule to emit light so a sparse array of signals are obtained such that they are optically resolvable by diffraction limited imaging, (iii) determination of the positions of these fluorophores with sub-diffraction-limit accuracy, and (iv) stochastically allowing a different subset of fluorophores to emit light, (v) Reconstructing a sub-diffraction-limit or nanometric resolution image from the positions determined for each of the light emitting molecules.

One such approach STORM (Sub-diffraction-limit imaging by stochastic optical reconstruction microscopy (STORM) M. J. Rust, M. Bates, X. Zhuang Nature Methods 3: 793-795 (2006) uses sequential activation and localization of individual fluorophores to achieve high spatial resolution. STORM and its variants (e.g. d-STORM) similar approaches (fluorescence) photoactivated localization microscopyand (F)PALM, can be used in certain embodiments of the invention and require the use of specific sets of compatible fluorophores, whose properties-photons per switching event, on/off duty cycle, photostability, and number of switching cycles, underlie the quality of images that can be obtained at super-resolution (Nat Methods. 2011 December; 8(12): 1027-1036). Stochastic optical reconstruction can be defined as the pinpointing of the location of molecules in a dense array when signals from the molecules of the array do not arise at the same time or are temporally separated. As well as resolution such methods can be used to precisely assign coordinates of localization of the signals.

Another superesolution method, PAINT can also be used in various embodiments of this invention. PAINT imaging appears to show blinking or photoswitching because the fluorophores (or other labels) persistently bind on and off from the nucleotide. The method preforms successive single molecule localizations.

This allows robust single molecule detection to become feasible: The labeling of the nucleotide does not suffer from 'dark' triplet states and photobleaching that are characteristic of single dyes, as the dye is continuously replenished. The continuous replenishment also means that no great effort is needed to constrain the illumination area to prevent photobleaching of incorporated dyes, a distinct benefit in regards making instruments lower cost. The persistent repetition of signal at template locations allows us to easily filter-out computationally, non-specific binding of the oligonucleotides. It also means that there are multiple data points from the same single molecules for each incorporation event, which improves base-calling accuracy.

In one PAINT approach, DNA PAINT, each of the four bases is labeled with a different oligo (binding partner 1) to which a complementary oligo (binding partner 2) transiently binds. Each of the four-nucleotide bases are associated with binding partner pairs of different sequence complements. In order to be differentiated the binding partner 2 associated with each of the four bases is distinguishable from the other. The element that makes them distinguishable can be a different wavelength emitting label (e.g. Atto 488, Cy3B, Alexa 594 and Atto 655/647N), labels with different lifetime or it can be that the different pairs are designed to have different on/off binding kinetics. The PAINT also has the advantage that the fact that fluorophores photobleach is not of concern because they are always replaced by fresh imager strands. Therefore the choice of fluorophore, the provision of antifade, redox system is not that important and a simpler optical system can be constructed, e.g. without an f-stop to prevent illumination of molecules that are not in the field of view of the camera, because illumination only bleaches labels that transiently come into the evanescent wave.

In DNA PAINT as described in this invention the readout during the imaging step is obtained as an aggregate of many on/off interactions of different fluor bearing binding partners so even if one fluor is photobleached or is in a dark state, the fluors on other imager binding partners that land on the binding partner linked to the nucleotide may not be photobleached or in a dark state. Binding partner 2 is variously referred to as Imager, Imager strand, detectable label, anti-tag, Imaging Tag).

When the target is single-stranded, for example when it is RNA, rolling circle amplicons, synthetic DNA or after double-stranded DNA has been wholly or partially denatured, there is the potential for the oligo tags or the anti-tag Imager strands in DNA PAINT to bind to the single strands, even where there is a partial match. Many of these cases of non-targeted binding can be distinguished in software by their different binding kinetics (faster off rate, for partial match). However, for a 9mer probe there is a chance that there will be several matches in the genome. One solution is to select the tag and anti-tag judiciously, for example by using sequences that have minimal matching to the genome. An alternative approach is to use non-canonical base-pairs or non-Watson Crick base pairs, such as those described by Benner et al (*Cold Spring Harb Perspect Biol.;* 8 (11). pii: a023770 (2016)). In one embodiment when the reaction is run in homogeneous mode with a thermophile enzyme, the oligonucleotide tag and anti-tag are modified to form more stable base pairs. For example, the tag is an LNA modified oligonucleotide or a PNA oligomer, to which at an elevated temperature the oligonucleotide anti-tag can still transiently bind but with an off rate slower and more detectable than binding to non-targeted DNA. Alternatively, a large proportion of the single stranded target can be made double stranded by complementary DNA synthesis to prevent binding of the anti-tag imager. When the incorporation of the oligo-tagged nucleotide is done at 650, there is little chance of the tag oligo binding to the template DNA molecules, because the low stability of the 9mer at the 55-72° temperature used with thermophile enzyme. There are no challenges to the DNA PAINT approach working smoothly when the double strands are the native form of genomic DNA. There are multiple means for carrying out a SbS reaction using polymerases that can work with dsDNA: strand displacing polymerases; polymerases with 5' to 3' exonuclease activity.

When the concentration of the fluorescently labeled oligonucleotide in solution is aptly tuned, the density of molecules detectable at any given moment is a sparse sub-set of the actual density of the molecules on the surface (FIG. 1); the full set of molecules is detected by taking a movie. Hence, the templates can be arrayed at a density that is too high to be resolved by standard (diffraction limited) methods but can be nanometrically localized and superresolved.

In some embodiments the PAINT technique is combined with the other aspects described above or elsewhere in this document. In some embodiments the pronounced or persistent PAINT signal at locations along the target polynucleotide is sufficient to distinguish the signal over background. The PAINT technique provides the background rejection without utilization of BRET, FRET or other proximity based signal enhancement methods, it only requires the persistent signals at locations on the focal plane or surface to be detected. In some embodiments signal proximity based signal enhancement such as FRET can be combined with PAINT, so that illumination with four separate lasers is not required and so that interference from imager background is reduced.

Drift can be caused by vibrational and thermal effects. In single molecule imaging measures need to be taken to minimize drift. Drift correction can be used. Algorithms are available for performing drift correction for single molecule localization. This can involve using fiduciary markers or operated without. The Drift correction methods described by Jungmann et al in WO 2015017586 Alcan be applied.

High-speed super-resolution: Although video imaging for typical single molecule localization experiments takes several minutes to hours, by tuning the laser power, using a high-speed camera (e.g. Photron FASTCAM) and engineer properties of labels such as Qdots, fluorescent latex particles (13), resonant light scattering particles (e.g. gold) or poly-labeled nano-scale DNA Origami so that sufficient photons can be collected per millisecond to enable super-resolution detection of the incorporated nucleotide within 10 seconds. This is a conservative estimate of speed achievable; Ueno et al achieved 1-2 nm precision for gold nanoparticles on a surface with just 9.1 microseconds (~100,000th of a second) temporal resolution using dark-field total internal reflection microscopy (14). With such an implementation taking the duration of movies will be similar to the exposure times used for imaging in current approaches.

Localization is easier to determine when the fluorophore emitting the signal remains close to the site of incorporation, therefore the length and degree of flexibility of the linker or bridge joining the wavelength emitting moiety (e.g. fluorophore) to the base must be constrained, i.e. it is better to have a short length and a stiff linker.

Image Analysis and Algorithms for Sequencing

Metamorph, ImageJ/Fiji and several other commercial or free software offer facilities for analysis of images.

There are two types of image reconstruction methods for super-resolution: the localization methods which provide an explicit list of position of molecules and the deconvolution methods which reconstructs a super-resolved image without explicit localization.

Several software programs exist for processing data for localizing single molecules, this includes a plug-in for ImageJ/Fiji, ThunderSTORM. Drift correction is usually of utmost importance for single molecule localization so the first step is drift correction and this is integrated into the localization software. Resources that compare the various single molecule localization are available (Sage et al. Quantitative evaluation of software packages for single-molecule localization microscopy Nature Methods bigwww.epfl.ch/smlm/software/).

Swift, An open-source platform for image processing and base calling for sequencing by synthesis images (originally developed for the Illuina platform) can be adapted for the data generated by the methods of this invention (Whiteford N, Skelly T, Curtis C, Ritchie M E, Lohr A, Zaranek A W, Abnizova I, Brown. Bioinformatics. 2009 Sep. 1; 25(17): 2194-9.). A number of assemblers are available for assembling genomes from short read data including Velvet, AllPATHS, ABySS, SUTTA, DISCOVAR etc. See Simpson J T1, Pop M. Annu Rev Genomics Hum Genet. 2015; 16:153-72. doi: 10.1146/annurev-genom-090314-050032. Epub 2015 Apr. 22.

The image processing and super-resolution image reconstruction is carried out in a central processing unit (CPU), multiple processor cores, a Field-programmable gate array (FPGA) a graphical processing unit (GPU), cluster computing and supercomputing.

The use of super-resolution methods have thus far focused on improved visualization of cellular structures, where the need is to obtain high-resolution pictures. For this the super-resolution data collected has to be somewhat exacting and the burden on the imaging set-up is high (e.g. typically an optical isolation table is used). However, the need in sequencing is much less severe, just a yes or no answer is needed: Is signal corresponding to one of the four bases present at a particular distinct location; such a location can be determined by selecting for certain characteristics (e.g. presence of only one of the four colours in each image) vertically through the stack of images in the movie. Consequently the data collecting can be less exacting, as the goal is not to obtain a beautiful picture but to know whether a particular signal can be attributed to a particular location with some degree of confidence; these parameters can be refined as sequencing data is obtained; the sequencing data can train the base calling algorithms. Such a vertical analysis of the stack of images in a movie has other benefits too, for example it can allow one to filter out spurious signals: If a signal does not correlate to signals in a series at that location or not abide by certain parameters seen in the stack of images (e.g. more than one colour, suggesting more than one molecule in the nanometric location) it can be filtered out. Also signal processing algorithms can be used to extract signal from noisy images.

Complete System

The complete system for implementation of the methods of this invention comprises: a conduit or flow cell into which sample molecules are loaded and into which the reagents of the method pass into (and optionally pass through); the reagents described in this invention including polymerase enzymes, nucleotides, labels, oligonucleotides and buffer; an instrument comprising a detection/imaging component (laser, fiber optic scrambler, prism, objective lens, filters, mirrors etc.); a temperature control device (e.g. peltier device); pumps or pressure control device to move fluids, electrical connectivity for controlling polynucleotides or electrochemistry; physical signal generator including for example a UV light source for photocleavage; one or more computer processor, computer memory; computer software for instrument and process control, single molecule localization, image processing, base calling sequence assembling, data display, user interface; standard operating procedures.

BRIEF DESCRIPTION OF FIGURES

FIG. 7A and FIG. 7B: Stretching target polynucleotides away from flowstream comprising labeled nucleotides. (FIG. 7A) Electrophoretic flow is turned off, target is random coiled from attachment point and is in the flowstream of the nucleotides; (FIG. 7B) Electrophoretic flow is turned on, and the major part of the target is spooled out and stretched away from point of attachment and away from the flowstream of nucleotides. Hence the elongated polynucleotide can be visualized without interference from background fluorescence due to the fluorescent nucleotides which are largely confined to the attachment point of the target polynucleotide.

(FIG. 10A) Emission Spectra of YOYO-1 intercalator dye overlaps with excitation spectra of 4 fluorescent acceptor dyes (FIG. 10B) Energy transfer cassette-YOYO-1 acts as donor to the first dye on the nucleotide, which transfers energy to the second dye on the nucleotide.

(FIG. 11A) Filters centered on emission spectra of individual dyes; (FIG. 11B) Signatures-histograms show pattern of intensities for each individual dye detected across the filter sets. The ratios between signal in the four emission bandpasses, robustly reveals the identity of the dye. The on/off binding of the imagers can allow super-resolution reconstruction of the image.

FIG. 14: 4% agarose gel showing incorporation oligo-tagged nucleotide into self-priming hairpin and cleavage of oligo-tag. The structure of the self-priming hairpin is shown.

FIG. 21 presents a list of docking sequences for partner 1 and imager sequences for partner 2. Set of four sequence pairs can be selected to cover the four nucleobases.

EXAMPLES

It should be borne in mind that the following examples can be further optimized and the composition and concentrations of reagents used can be adjusted by those skilled in the art. Additional components may be added as known in the art and as exemplified in the patents and publications referenced in this document. As many of the required procedures are standard molecular biology procedures that lab manual, Sam brook and Russell, Molecular Cloning A laboratory Manual, CSL Press (www.Molecular Cloning.com) can be consulted. Also Eckstein, editor, Oligonucleotides and Analogues: A Practical Approach (IRL Press, Oxford, 1991) and M. J. Gait (ed.), 1984, Oligonucleotide Synthesis; B. D. Hams & S. J. Higgins (eds.) can be consulted for DNA synthesis. The following three handbooks provide useful practical information: Handbook of Fluorescent Probes (Molecular Probes, www.probes.com); Handbook of Optical Filters for Fluorescence Microscopy (www.chroma.com); Single-Molecule Techniques: A Laboratory Manual, Edited by Paul R. Selvin, University of Illinois, Urbana Champaign; Taekjip Ha, University of Illinois, Urbana-Champaign; Focus on Single Molecule Analysis, Nature Methods, June 2008 Volume 5, No 6. Also see Hermanson, G T Bioconjugate Chemistry for conjugation stratifies of tags to nucleotides and polymerizing agents.

There is a need to ensure that the reagents used are as pure as possible. This is particularly the case for nucleotides and oligonucleotides used in the invention.

The embodiments of the invention and technical details provided below can be varied by the skilled artisan and can be tested and systematically optimized without undue experimentation or re-invention. It is envisaged that aspects described for one embodiment of the invention can be used for another embodiment of the invention, as a person skilled in the art may choose.

Nucleic Acid Extraction into the Flow Cell

Nucleic acids can be extracted by methods known to those skilled in the art including using various kits that are available on the market. The extraction can also be done inside the fluidic system by loading cells into the system and trapping the cells in structured areas inside the flow cell before flowing lysis reagents such as proteases etc. are added. The extracted DNA can be sheared or enzymatically digested in the flow cell and captured for sequencing inside the flow cell. Nucleic acids from single cells can be extracted as described in van Strijp et al Scientific Reports 2017 or Marie et al BioXriv 2017.

Sequencing in a Closed System Using Illumina Reagents

Various Illumina SBS kits (e.g., TrusSeq SBS Kit) can be used for sequencing with reagent addition and imaging in the following order: Universal Sequencing Buffer; Incorporation Mastermix; Universal Sequencing Buffer; Wash Buffer; Universal Scan Mix; Cleavage Reagent Mix; Cleavage Wash Mix.

Figure 1:
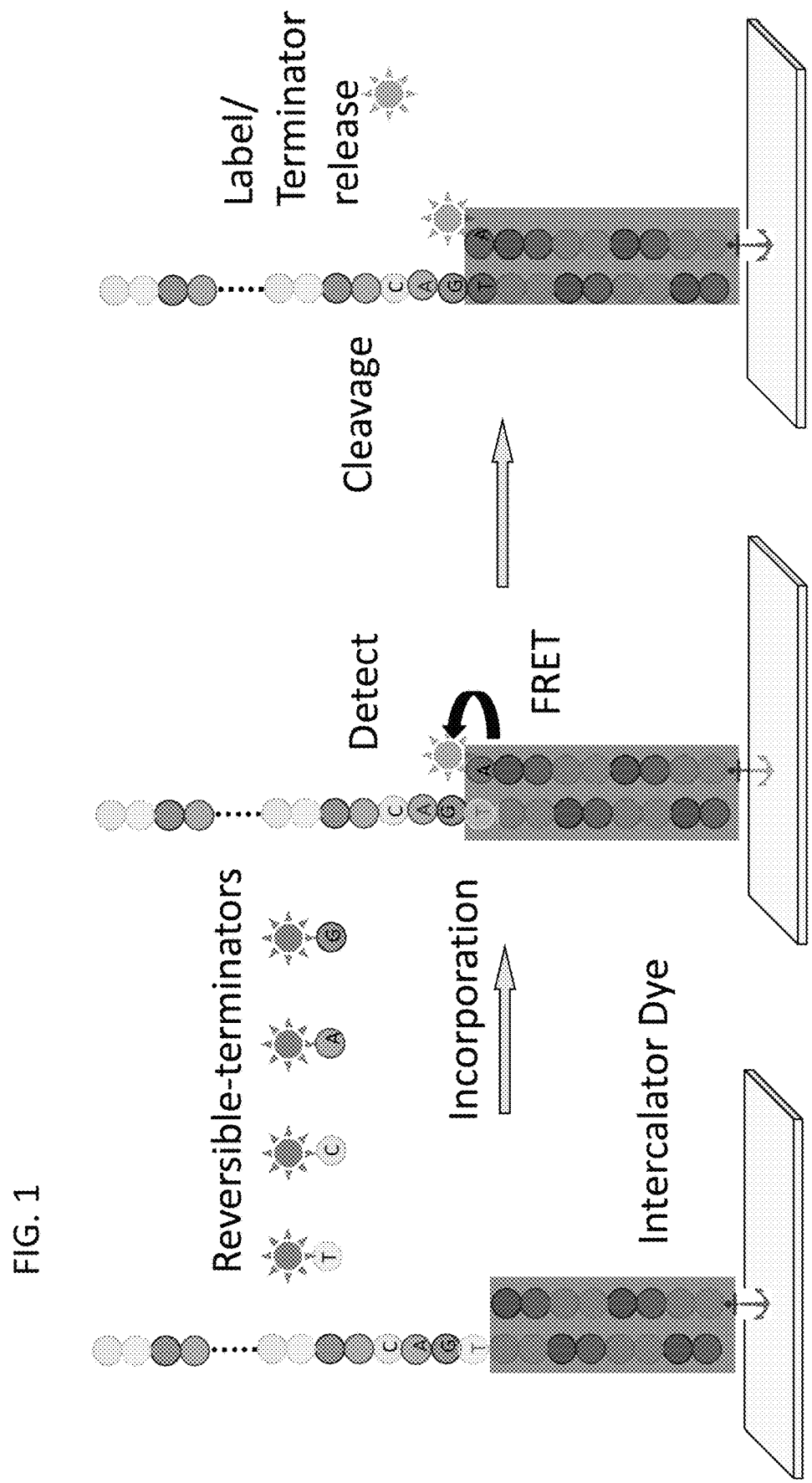
FIG. 1: Sequencing by Synthesis using Intercalating dyes as FRET partners. Sequencing using Cyclic Reversible Termination (CRT) with Fluorescence Resonance Energy Transfer (FRET) from Intercalator Dyes as donors to distinct acceptors on each of the four nucleotides. The cleavage can be through a homogeneous mechanism.
Figure 2:
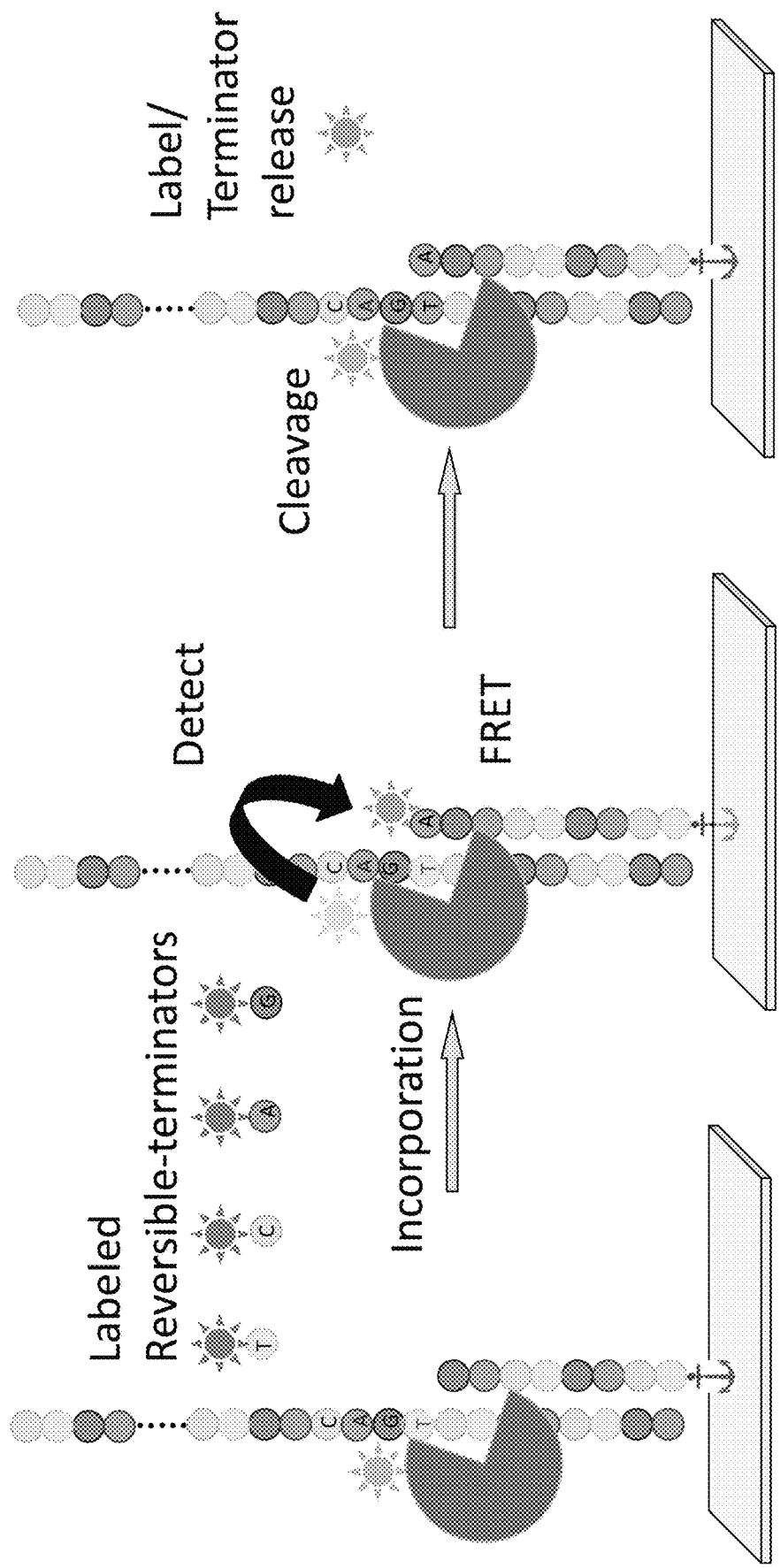
FIG. 2: Sequencing by Synthesis using label(s) on the polymerase as FRET partner(s). Sequencing using Cyclic Reversible Termination (CRT) with Fluorescence Resonance Energy Transfer (FRET) from label(s) associated with the polymerase as donors to distinct acceptors on each of the four nucleotides. The cleavage can be through a homogeneous mechanism.
Figure 3:
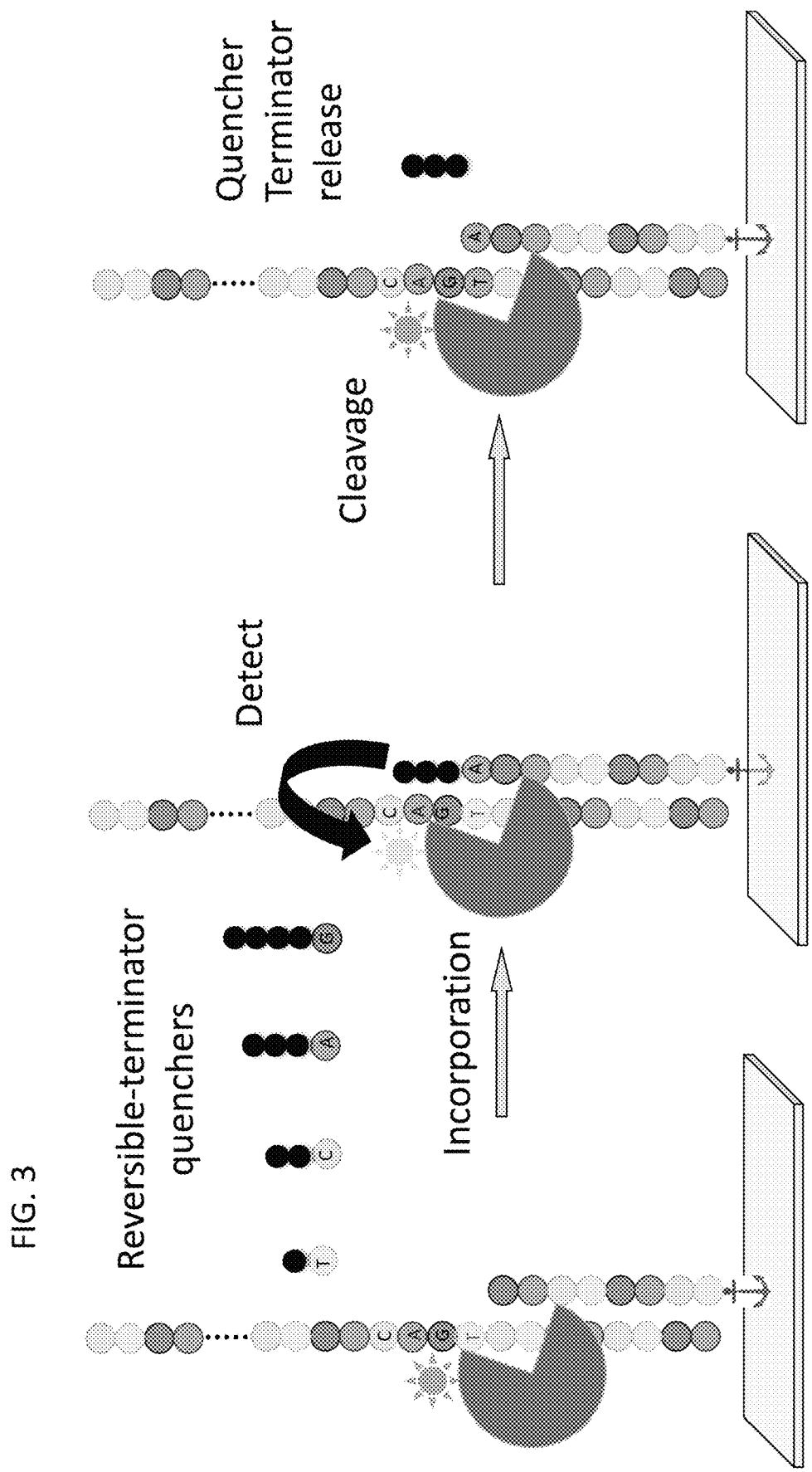
FIG. 3: Sequencing by Synthesis using Quenchers. Sequencing using Cyclic Reversible Termination (CRT) with Fluorescence Quenching of label(s) associated with the polymerase by distinct dark quencher configuration on each of the four nucleotides. The cleavage can be through a homogeneous mechanism.
Figure 4:
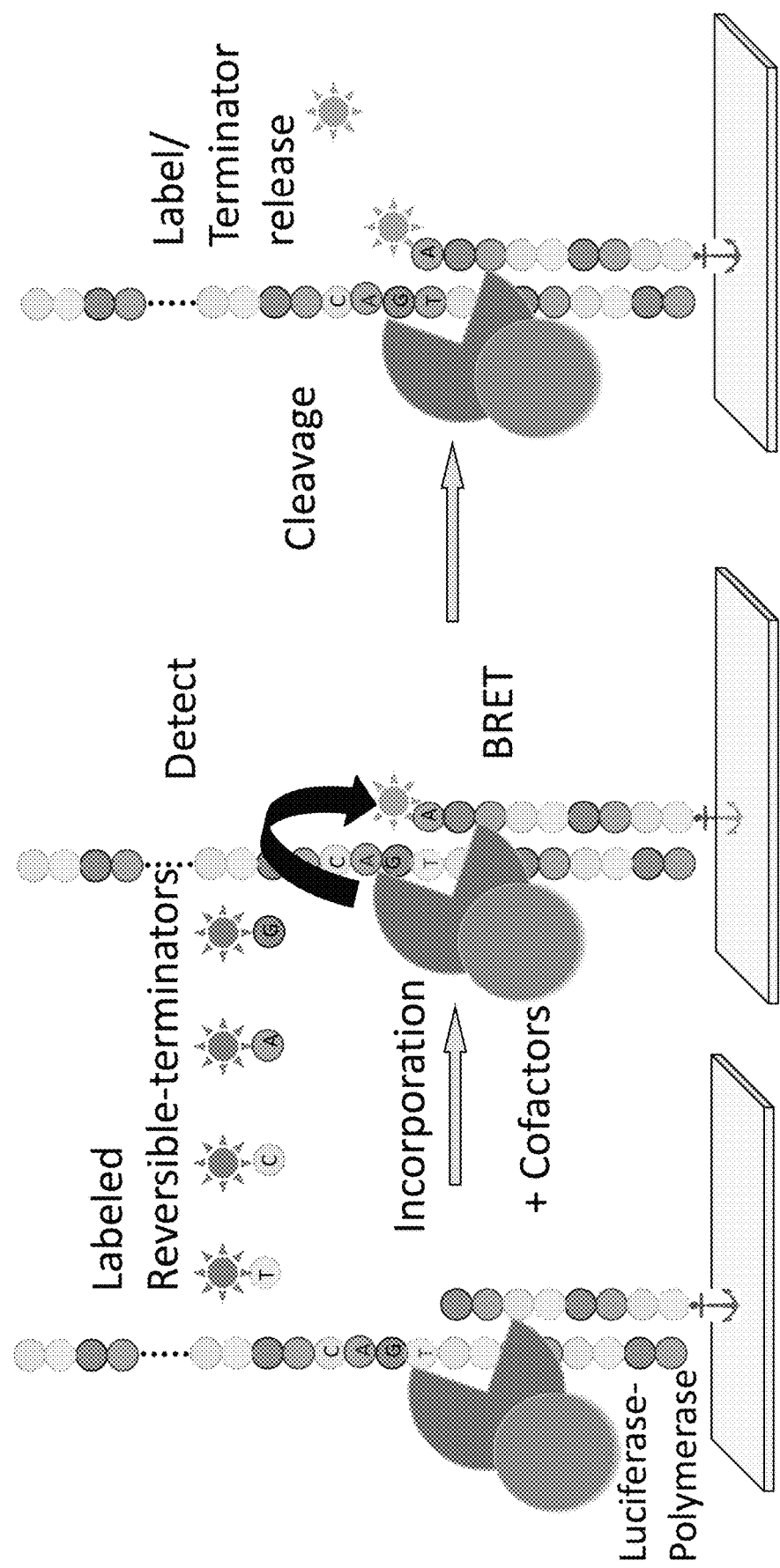
FIG. 4: Sequencing by Synthesis using BRET. Sequencing using Cyclic Reversible Termination (CRT) with Bioluminescence Resonance Energy Transfer (BRET) from a Luciferin associated with the polymerase as donor to distinct acceptors on each of the four nucleotides in the presence of co-factors required for bioluminescence. The cleavage can be through a homogeneous mechanism.
Figure 5:
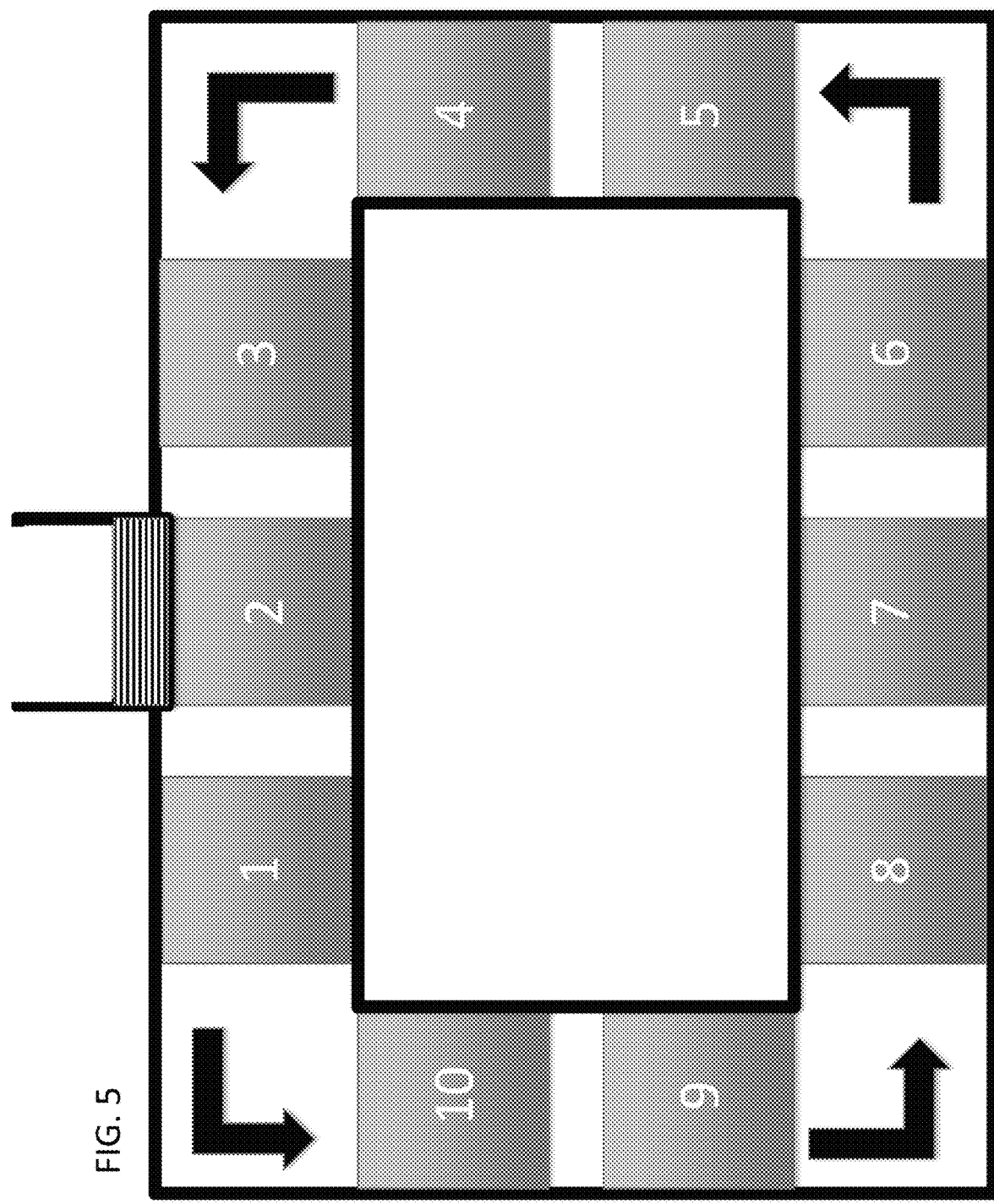
FIG. 5: Repetitively shunting of a packet of sequencing reagents over target templates. The schematic shows the circulation of a reagent packet (comprising sub-packets) over a channel containing the target polynucleotides; this is repeated for each sequencing cycle. The top center shows the port used to bring in the reagent packet is sealed, so that the packet can circulate as a closed system. All parts of the channel are exposed to the packet multiple number of times according to the number of cycles to be conducted. Each packet is used multiple times.
Figure 6:
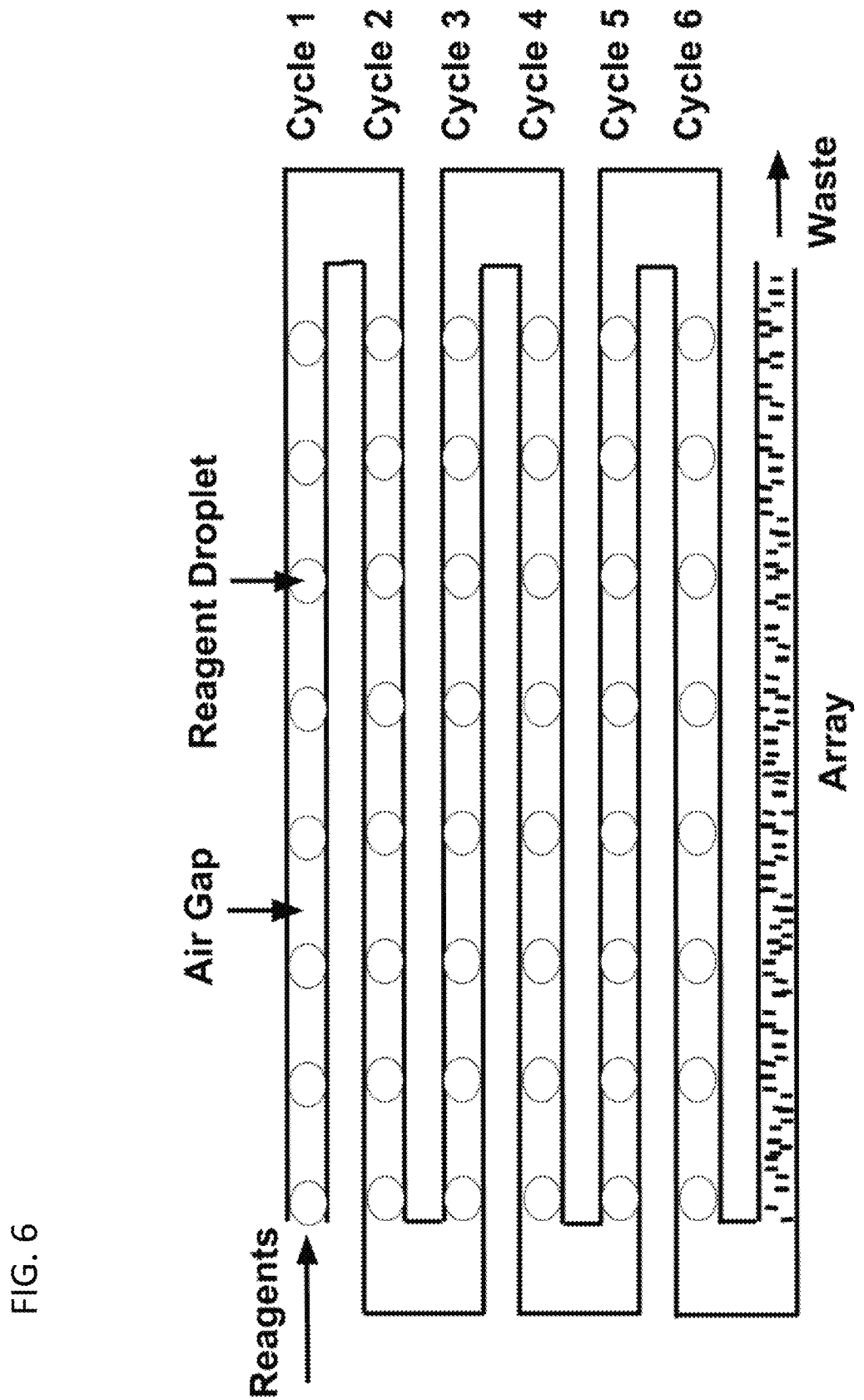
FIG. 6: Shunting multiple packets of sequencing reagents over target templates. The schematic shows the passing of multiple reagent packets (containing sub-packets e.g. droplets) over a target polynucleotides array contained in a channel. The parts of the channel bearing the array of target polynucleotides is exposed to different number packets according to the number of cycles to be conducted (six cycles shown in this example). Each packet is used only once. In this example each packet contains 8 sub-packets which can comprise, nucleotides plus polymerizing agent, cleavage agent if required, imaging reagent if required and wash reagents as required.
Figure 8:
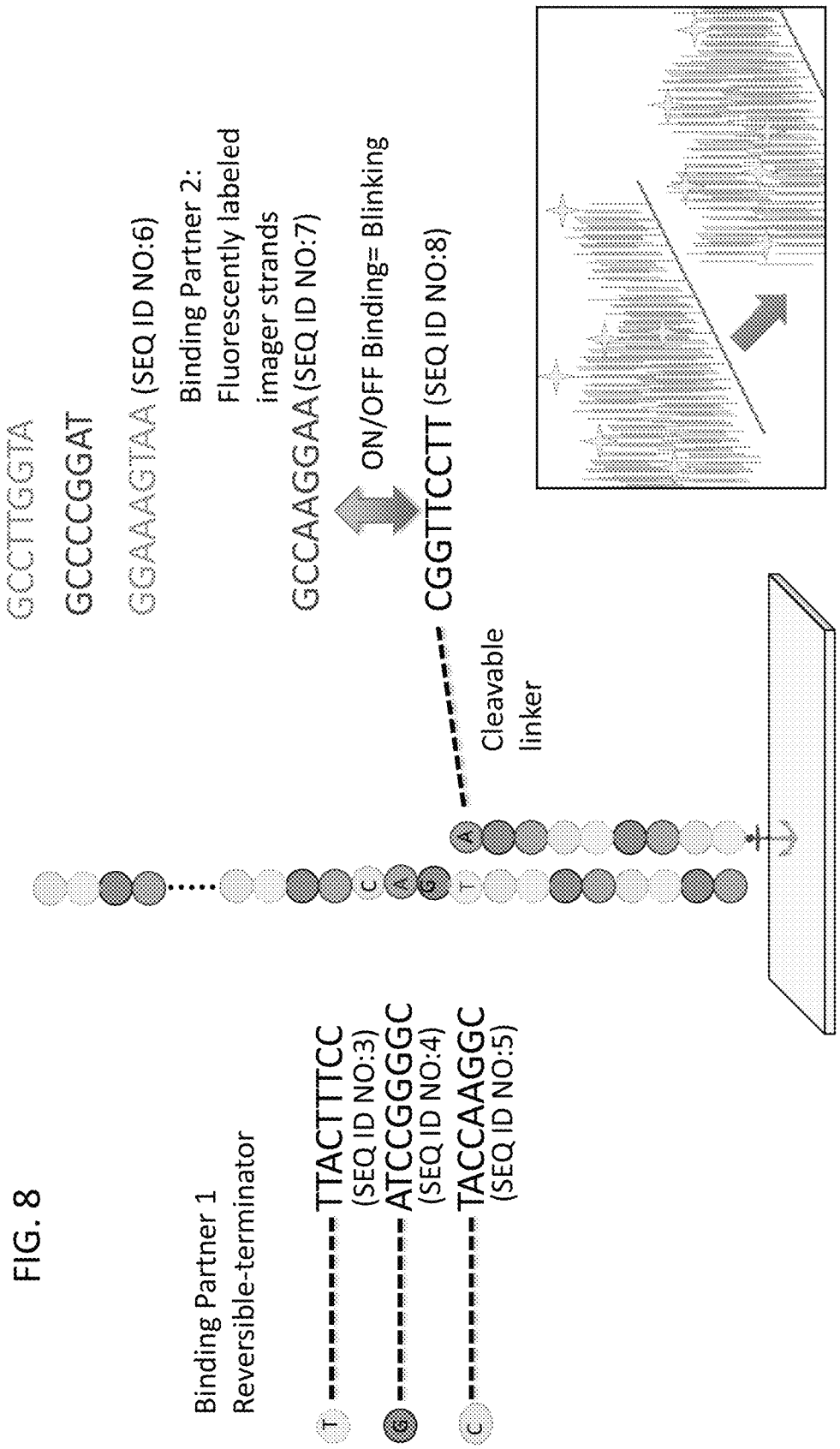
FIG. 8: Super-resolution homogeneous sequencing by synthesis using DNA PAINT. Incorporated nucleotide attached via a cleavable linker to binding partner 1 and determination of nucleotide identity by detecting label on binding partner 2. Using transient on/off binding of binding partner 2 as Imager strand in DNA PAINT to Super resolve incorporation on closely spaced reactions. Inset schematic shows different signals temporally arising sparsely across a lawn of polynucleotides
Figure 9A:
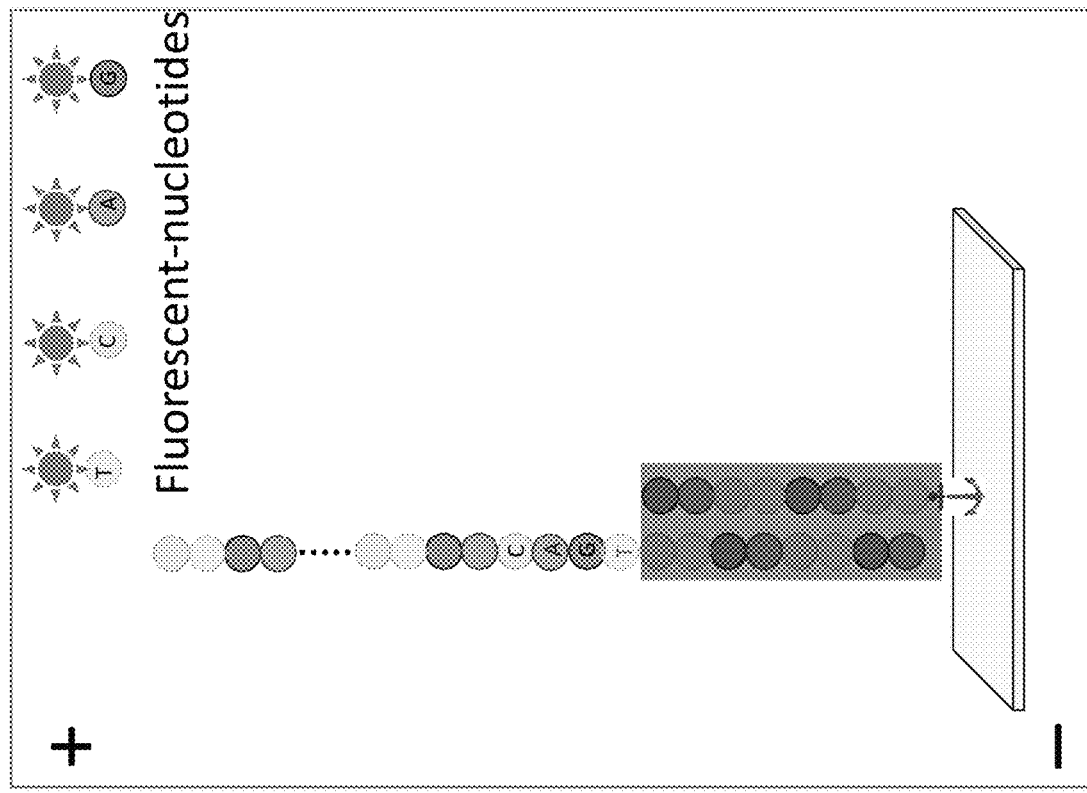
FIG. 9A and FIG. 9B: Electrical control of nucleotides by switching polarity between surface comprising the target polynucleotides being sequenced and the surface not comprising target polynucleotides being sequenced. Schematic showing (FIG. 9A) attraction of −ve charged nucleotides to the surface on which the target template is disposed (FIG. 9B) attraction of the −ve charged nucleotides to the surface on which the target template is not disposed.
Figure 9B:
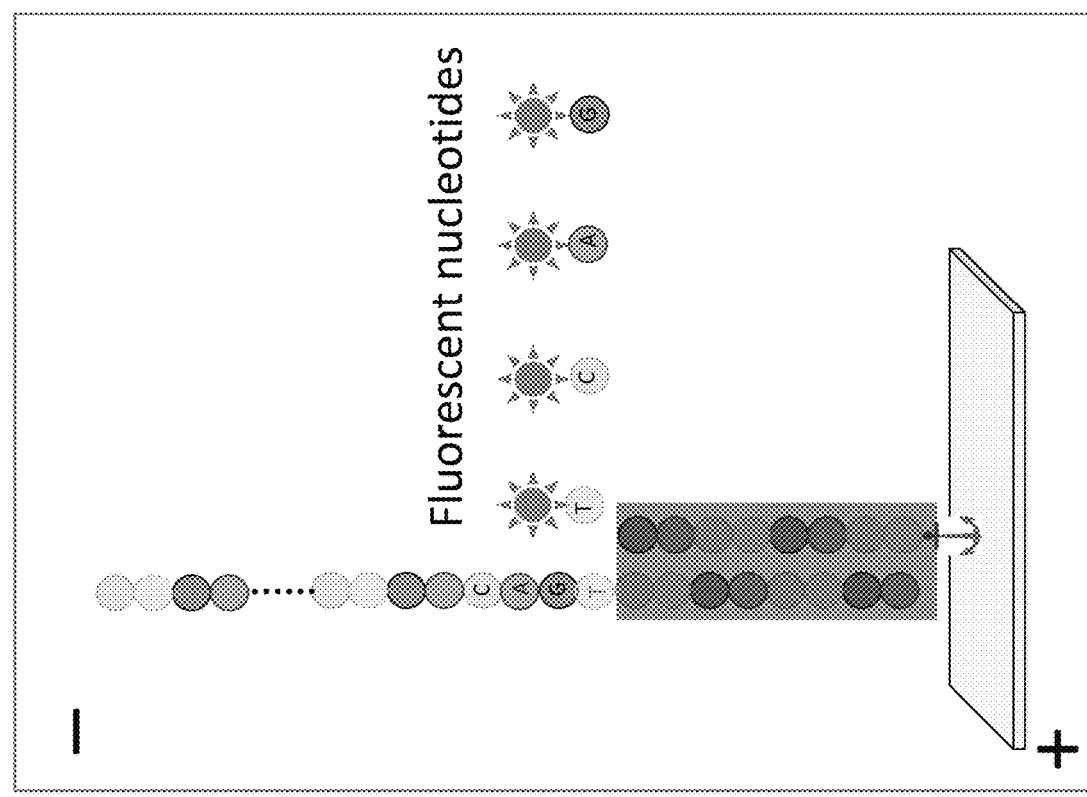
Figure 10A:
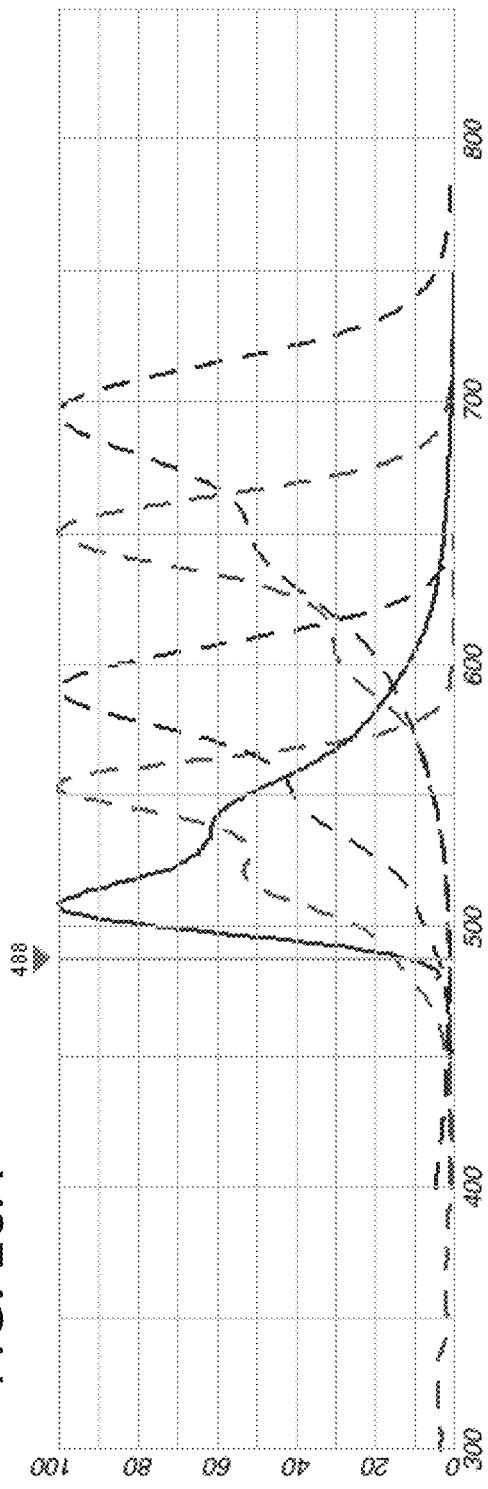
FIG. 10A and FIG. 10B: Single intercalating dye donor, multiple acceptors.
Figure 10B:
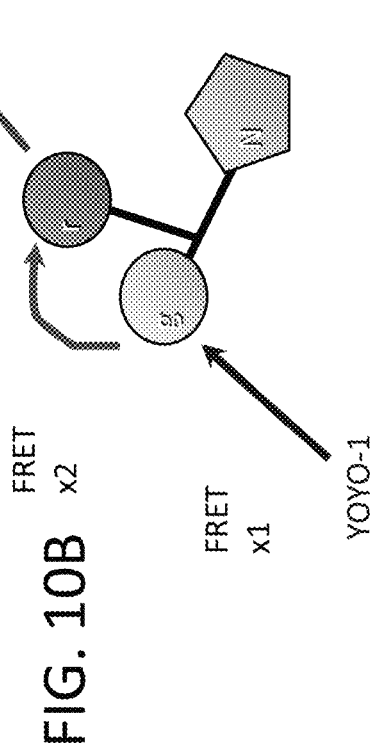
Figure 11A:
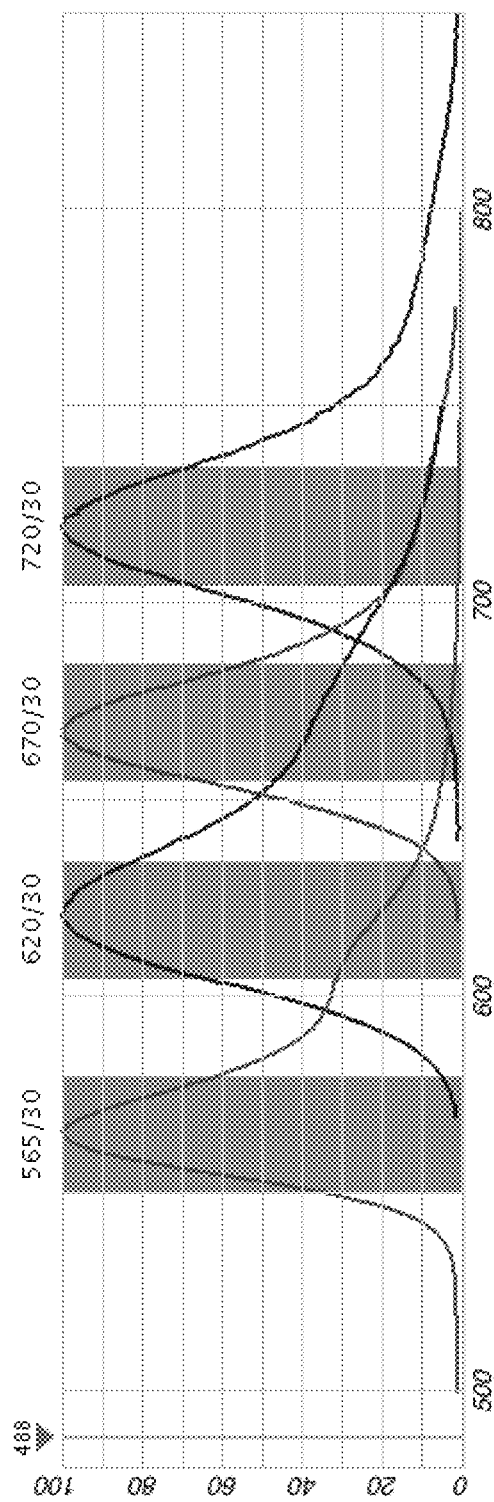
FIG. 11A and FIG. 11B: Identifying the incorporated nucleotide by determining the fluorescence signature of the dye across multiple bandpass emission filters.
Figure 11B:
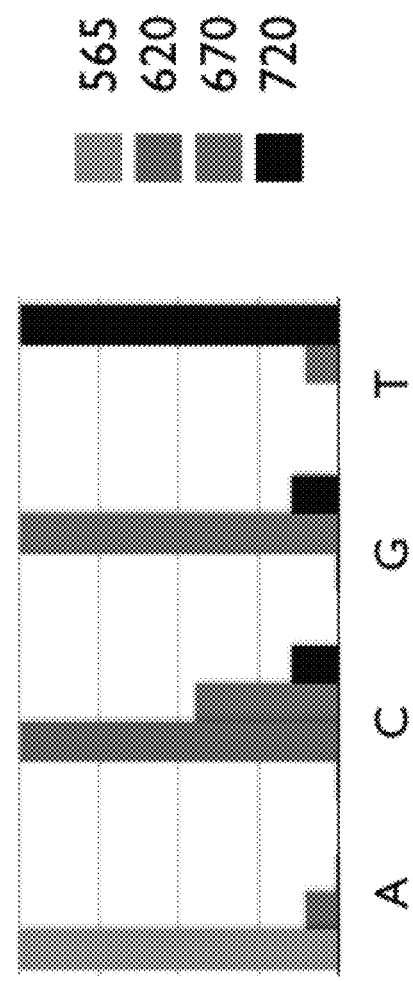
Figure 12:
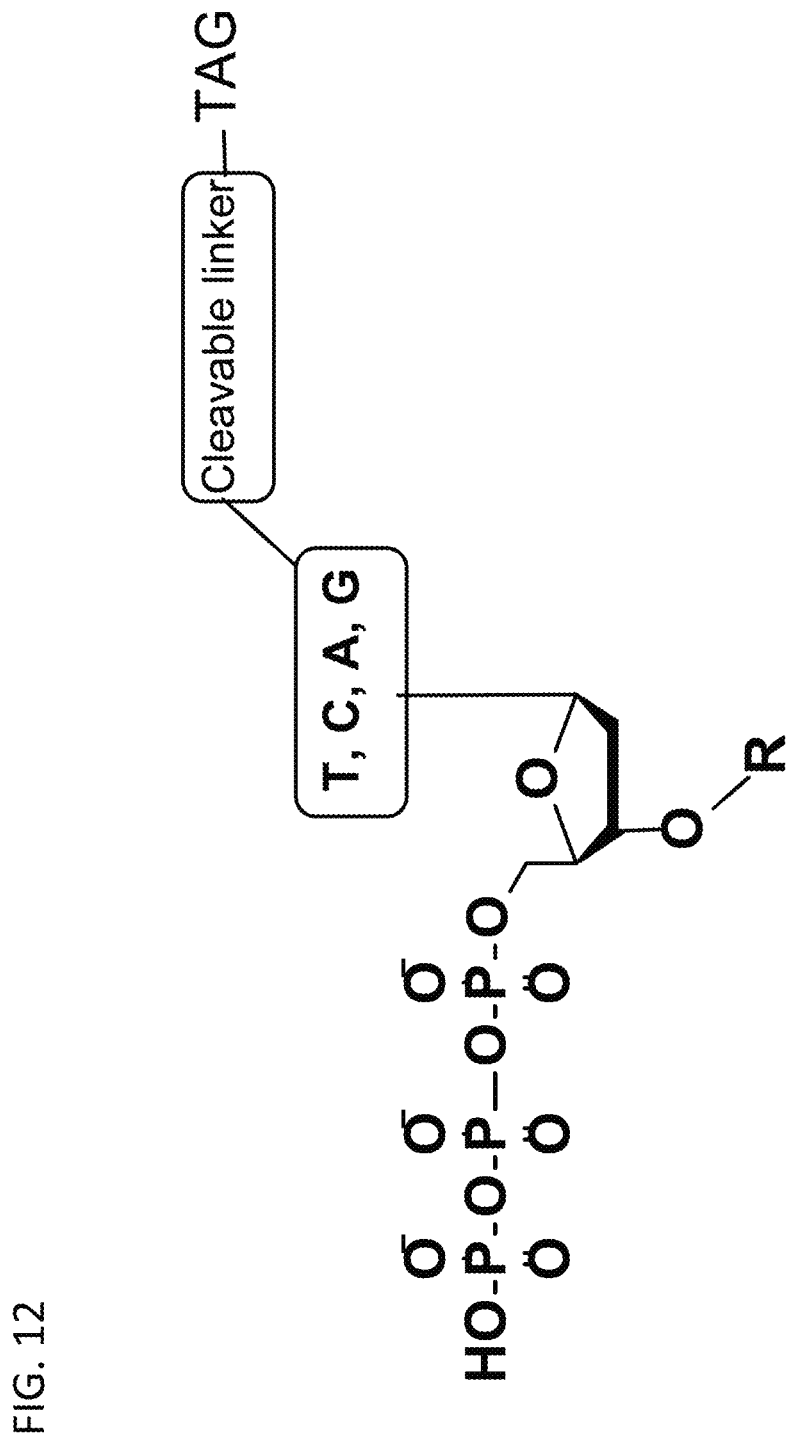
FIG. 12: General class of reversible terminator. R is a reversible terminator or a OH group. When R is a reversible terminator it may include a modification from the class nitrobenzyl, dithio, azidomethyl, ester etc. The cleavable linker can be any group including one or moieties selected from the class: nitrobenzyl, dithio, azidomethyl, ester etc. The linker may be chemically or photochemically cleavable. The Tag can be an oligonucleotide which can be DNA, RNA, LNA, PNA or a combination thereof, a fluorescent dye or nanoparticle such fluorescent dye preferably compatible with STED or STORM. In some cases there is not linker or label on the base. Instead the R terminator carries the tag.
Figure 13:
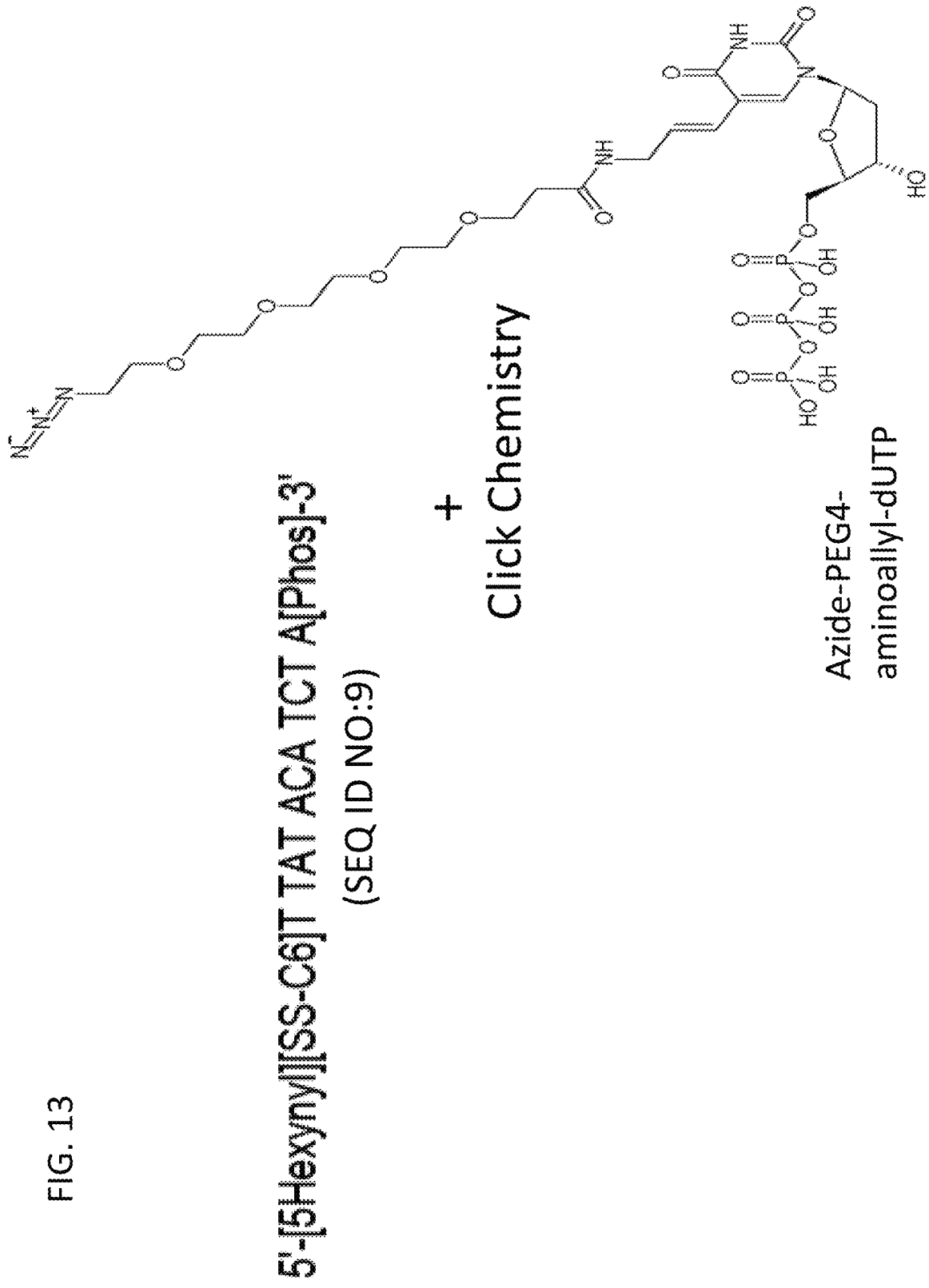
FIG. 13: Click chemistry of alkyne modified cleavable oligonucleotide to azide modified nucleotide. The long linker structure contributes to making this oligo-tagged nucleotide a virtual reversible terminator. A version with a non-cleavable oligonucleotide and cleavable linkage closer to the base position can also be used.
Figure 15:
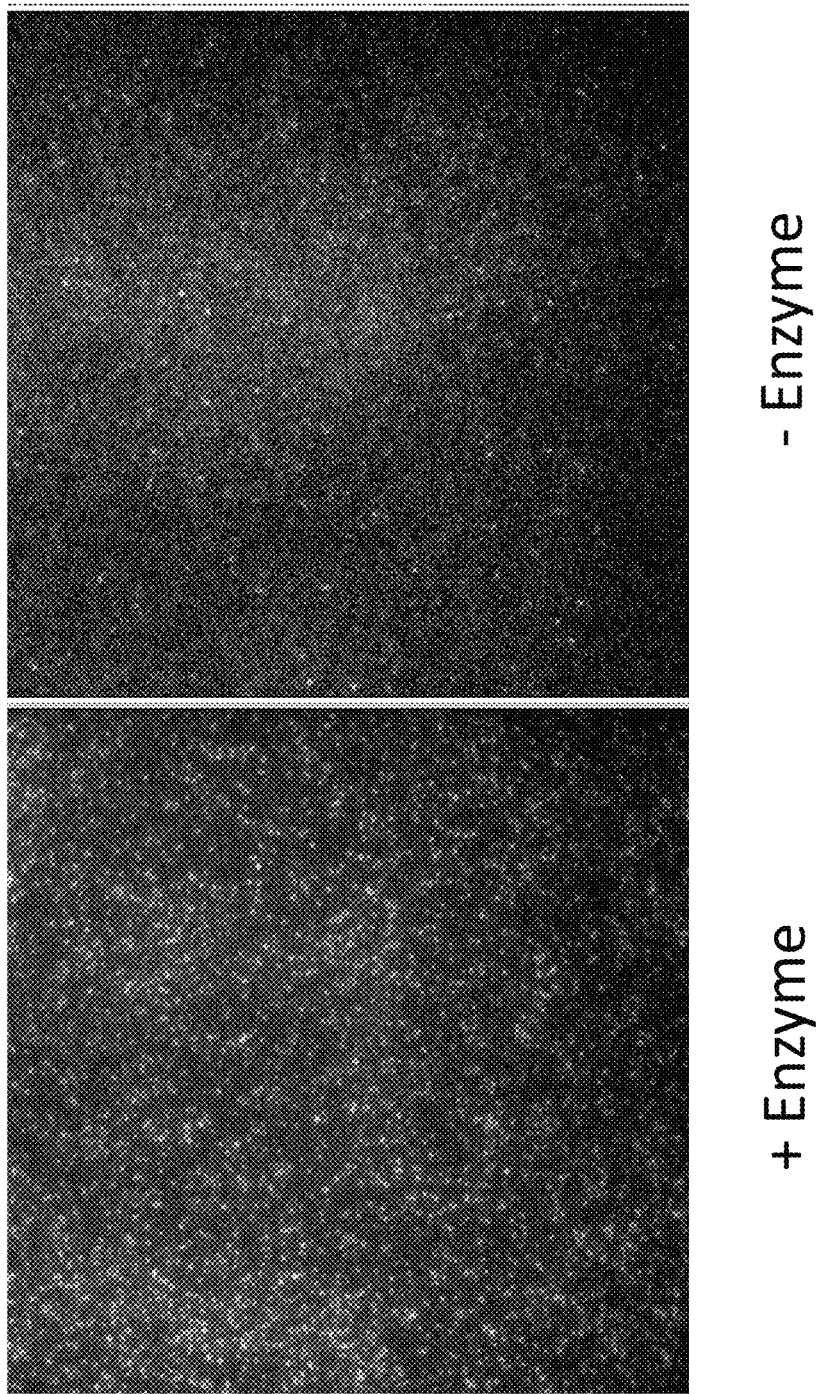
FIG. 15: Incorporation of oligo-tagged nucleotide into self-priming hairpin and imaged with DNA PAINT (left). No enzyme control shows few signals. This shows that the signal in the presence of the enzyme are predominantly due to incorporation and not due to non-specific binding. It also shows that the DNA PAINT Imager strains do not cause significant non-specific binding.
Figure 16:
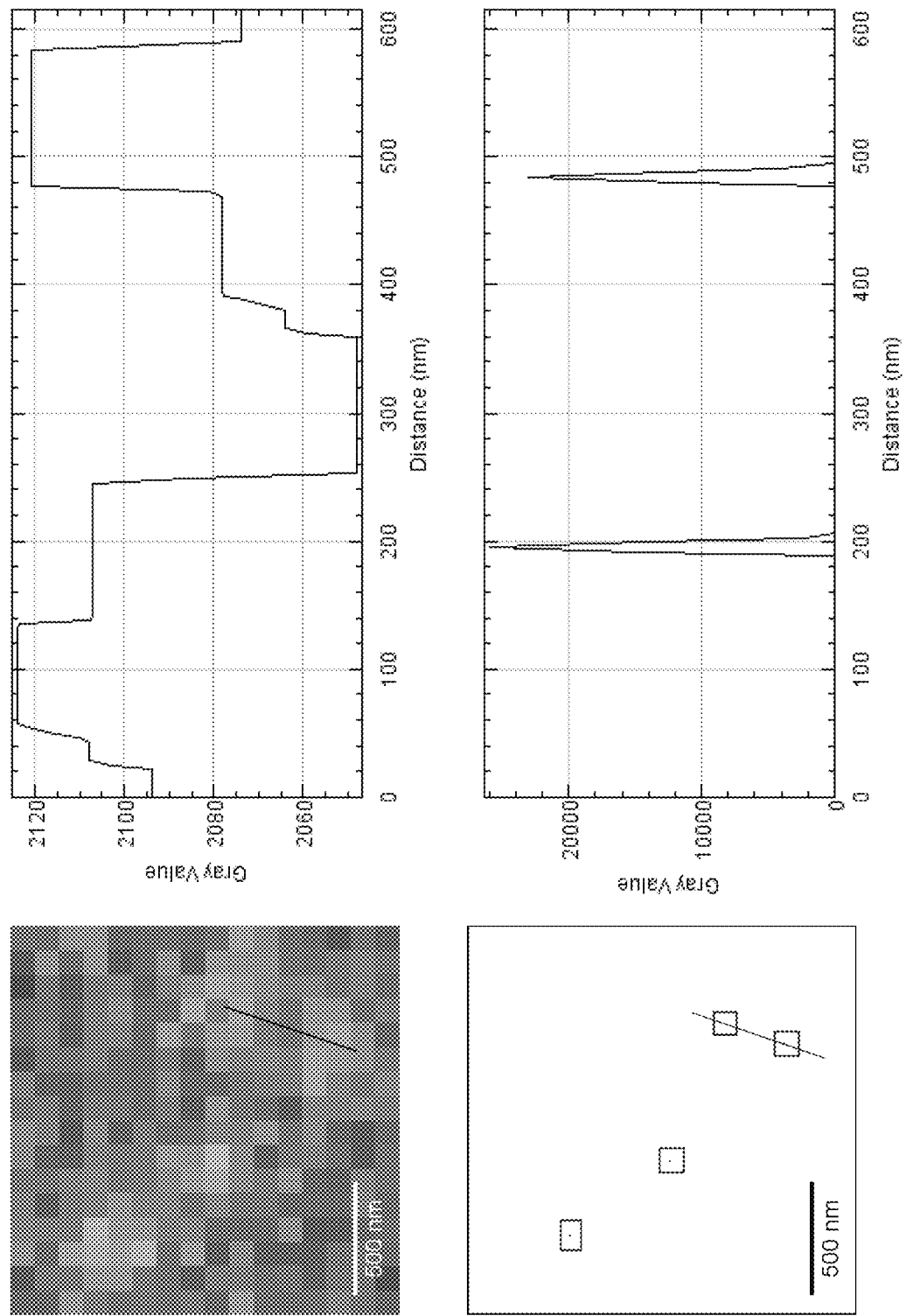
FIG. 16: Sub-diffraction single molecule localization of DNA PAINT imagers on Oligo-tagged nucleotides incorporated into a self-priming hairpin in a flow cell. The top left shows the pixelated blow up of the raw image. The bottom left shows the ThunderSTORM processed image of the same field of view. Four distinct signals are detected and each can be localized to nanometer precision. The graph on the top right shows the pre-processed plot of intensities across the line. The graph on the bottom right shows the post-processed plots of intensities showing localization to within a few nanometers.
Figure 17:
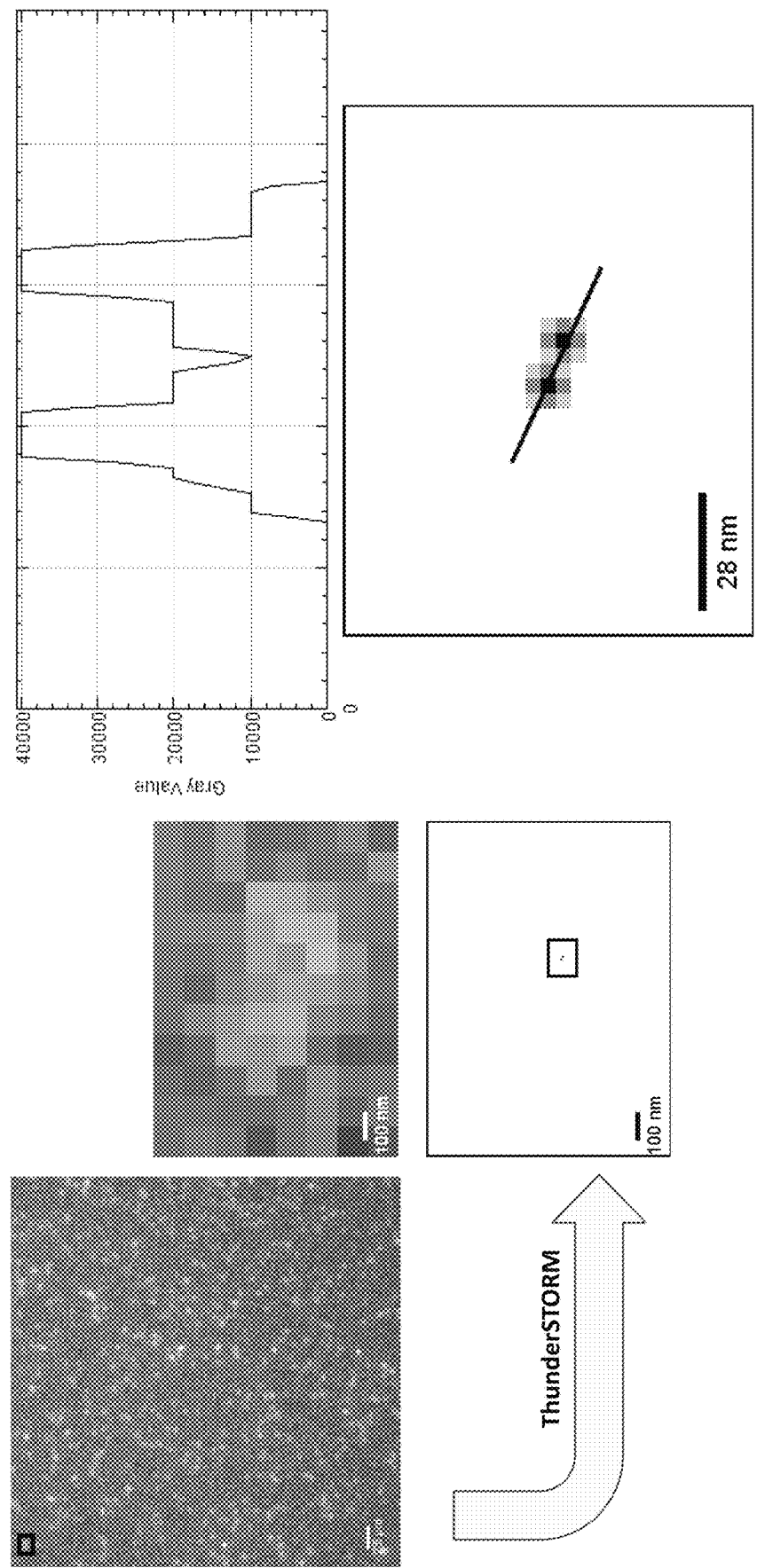
FIG. 17: Super-resolution of two self-priming hairpins extended with oligo-tagged nucleotides and imaged with DNA PAINT. Top left shows raw 256×256 image taken on a Hamamatsu ImageEM with 16 uM pixels, 200 Ms exposure, no gain, 532 nm laser, dichroic and long pass filter; Cy3B labeled imager sequence; The central top image shows zoom in of inset box in the 256×256 image. The central bottom shows the ThunderSTORM processed image of the same area. Bottom right shows the zoom in of box in post-processed image showing resolution of two oligo-tagged nucleotide extended hairpins. The graph on the top right shows that the two previously unresolved points are about 10 nm apart.

Alternatively reagents for the Illumina Genome Analyzer II are loaded per cycle in the order: High Salt Buffer; Incorporation Buffer; Incorporation Mix (mixture of polymerase and labeled nucleotides); Incorporation buffer; scan mix; cleavage buffer; cleavage reagent; cleavage buffer. Depending on whether scheme described in FIG. 5 or 6 is used, the reagents are loaded once each into the fluidic circuit or are loaded as many times as needed according to the number of cycles to be conducted (e.g. 150). These reagents are loaded into a fluidic circuit. Here, the Cavro rotary valve (Tecan), is programmed to pull volume of each of the regents, but each reagent pull is interspersed with pull onto air. In this way reagents are loaded into the fluidic circuit separated by air pockets or a liquid immiscible with the sequencing reagents such as oil.

Details of the Illumina kit can be downloaded from the website:
support.illumina.com/content/dam/illumina-support/documents/myillumina/6936f0c7-b8cb-4a62-bcc5-207a05850b1f/truseq_sbsv5_ga_reagentprepguide_15013595_d.pdf.

Imaging is done by using 532 nm laser for two of the four dyes and 660 nm laser for the other two of the dyes on the nucleotides. Each of the two dyes excited by each laser are differentiated by using specific emission filters and an algorithm designed to determine the signatures of each dye.

One of a number of different Illumina sequencing instruments can be used including the Genome Analyzer IIx. An Illumina flow cell or a custom flow cell with footprint compatible with the Illumina flow cell holder and inlet and outlet ports (e.g. custom order from Dolomite, Cambridge UK) can be used. Alternatively, a home-built system comprising an inverted microscope, with high numerical aperture objective lens, lasers, CCD camera, fluorophore selective filters and syringe pump based or pressure driven reagent exchange system and a heated stage. The home-built system can be adapted for other nucleotide/dye combinations than offered by Illumina.

When an Illumina flow cell is used, it is preceded by Illumina library preparation to add Illumina adapters. The sample DNA is loaded into the flow cell held in an Illumina cluster generation workstation. In some embodiments cluster amplification is conducted. However in other embodiments following capture and denaturation cluster amplification is not conducted and sequencing will proceed on the immobilised single molecules. In some embodiments a self-priming hairpin template is loaded into the flow cell, said flow cell coated with streptavidin and template is modified with one or more biotin groups.

The sequencing is then performed by using either of the schemes described in FIGS. 5 and 6 and involves the fluidic packets flowing over the immobilised single molecules on the surface in the order described above. When the scan mix is flowed in the flow cell is imaged. Optionally the Photometrix CoolSnap camera in the Illumina GAII can be replaced with a Hammamatsu ImageEM and individual molecules extended with Illumina fluorescent nucleotides can be readily imaged.

We confirmed the extension of a self-priming hairpin template inside our flow cell using the Illumina reagents (see Sequencing with DNA PAINT section below).

In some embodiments intercalating dye such as YOYO-1 is placed in the sequencing buffer and Illumination is by a 475 nm or 488 nm laser and FRET to the Illumina dyes is detected.

Sequencing with Intercalating Dyes as FRET Donor and Photo-Chemically Cleavable Reversible Terminator Acceptors YOYO-1 Intercalator dye is provided in the reaction mix together with ThermoPol 1 reaction buffer, Therminator polymerase and four photocleavable nucleotides (e.g. Lightning Terminators from Lasergen or equivalent nucleotides) at 650 for 5 to 30 minutes. Nucleotides based on Lightning Terminators can be custom synthesized and each of the nucleotides are labeled with differentiatable dyes (e.g. Cy3, Cy3.5, Cy5, Cy5.5 or Cy3B, atto 595, atto 655, Cy7). The flow cell can be incubated in a flat-block PCR machine (G-STORM) or a heated stage is used on the microscope. After the reaction, the nucleotides incorporated into the surface bound templates are detected using TIRF illumination through a high NA objective lens (1.45 NA Nikon) on Nikon Ti-E microscope using Perfect Focus (PFS). Images are taken on a 512×512 ImageEM Camera (Hamamatsu). A Melles Griot 488 nM laser is fiber coupled into the TIRF attachment of the microscope. A 488 nm laser clean up filter is used along with a Longpass dichroic mirror and emission filter in the Nikon filter cube. QuadView from Photometrics is used to split the emission light by wavelength into four quadrants on the CCD camera. Following detection the fluorescent labels and terminator are cleaved using ultraviolet light exposure for 5-10 minutes. This allows the next cycle to commence.

Sequencing with Label on Polymerase as FRET Donor and Photo-Chemically Cleavable Reversible Terminator Acceptors The novel reaction is run in the presence or absence of intercalating dye using polymerase that is either directly labeled with fluorescent donors or is attached to protein (e.g., Streptavidin) which is labeled with fluorescent groups. In this embodiment, the polymerase needs to remain attached to the target polynucleotides after incorporating a base. The protein can be engineered to optimize this.

Labeling of the Polymerizing Agent

Amine containing amino acids such as lysine residues can be labeled with NHS chemistry. Cytokine residues can be labeled with Malemide chemistry. Examples of this chemistry are well known to those of ordinary skill in the art and can be implemented, for example, using commercial kits (e.g., available from thermofisher Scientific and discussed in The Molecular Probes® Handbook A GUIDE TO FLUORESCENT PROBES AND LABELING TECHNOLOGIES 11th Edition (2010). For example, reaction of thiols with maleimides is a process which is widely used for bioconjugation and labelling of biomolecules including proteins and peptides.

Maleimides are electrophilic compounds which show high selectivity towards thiols. While maleimides hardly ever occur in nature, thiols are very abundant. They are encountered in proteins and peptides as cysteine residues. Although natural DNA does not contain thiols, synthetic oligonucleotides with thiol groups can be easily prepared.

Thiols are prone to oxidative dimerization with the formation of disulfide bonds. Cytokine residues thus form cysteine bridges, which stabilize protein tertiary structures. Disulfides do not react with maleimides. Therefore, it is necessary to reduce disulfides prior to the conjugation, and to exclude oxygen from the reaction.

Conjugation protocol depends on the solubility of the starting components. For compounds with low aqueous solubility, like most fluorescent dye maleimides, use of organic co-solvent, such as DMSO or DMF, is essential.

One example protocol for the conjugation of Lumiprobe dye maleimides with proteins, peptides, and other thiolated biomolecules is as follows:

i. Dissolve the protein or other molecule containing thiol to be labeled in degassed buffer (PBS, Tris, HEPES are good, although others buffers containing no thiols can be used) at pH 7-7.5 in plastic vial. Buffer can be degassed by applying vacuum on it for several minutes, or by bubbling through inert gas (nitrogen, argon, or helium). For proteins, good concentration is between 1-10 mg/mL.

ii. Add an excess of TCEP (tris-carboxyethylphosphine) reagent to reduce disulfide bonds, flush with inert gas, and close. 100× molar excess of TCEP is fine. Keep the mixture for 20 minutes at room temperature.

iii. Dissolve maleimide in DMSO or fresh DMF (1-10 mg in 100 uL).

iv. Add dye solution to thiol solution (20× fold excess of dye), flush vial with inert gas, and close tightly.

v. Mix thoroughly, and keep overnight at room temperature, or 4 Celsius.

vi. Purify by gel filtration, HPLC, FPLC, or electrophoresis.

For maleimides with poor aqueous solubility, like most dye maleimides, one can use a co-solvent (e.g., DMF or DMSO). Maleimides with good aqueous solubility (like sulfo-Cy maleimides) can be dissolved in water. If precipitation occurs, increase content of organic co-solvent in the mixture to achieve better labelling.

In one example, a DNA Polymerase 1 (Klenow Fragment) mutant containing a single native cysteine (C907) is incubated in 50 mM Tris-HCl buffer, pH 7.0, 120 µM tris(2-carboxyethyl)phosphine with 5- to 10-fold molar excess of Cy5 maleimide (GE healthcare) for 1 h at room temperature. The reaction is stopped using 10 mM dithiothreitol (DTT). Cy5 labeled enzyme is separated from the free dye on polyacrylamide Bio-Gel P6 spin columns. These stringent reaction conditions yield ~70% KF conjugation to Cy5 and minimize doubly labeled species. In other examples the Cy5 is replaced with, Atto 655, Atto 647N, Cy3B, ATTO 542 Atto 488 or Alexa 488, depending on whether it is used in FRET and the nature of the FRET partners.

The polymerase can also be fused with a chromophore containing domain, e.g. green fluorescent protein or its variants. The emission wavelengths and brightness of such domains can be optimised by mutations at various residues in the polypeptide.

The polymerase can also be attached to streptavidin by in vivo biotinylation (BPS Biosciences.com) of polymerse and its expression and purification. The biotinylated polymerase is then conjugated in PBS to streptavidin or neutravidin which can be labelled. Streptavidin or Neutravdin were labeled with Cy3 or Cy3B Mono Maleimide (Amersham Biosciences) according to the manufacturer's instructions. To separate labeled protein from free dye, the product of the reaction was purified on a Superdex200 HR column (GE Healthcare).

Labelling the Pol I gene from *Bacillus subtilis*, BSU Pol I with Cy3-Maleimide (according to Previte et al, 2014, Nature Comm, 6:5936):

Purified BSU Pol I was buffer exchanged into conjugation buffer (50 mM ACES pH 7.4, 20 mM NaCl, 0.2% Tween-20) using illustra NAP G-25 columns (GE). The protein was then concentrated to 100 mM and conjugated to Cy3-Maleimide reactive dye (GE) using the manufacturer's protocol. The labelling reaction was incubated at 4_C for 16 h, followed by diafiltration and concentration using vivaspin 6 (30 kDa MWCO) concentrators (GE). Final buffer exchange and excess Cy3-Maleimide removal was performed using illustra NAP G-25 columns pre-equilibrated in storage buffer (50 mM ACES pH 7.4, 20 mM NaCl, 0.2% Tween-20, 1 mM DTT). Molar labelling efficiency was calculated spectrophotometrically using extinction coefficients of 150, 000M_1 cm_1 and 55,810M_1 cm_1 for Cy3 and BSU Pol I, respectively. Protein lots with labelling efficiencies of Z95% were aliquoted and flash frozen in liquid N2 and stored at −80 C until use.

Attaching Nanoparticles to Phi29 Polymerase (according to Beechem U.S. Ser. No. 14/584,829): 300 µL, of a stock solution of His-tagged phi29 polymerase (SEQ ID NO:8 of U.S. Ser. No. 14/584,829) (56 µM) which is exonuclease minus (flexible linker: SEQ ID NO:20 of U.S. Ser. No. 14/584,829) (stock solution in: 10 mM Tris (pH 7.5) buffer with 100 mM NaCl, 1 mM DTT, 0.5% Tween-20, 0.1 mM EDTA and 50% v/v glycerol) was buffer exchanged into 100 mM Tris (pH 7.5) buffer with 300 mM NaCl using an NAP-5 column. C8 Qdot Nanoparticles (160 µL, 4.9 µM in 50 mM borate buffer pH 8.0) were concentrated to approximately 30 µL by ultrafiltration (VivaSpin, at 100K MWCOO, and mixed with the buffer exchanged phi29 polymerase (440 µL, 26.9 µM in 100 mM Tris (pH 7.5) buffer with 300 mM NaCl n a 1:15 molar ratio (nanoparticle to polymerase). The resulting solution was incubated overnight at 4° C., concentrated to 30 µL by ultra-filtration with a 100K MWCO VivaSpin centrifugal concentrator, further purified on SUPERDEX 200 column using 100 mM Tris (pH 7.5) buffer with 300 mM NaCl as the eluent.

Sequencing with Label on Luciferase-Polymerase Fusion as BRET Donor and Photo-Chemically Cleavable Reversible Terminator Acceptors The above reaction is conducted with a polymerase which is fused with luciferase. In this embodiment Therminator (9° N variant) is fused to Luciferase. This is done at the DNA level, to create a plasmid that can express the fused gene, whether in a host that can produce the fused protein or by using the Transcend Coupled Transcription/Translation Kit (Promega). To carry out the bioluminescence reaction of Luciferase, its co-factors are added to the mix. These co-factors include: luciferin, 02, ATP.

Nanoluc protein fusion vectors can be used to make the fusion protein. The small size (19.1 kDa) and extreme brightness (about 100-fold brighter than either firefly [*Photinus pyralis*] or *Renilla reniformis*) of NanoLuc® luciferase (Nluc) make it a useful protein fusion partner.

Binding the Polynucleotide with Polynucleotide Binding Reagents

Intercalating dyes, major groove binders, labeled non-specific DNA binding proteins cationic conjugated polymers can be bound to the DNA. Intercalating dyes can be used at various nucleobase to dye ratios. Use of multiple intercalating dye donors at a dye to base pair ratio of about 1:5-10 leads to the labelling of DNA with dye molecules (e.g., Sybr Green 1, Sytox Green, YOYO-1) sufficient to serve as donors for nucleotide additions along the growing DNA strand. Some DNA binding reagents are able to substantially cover the polynucleotide. Some dyes that have intercalated into a DNA duplex are able exchange with intercalants in solution at a first rate, whereas others remain fixed for extended periods. The long association of the intercalants is a problem because they can become photobleached and the fluorescence is not easily replenished by exchange of intercalant from solution. In the case of YOYO-1 the speed of exchange can be increased by using the appropriate buffer, for example inclusion of the Methyl Viologen and ascorbic acid promotes the exchange.

Building Modified Nucleotides

Modified nucleotides with labels or tags and reversible terminators can be synthesized by those skilled in the art and with guidance from the many publications and patents in this area. The precursors for making the modified nucleotides necessary for the invention are widely available (e.g. from Trilink, Jena Biosciences, FirebirdBio, Berry associates, Ambergen). In particular a plethora of nucleotides with amino, propargylamino, aminoally modifications at the base are available and several relevant modifications at the 2', 3' or terminal phosphate are available too. These can be linked to carboxy modified tags (dyes, labels) using various kits available on the market including those for NHS ester chemistry. Labels/tags can also be attached to nucleotides with Maleamide chemistry. Several linkers are available that are cleavable such as the dithio and the 2-nitrobenzyl. In particular several nucleotides area available for click chemistry. One important aspect of using oligo tags, is that one can take advantage of the massive number of oligonucleotide modifications that are available and can easily be ordered from oligo vendors such as Gene-Link and IDT. We have taken advantage of the fact that cleavable positions can be included in the oligonucleotide, for example photocleavable positons cleavable y light, dithio positions cleavable by reducing agent, one or more RNA nucleotides which can be cleaved by alkali or RNases. Peptides can also be included between the oligo and the nucleotide and cleavable by protease. We have given one example of click chemistry of a dithio modified oligo to a nucleotide below.

Cleavage of a Photolabile Linker

A photocleavable 2-nitrobenzyl linker at 3' end can be used as a photoreversible linker for a blocker and/or label. The photolabile linker can generally be cleaved by irradiation for 5-15 minutes with 300-360 nm light with gentle mixing, in a buffer of choice. In some embodiments the buffer used is one suitable for nucleotide incorporation by the polymerase that is used and is compatible with a homogeneous sequencing reaction that does not require exchange of reagents. In some embodiments the buffer of choice contains a salt concentration similar to Phosphate Buffered Saline. The addition of DTT in the buffer has a beneficial effect (Stupi et al. Angew Chem 1724-1727) and can speed up the reaction.

For better efficacy specific protocols can be used. In one protocol photocleavage is achieved by UV light at 355 nm at 1.5 W/cm2, 50 mJ/pulse. One pulse is for 7 ns and this is repeated for a total of 10 sec.

Lightening terminators developed by Metzker and co-workers at Lasergen Inc, are highly favorable photocleavable nucleotides. These nucleotides have a 2-nitrobenzyl group attached to bases that are hydroxyethylated and are incorporated by Therminator with fast kinetics, allowing the incorporation reaction time to be short, e.g. down to a minute.

Agitation/Mixing

In various embodiments, effective mixing or agitation is provided, so that there is a turnover of reagents close to the surface and in contact with the target polynucleotides and the extension complex thereon. This mixing can occur by reducing the effects of laminar flow, where little mixing apart from diffusion occurs around samples attached to the surface. This can be done by inducing turbulent flow for which there are various means. Particles with a rough shape can be included in the reaction mixtures, a rough or herringbone or other pattern within at least one wall off the flow cell can promote effective mixing and turbulent flow. The solution can be moved back and forth by external agitation which may be by physical manipulation of the flow cell (this works well when a bubble is included in the reaction solution) and/or by providing acoustic waves.

Super-Resolution Sequencing by Synthesis Using STED

Super-resolution microscopes such as Leica TCS SP8 STED 3× can be coupled to an optional heating mechanism and a pressure driven flow system for reagent exchange, to carry out the sequencing of this invention. The nucleotides are labeled with STED compatible dyes (nanobiophotonics.mpibpc.mpg.de/old/dyes/ and those available from abberior.com). The dyes can be conjugated to nucleotides available from vendors such as FirebirdBio by GeneLink (White Plains N.Y.). Leica TCS SP8 STED 3×, can achieve a sub 30 nm resolution. This can be implemented using 4 colors or less than four colors. Colors can be resolved in STED by using different laser line combinations, or the same laser lines but fluorophores that can be differentiated based on their lifetime.

Super-Resolution SbS with Qdot-Labeled Nucleotides and Stochastic Optical Reconstruction The streptavidin Quantum Dots were conjugated to ss-Biotin dNTPS (Perkin Elmer) in Quantum Dot buffer for several days at 4° C., followed by 3× ultracentrifugation and removal of supernatant at 100,000 rpm on a Beckman Optima. The Qdots-dNTPs were quantitated with nanodrop spectrophotomer (Nanodrop corp, USA). Alternatively the incubation can be carried out at 45° C. for 1 hour.

Extension reactions were performed in the presence of Quantum Dot streptavidin nucleotide conjugates (565 C and 655G, Quantum Dot Corporation, USA). The following polymerase reaction buffer can be used when ss linkage is used: (20 mM Tris-HCl, pH 8.8, 10 mM $MgCl_2$, 50 mM KCl, 0.5 mg/ml BSA, 0.01% Triton X-100).

Detected was done under TIRF microscopy in Qdot Buffer (Molecular Probes, Eugene, Oreg., USA) between the slide and a coverslip and a movie was taken to record the blinking behaviour of the Qdots. The movie was then used to reconstruct a super-resolution image using methods known in the art.

A reducing reaction in 10-50 mM TCEP/250 mM Tris, pH 7.6/100 mM NaCl or Illumina cleavage buffer for 5-10' minutes and washed in Qdot buffer or 50 mM TCEP/250 mM Tris, pH 7.6/100 mM NaCl.

After cleavage the cleaved nucleotide is capped with 50 mM iodoacetamide/100 mM Tris, pH 9.0/100 mM NaCl for 5 minutes, followed by a wash in QDot Buffer or SSC/HEPES/SDS and HEPES/NaCl. This is followed by a further microscope examination to detect removal of the Quantum Dots. This is repeated to obtain a sequencing read.

SbS with Ss-Biotin Nucleotide (Binding Partner 1) and Labelling with Streptavidin-Coated Quantum Dots (Binding Partner 2)

After primer extension, as described above but by using ss-biotin dNTPs which have not been linked. Then the Quantum dots are incubated with the array at 45° C. in Quantum Dot buffer at a concentration between 4 nM and 20 nM. A movie is the taken to record the blinking behaviour of the Qdots followed by cleavage using (or Illumina cleavage buffer) TCEP and capping with Iodacetamide. The blinking behavior provides the opportunity to perform superresolution reconstruction. This is repeated to obtain a sequencing read.

The above as well as nucleotides labelled directly with Qdots (e.g using nucleotides linked to to biotin via SS bridge available from Perkin Elmer which can be independently coupled to Qdots emitting at different wavelengths) can be imaged Super-resolution optical fluctuation imaging (SOFI) is a post-processing method for the calculation of super-resolved images from recorded image time series that is based on the temporal correlations of the independently fluctuating or blinking Qdots (the same approach can be applied to fluorescent dyes that have a tendency to blink in certain media).

FRET and Photoactivation Imaging

To obtain FRET multicolor images, TIRF imaging is combined with laser excitation of donor and emission wavelengths are split on one or more cameras using an image splitter (Dual view, Quad view, W view, Opto-split or custom made optics) for the four emission wavelengths and one for the donor whose emission intensity during FRET is anti-correlated with the emission from the acceptors. Appropriate lasers and filter sets can be chosen by those with skill in the art. A 488 nm laser (Coherent Sapphire 200 mW) has been used to excite intercalating dye as a FRET Donor. A 532 nM laser (Laser Quantum 400 mW) has been used as a photoactivator and a 640 nM laser as the imaging laser both under continuous illumination, coupled through a fiber merge and launch system available from Andor or Nikon.

Photoswitching

Sequencing in which single molecule photo-switching (for STORM) is used it is imperative to use an appropriate imaging buffer containing an oxygen scavenging system: glucose, glucose oxidase, and catalase to minimize photobleaching, and a thiol to facilitate photoswitching (especially when Cyanine dyes are used). The specific compositions of the two buffers that work with Alexa 750 using 752 nm laser light are as follows. BME imaging buffer: Tris (50 mM, pH 8.0); Sodium chloride (10 mM); Glucose (10% w/v); β-mercaptoethanol (143 mM, Sigma, M3148); Enzymatic oxygen scavenger system (1% v/v)

MEA imaging buffer: Tris (50 mM, pH 8.0): Sodium chloride (10 mM): Glucose (10% w/v): β-mercaptoethylamine, pH 8.5 (10 mM, Sigma, 30070): Enzymatic oxygen scavenger system (1% v/v)

The enzymatic oxygen scavenging system was added to the buffer immediately before sequencing, and the stock solution is prepared by mixing glucose oxidase powder (10 mg, Sigma, G2133) with catalase (50 µL, 20 mg mL-1, Roche Applied Science, 106810) in PBS (200 µL), and centrifuging the mixture at 13 000 rpm for 1 min.

Fiducial markers such as fluorescent beads (Invitrogen, F8810) can be used for alignment of datasets between colors and between cycles. The bead positions were localized with high precision over the course of the experiment, based on their images in the raw data. This enabled tightly localized clusters of localizations corresponding to the beads fixed to the sample. The set of localizations collected can be transformed using a polynomial warp transform to account for differences in magnification, rotation, shear, etc., and then the images were aligned using a rigid translation, based on the bead positions in the image. This results in an image-registration precision of 5.6±2.5 nm.

The Vutara 352 superesolution system (Bruker, Germany) uses high powered lasers and CMOS detection of up to 20 uM×20 um field of view and can be used for doing STORM image.

Sequencing with DNA PAINT

Nucleotides were tagged with oligonucleotide sequences as part 1 of a binding pair, with four distinct DNA sequences for each of the four nucleotides, each complementary to distinctly labeled DNA PAINT Imager sequence. The binding partner 1 sequence comprises a complement to the binding partner sequence 2. A list of binding pair sequences is provided in Table 1.

As an alternatively to different DNA imager strands bearing different distinguishable fluorescent labels. The different imager strands, whilst bearing the same fluorescent labels can be distinguished by having different on/off binding rates due to the sequence of the oligonucleotides or by providing different multiples of a common sequence; so A is coded by a single unit of sequence, C by two, G by three, T by four (or any other set of multiples that introduce a difference in the binding frequency). Hence their temporal signature of binding can be used to distinguish them. Also the different imager strands can bear the same fluorophore but imager is added one after the other, with imaging done in between. In addition to the imager strands bearing fluorophores, they can also be designed to carry brighter labels such as optically active nanoparticles such as semiconductor nanocrystals (2-35 nm diameter) and gold particles (e.g. of ~70-120 nm diameter). Oligonucleotides conjugated to customer-defined oligo sequences are available from GeneLink.

The conditions of the imaging reaction can be tailored to promote fast binding kinetics (e.g. higher temperature and/or higher concentration) and fast off rates (e.g. shorter oligonucleotides and/or higher temperature). The DNA PAINT concept can be extended to other binding pairs, as long as they are able to transiently bind under reaction conditions.

Biotinylted oligos (Integrated DNA Technologies) can be linked to the nucleotide or to the fluorescent label by a streptavidin-biotin interaction. Carboxy terminated oligos (Integrated DNA Technologies) can be linked to amine modified (or —ONH2 modified at the 3' end) nucleotide or to the fluorescent label by a Aminoallyl nucleotide N-Hydroxysuccinimide reaction. Alkyne labeled oligos can be linked to azide labeled nucleotides (Available from Jena Biosciences, Germany) using Click chemistry. Azide labeled oligos can be linked to Alkyne of DBCO labeled nucleotides (available from Jena Biosciences, Germany) using click chemistry. Other click chemistry combinations are also possible.

Fluorescently modified DNA oligonucleotides are purchased from Biosynthesis, IBA-GO, Trilink or Gene-Link. Streptavidin is purchased from Invitrogen (Catalog number: S-888). Bovine serum albumin (BSA), and BSA-biotin is obtained from Sigma Aldrich (Catalog Number: A8549). Glass slides and coverslips are purchased from VWR.

We obtained a custom synthesized oligonucleotide (Genelink) containing a partner 2 sequence containing a 5' hexynyl linker, a disulphide, a 3' phosphate (5' [5Hexynyl][SS-C5] TTATACATCTA (SEQ ID NO: 1) [Phos] 3') and clicked it to an azide containing nucleotide, Azide-PEG4-aminoallyl-dUTP (Jena Biosciences) using the Oligo-Click Kit according to kit protocol (BaseClick, Germany) to make an oligo-tagged nucleotide. The clicked oligo-tagged nucleotide conjugate can be purified on G-25 microspin column or an Amicon Ultra 3K. Two rounds of purification may be necessary. The conjugate can be used without purification with the drawback that ~50% of extension products are with unconjugated nucleotide (not suitable for actual sequencing reactions).

A biotinylated self-priming hairpin template (see Figures) was custom synthesized by (IDT, USA). In some cases Therminator (New England Biolabs) was used to conduct initial extension reactions in solution in other cases, Pol475 (Firebird Bio Inc; Taq mutant E520G, K5401, L616A) was used at 65° C. (72° C. can also be used) and the products were checked on a 4% e-gel. The oligonucleotide-tagged nucleotide is an effective terminator under well-tuned reaction conditions. These conditions include for either 0.5 ul or 1 ul (2 Units) of Pol475 or Therminator respectively: 1×Thermopol Buffer (NEB), 1 mM Oligo-tagged nucleotide, 100 uM self-priming hairpin template. 0.2-2 mM Manganese Chloride can be tested and its effects on sequencing determined and used if found to be beneficial We obtained evidence of successful incorporation (upward shift of band compared to template only and compared to no enzyme control). We then tested cleavage using Illumina Cleavage Mix (known to be a reducing agent, TCEP) at 65° C. for 10 minutes or 30 minute and this proved successful by gel analysis.

Alternatively, the PEG linkage can be cleaved oxidatively or by bacterial enzyme (Schramm and Schink Biodegradation, 2: 71-79 (1991)). A cleavable position can be added closer to the base to improve processivity and to obtain extended reads.

Before demonstrating the method on a surface we first established the compatibility of the hairpin and the flow cell set-up with SbS performing extension with Illumina incorporation mix and imaging with 532 nm and 660 nm lasers. This showed that extension was compatible with the set-up and helped us titrate the hairpin concentrations to a suitable level for initial testing of SbS. We then demonstrated SbS on the surface using oligo-tagged nucleotides for DNA PAINT.

A flow cell was made with self-priming hairpin biotinylated at the 5' position immobilized on a surface via streptavidin-biotin interaction. For sample preparation, a coverslip (No. 1.5, 18×18 mm2, ~0.17 mm thick) and a glass slide (3×1 inch 2, 1 mm thick) are sandwiched together by two strips of double-sided tape to form a flow chamber with inner volume of ~20 µL. First, 20 µL of biotin-labeled bovine albumin (1 mg/ml, dissolved in buffer A) is flown into the chamber and incubated for 2 min. The chamber is then washed using 40 µL of buffer A. 20 µL of streptavidin (0.5 mg/ml, dissolved in buffer A) is then flown through the chamber and allowed to bind for 2 min. After washing with 40 µL of buffer A and subsequently with 40 µL of buffer B, 20 µL of biotin-labeled self-priming template (~300 pM monomer concentration) in buffer B are finally flown into the chamber and incubated for 5 min. The chamber was washed using 40 µL of buffer B. This then allowed us to perform SbS using the oligo-tagged nucleotides, which we tested in two experiments with and without enzyme, according the reaction protocol described for the solution experiment above. We freshly prepared the flow cell with a streptavidin coating, immobilized the biotinylated hairpin, performed pre-extension washes and performed the incorporation of oligo-tagged nucleotide to the surface attached self-priming hairpin using Therminator at 65° C. We then performed post incorporation washes before adding a Cy3B labeled DNA PAINT strand and a movie was taken using TIRF imaging. The results of the imaging, without processing immediately showed that many more imager strands were binding to the surface in the case of the +enzyme versus the—enzyme control (see Figures). The movie was processed using the Fiji ThunderSTORM on a Lenovo D30 Computer with Xeon processor and 32 Gb RAM. In this experiment we relied on the fiduciary marker free drift correction algorithm available in ThunderSTORM was used. We were able to obtain single molecule localization of the extended polynucleotides (see figures).

In some cases the sequence acquisition can be stopped after adding just one base useful for methods requiring just single base extension. When the intention is to stop after one base the nucleotide does not need to bear a cleavable linker and the nucleotide of this example, Azide-PEG4-aminoallyl-dUTP, has also been successfully tested conjugated to an oligonucleotide that does not include a cleavable position.

For the next step in SbS, the ss bond in the incorporated oligo-tagged nucleotide was cleaved using Illumina cleavage solution at 65° C. We then capped the cleaved nucleotide using Iodoacetamide, performed washes and then proceeded to subsequent sequencing cycles involving the incorporation, imaging and cleavage process as described above.

Three buffers are used for sample preparation and imaging are: Buffer A (10 mM Tris-HCl, 100 mM NaCl, 0.05% Tween-20, pH 7.5), buffer B (5 mM Tris-HCl, 10 mM $MgCl_2$, 1 mM EDTA, 0.05% Tween-20, pH 8), and buffer C (1×PBS, 500 mM NaCl, pH 8).

Fluorescence imaging was carried out on an inverted Nikon Eclipse Ti microscope (Nikon Instruments) with the Perfect Focus System, applying an objective-type TIRF configuration using a Nikon TIRF illuminator with an oil-immersion objective (CFI Apo TIRF 100×, NA 1.49, Oil). An additional 1.5 magnification is used to obtain a final magnification of ~150×, corresponding to a pixel size of 107 nm. For the sequencing experiments a single 532 nm laser fiber was passed through a fiber optic scrambler (Point Source Inc) to obtain well homogenized illumination after optically coupling to the Nikon Ti TIRF attachment. Excitation and emission was done through 475/532/660 multichroic and 532 nm longpass filter and (Chroma) and the images taken with a Hamamatsu ImageEM camera with a 200 ms exposure and no EM gain.

In other experiments all four nucleotides with different tags and corresponding Imaging tags were used in SbS with Atto 488, Cy3B, Atto 647N and Cy7. For this three lasers are used for excitation: 488 nm (200 mW, Coherent Sapphire), 561 nm (200 mW, Coherent Sapphire) and 647 nm (300 mW, MBP Communications). The laser beam is passed through cleanup filters (ZT488/10, ZET561/10, and ZET640/20, Chroma Technology) and coupled into the microscope objective using a multi-band beam splitter (ZT488rdc/ZT561rdc/ZT640rdc, Chroma Technology). Fluorescence light is spectrally filtered with emission filters (ET525/50 m, ET600/50 m, and ET700/75 m, Chroma Technology; and additional filter cube specific to Cy7 can be used) and imaged on an EMCCD camera (iXon X3 DU-897, Andor Technologies).

In other experiments, 1× ThermoPol reaction buffer is flown into the chamber. This is followed by flowing in Therminator polymerase (NEB) and oligonucleotide tagged nucleotides with a photocleavable linker in Therminator buffer are allowed to react with the immobilized target polynucleotide. As the nucleotide becomes incorporated, its identity can be determined by the persistent binding of the imager strand and because of the on/off binding of the imager strand, the reactions on different target polynucleotides can be super-resolved. After imaging, the termination is reversed by photochemical cleavage of the cleavable linker and the next cycle is triggered. The buffer salt concentration can be raised to ensure effective DNA PAINT binding but this may be at the expense of nucleotide incorporation. However salt tolerating polymerases are known including Phi29, TopoTaq and those disclosed in WO 2012173905. Hence monovalent salt concentration of 0.65 M can be used to undertake DNA PAINT and polymerase mediated nucleotide incorporation in a homogenous reaction.

The imaging comprises 1.5 nM Cy3b-labeled imager strands for the docking strand for A nucleotide, Atto 488-labeled imager strands for the docking strand for C nucleotide, Atto 655-labeled imager strands for the docking strand for G nucleotide, and cy7-labeled imager strands for the docking strand for T nucleotide in a salt concentration in the range of buffer B at room temperature; the use of different temperatures and sequence of the oligonucleotides can require the use of different salt concentrations in the buffer. Ideally the temperature and oligonucleotide sequence is chosen so that a salt concentration suitable for the incorporation can be implemented. The CCD readout bandwidth is set to 1 MHz at 16 bit and 5.1 pre-amp gain. Imaging is performed using TIR illumination with an excitation intensity of 294 W/cm2 at 561 nm.

The DNA PAINT imagers can be excited via FRET donor such as an intercalator dye, which intercalates when the duplex between the binding pairs form or a dye on binding partner 1. It is possible to obtain resolution of a few nanometers (Chemphyschem. 2014; 15(12):2431-5).

Faster CMOS cameras are becoming available that will enable faster imaging, for example the Andor Zyla Plus allows up to 398 fps over 512×1024 with just a USB 3.0 connection, and faster over regions of interest (ROI) or a CameraLink connection. Therefore, operating with shorter docking/imager strands or at a higher temperature or lower salt concentration it is possible to gather enough information for the required resolution in short time periods; for this the laser power is preferably high, e.g. 100-500 mW; Camera Quantum Yield is preferably high, e.g., ~80% and the dye brightness is preferably high. With this the acquisition time required can be reduced to a few seconds. But this can give a resolution gain of >10 fold over diffraction limit methods.

In one embodiment of the invention a novel method of imaging is implemented, using Time-delayed integration with a CCD or CMOS camera, where the sample stage is translated in synchrony with the camera read-out so that the temporal resolution is spread over many pixels. This speeds up the image acquisition as there is no delay in moving from one location on the surface to another. What results is an imaging strip, where say the first 1000 pixels in a column represent 10 seconds of imaging of one location and the next 1000 pixels represent imaging of 10 seconds of the next location. The method described in Appl Opt. 54:8632-6 (2015) can also be adapted.

An advantage of the DNA PAINT method for superresolution imaging of the Imager strand binding, is that every location is always ready, there is little effect of photobleaching or dark states, and sophisticated field stops or Powell lenses are not needed to limit illumination.

When light scattering nanoparticles (e.g. Gold nanoparticles, Nano-Diamond) or semiconductor nanocrystals are used there is a substantial further step-up in speed, because of the brighter, near non-exhaustive optical response of these particles. Again, the camera frame rate and imager on/off rate need to be tailored to get maximum speed enhancement when using such nanoparticle labels. For this TIRF imaging can be conducted in Dark field mode to capture light scattering rather than fluorescence from the particles A dark field set-up from CytoViva Inc can be adapted or a set-up based on Ueno et al (Biophysical Journal Volume 98 May 2010 2014-2023) can be used. This set-up uses a perforated mirror for dark filed illumination and ultra-fast camera (FASTCAM-1024PCI; Photron). The size, composition and shape of particles can allow different intensities and colors to be produced (see U.S. Pat. No. 6,180,415).

When the templates are arrayed in densely packed clusters with molecules ranging from just one nanometer apart special measures need to be taken in the set-up and imaging. The methods described in Optical imaging of individual biomolecules in densely packed clusters in *Nature Nanotechnology* 11, 798-807 (2016) can be employed.

A 2-D lattice e.g. DNA origami with docking sites for templates as a way of organizing the polynucleotides at set distances can be made. The docking sites may be staples that protrude out and may be strands of oligo dT of e.g. 10-70 nt in length for capturing polyA RNA or tailed RNA or DNA. The lattice can be immobilized to the surface using streptavidin biotin interactions. Such a lattice can be custom designed and purchased from vendor GATTAQuant (Germany).

PAINT Sequencing Using Transiently Binding Nucleotides

Figure 18:
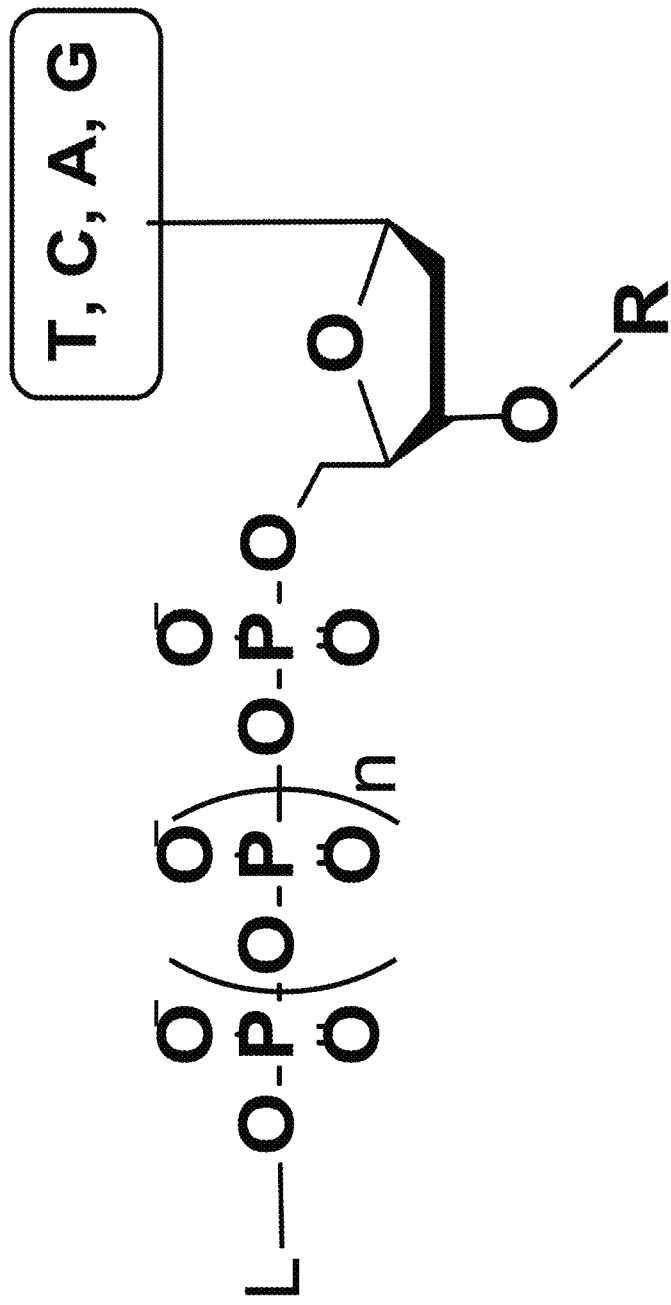
FIG. 18: Phosphate-labeled reversible terminator structure for Transient Nucleotide Binding. Each of the four nucleotides of this structure are provided. When the nucleotide is incorporated the fluorescent group is naturally removed. Additional nucleotides of this structure can transiently bind on and off to the extension complex and be detected but cannot be chemically incorporated due to the presence of the reversible terminator. After a certain number of transient binding events are likely to have occurred the termination is reversed, allowing one of the nucleotides to be fully incorporated (optionally additional phosphates can be added and optionally Manganese to promote incorporation), thereby moving the growing chain to the next position, so that the next position in the template can be interrogated by the transiently binding nucleotides. Incorrect transiently binding nucleotides can be differentiated from the correct ones by their different association times with the extension complex and by consensus (more binding events will be detected from the correct nucleotide). This structure type is appropriate for super-resolution or single molecule localization by PAINT. A suitably modified Klenow, Therminator or Phi29 polymerase may be used as the polymerase
Figure 19:
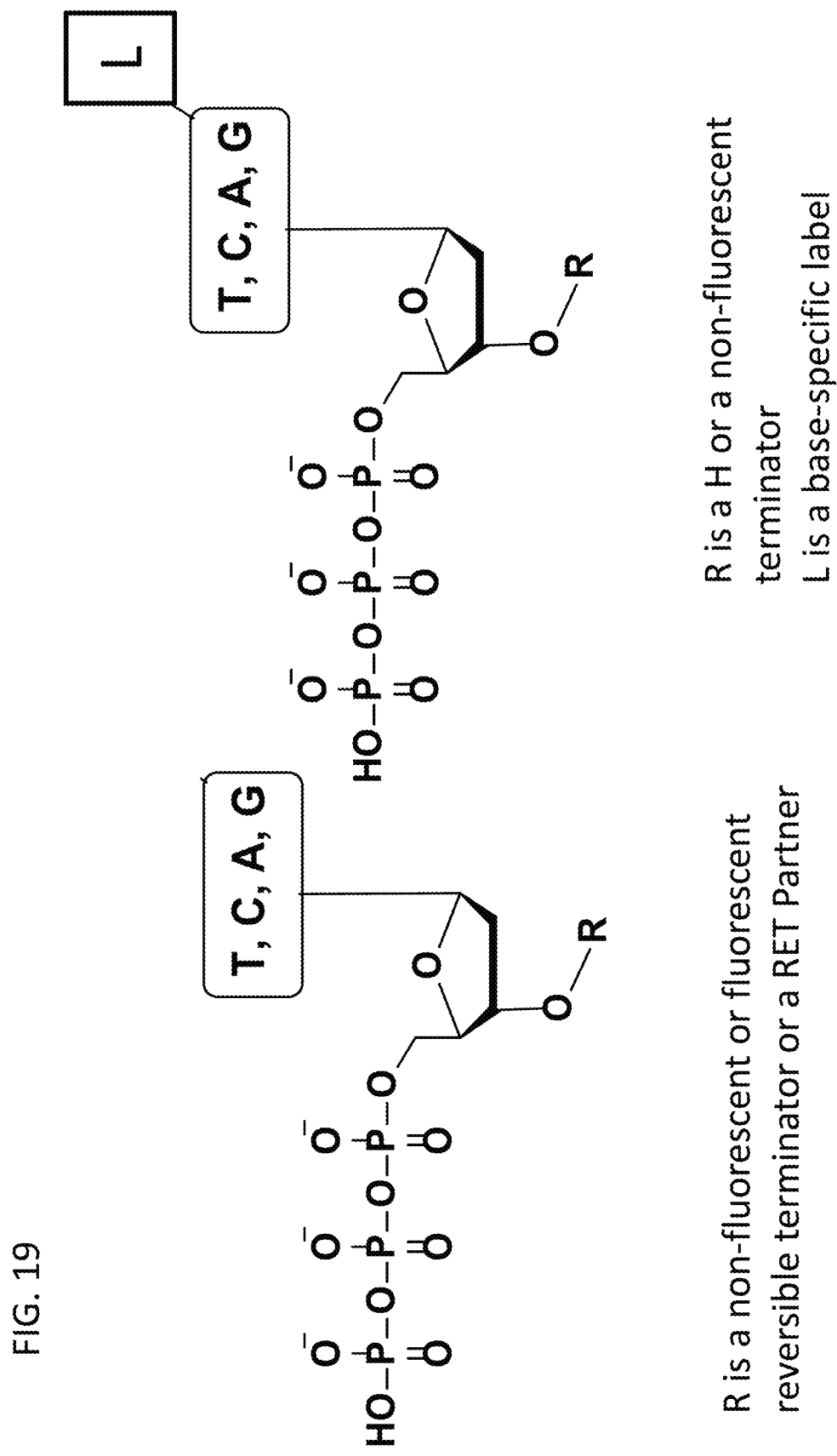
FIG. 19: Dual nucleotide system for Transient Nucleotide Binding. The structure on the left is incorporated and terminates the extension. The structure on the right transiently binds the extension complex to interrogate the next position in the template. After sufficient binding events have been detected, termination is reversed and another of the reversible terminators (left) is able to incorporate, thereby allowing the transiently binding nucleotide (right) to interrogate the next position in the template.
Figure 20:
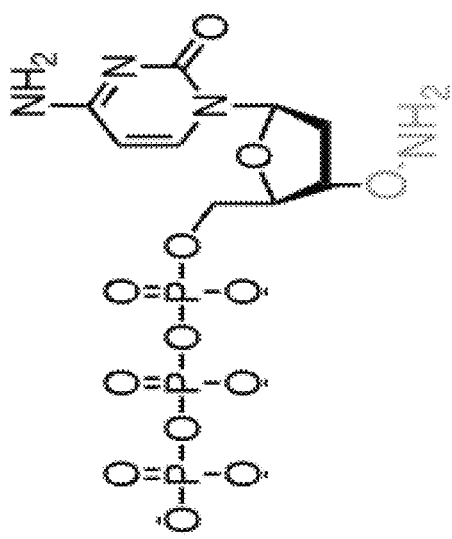
FIG. 20: An —ONH2 modified Thymine (as one example of the al four such nucleotides available from Firebird Bioscience Inc.) nucleotide is shown which we have linked to carboxy modified oligonucleotides on an oligonucleotide synthesizer. The oligonucleotides can be modified at the 3' end to prevent exonuclease digestion, as has been done in this case with a 3' phosphate or a C2 spacer.
Figure 22:
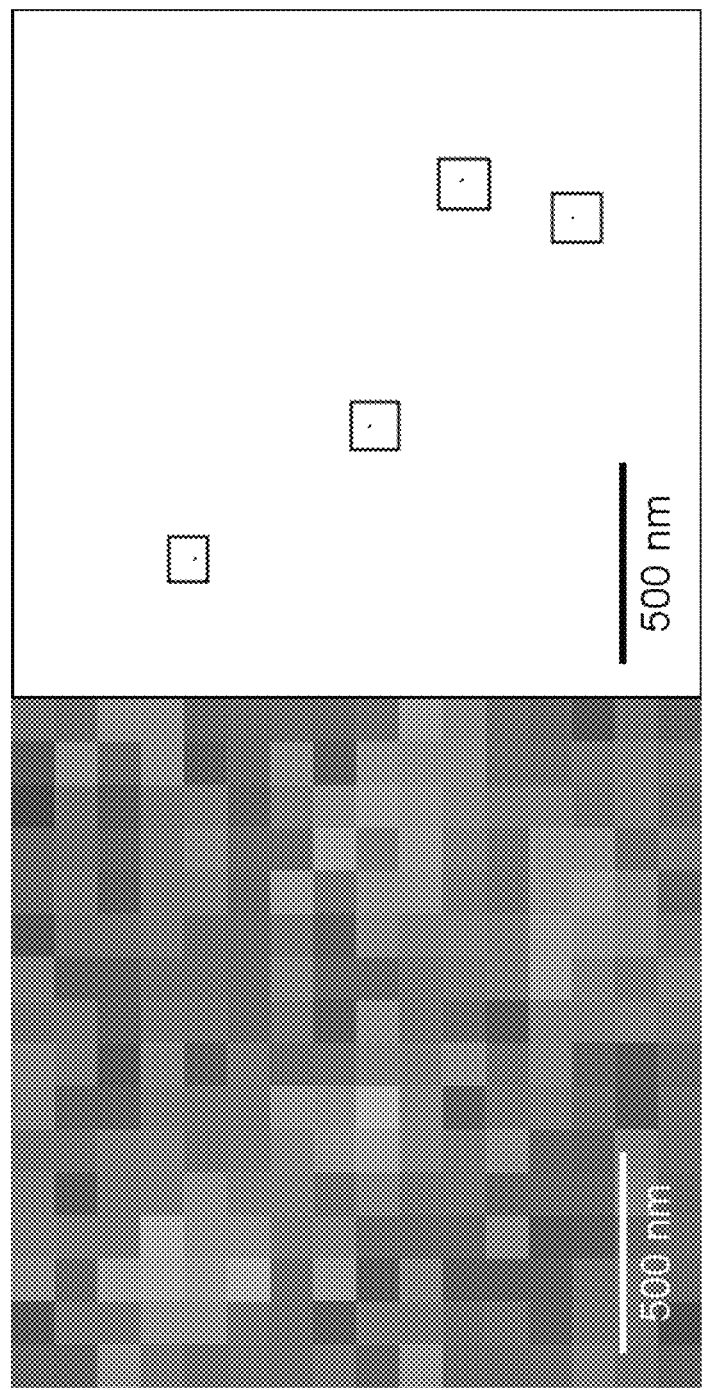
FIG. 22 presents before and after processing of PAINT image of binding of binding partner 2 after incorporation nucleotides tagged with binding partner 1. Left: Raw image data of a single frame in a PAINT data set. Right: The same region after nanometric location processing (image color inverted).

Sequencing with the transiently binding nucleotide structures described in the FIGS. 18 and 19 can be conducted in the same system described above for DNA PAINT by a person skilled in the art. Reversible terminator (which are available from FirebirdBio, Trilink or Jena) for all four bases are used for base incorporation and termination.

In one example all four reversible terminators can be used simultaneously in solution of a polymerization complex.

The following available from Jena Biosciences (Jena, Germany) can be used (catalog numbers in brackets):

3'-O-Azidomethyl-dTTP (NU-939); 3'-O-Azidomethyl-dCTP (NU-940; 3'-O-Azidomethyl-dGTP (NU-938; 3'-O-Azidomethyl-dATP (NU-937).

These nucleotides can be incorporated by Taq DNA polymerase, Therminator II, Pol475 and termination can be reversed by a reducing agent such as TCEP. Then base labelled nucleotides for transient binding can be added in the presence of polymerization complex and multiple events can be detected. The following differently base labelled nucleotides are available from Jena Biosciences:

5-(3-Aminoallyl)-2'-deoxyuridine-5'-triphosphate, labeled with ATT0488

5-Propargylamino-2'-deoxycytidine-5'-triphosphate, labeled with ATT0542

7-Deaza-7-propargylamino-2'-deoxyadenosine-5'-triphosphate, labeled with ATTO594

7-Deaza-7-propargylamino-2'-deoxyguanosine-5'-triphosphate, labeled with ATT0655

A wide range of alternative labels are also available and are chosen depending on whether a FRET or photoactivation mechanism is deployed or not and the capabilities of the optical system used for distinguishing particular dyes by wavelength, lifetime etc.

Typically a concentration of nucleotides greater than 250 nM and preferably greater than 1 uM are required for effective incorporation. Such a concentration of labeled nucleotides can lead to background fluorescence that makes it difficult to detect the transiently binding nucleotide to the polynucleotide disposed on a surface. Hence either a structure such zero-mode waveguide or nanohole is used which does not allow illumination of the bulk solution or a FRET mechanism or photoactivation mechanism as described herein must be used.

The rate of on-off binding of the transient binding nucleotide can be manipulated by choice of temperature, pH and/or divalent cation. A number of divalent cations (e.g., Mg++, Mn++, Zn++, Co++, Ca++, Fe++, Cr++, and/or Sr++) can be tested to achieve the desired rate. For example the lower the concentration of Mg2+ or Mn2+ the faster the off rate; a combination of two cations can also be used. See Vashashista et al. The Journal of Biological Chemistry 291, 20869-20875 incorporated herein by reference in its entirety. Also US 20110244447 which suggests a different transient nucleotide binding approach is incorporated herein by reference in its entirety.

Native unlabeled nucleotides can be used when instead the polymerase is labeled. The concentration requirement of the polymerase is below 250 nM and hence TIRF illumination is sufficient to overcome background fluorescence. The polymerase can be labeled by a number of available means including those described above. In the case where the polymerase is labeled, the transient binding nucleotides are flowed in one by one (with washes preferably in between) and the binding kinetics or duration are observed, with the signal of longest sum duration called as the correct base. Machine learning algorithms can be applied to data obtained by implementing the sequencing approach model templates of known sequence in order to inform the base-calling algorithm.

Alternatively the nucleotide position the template adjacent to the 3' OH of the primer is interrogated by unincorporable nucleotides. There are a number of nucleotide analogs for which the covalent chemical linkage at incorporation is not productive. This includes the case when there is a modification on one of the phosphate groups of the nucleotide. In this embodiment the position adjacent to the 3'OH of the primer bound to the template is interrogated. The unicorporable nucleotides of various design specifications can be synthesized by Jena Biosciences. After the transient binding of the unincorporable nucleotides are recorded, a native nucleotide is added. This approach is preferably conducted in real-time where both the four native nucleotides and four differently labeled nucleotides are added together with the former at a much less (10-100 fold) concentration than the latter set. Without provision of further technical effects this approach can however suffer from a difficulty in calling homopolymers, without a signal indicating shift from one position to the next. For this reason the incorporable nucleotide used to shift to the next position can also be labeled and then the level is removed upon or after its incorporation.

Analysis and base calling is done using single molecule localization (e.g. ThunderSTORM) and adapted Swift software. In a second implementation of the transient nucleotide binding approach a single type of reversible terminator fluorescently labeled at the terminal phosphate is used and can be custom made by Jena Biosciences or Trilink. In some implementations the reversible terminator is fluorescently labeled with a FRET donor or photoactivator and the label on the transiently binding nucleotide is a FRET acceptor and/or is in a darkened state before it transiently binds the extension complex. After approximately 10,000 frames are collected for each wavelength, the termination can be reversed and the cycle for the next base addition, across the array of templates. The reversible terminator can be labeled on the base with Cy3B, Atto 542, Atto 488 or Alexa 488 as donor and the transiently binding nucleotide can be labeled with Atto 655 and three other acceptors).

Example transient nucleotide binding experiment:

1) Prepare flow cell: clean glass slide (VWR) with isopropanol, make a 0.5 mm channel by attaching two strips of double-sided tape (Scott) in parallel and separated by 0.5 cm to the slide and attaching a 18×18 mm coverslip on top.

2) Coat with Streptavidin: Flow in (by pipetting solution at the entrance of one end of channel and blotting with Kimwipe at the other end) 20 ul of BSA-Biotin (Sigma, USA) and incubatefor 2 minutes, wash with Buffer A+ and then add 20 ul of Streptavidin (Life Technologies, USA) and incubate for two minutes and then wash 1× with Buffer A+ and 1× with Buffer B+.

3) Arraying template on surface: Add 20 ul of 100 nM of 5' biotinylated self-priming hairpin template (5' Biotin TTT TTG TTT TTT TTT CTA GAG GAC TTA AGG CGC TTG CGC CTT AAG TC (SEQ ID NO:2) 2',3'-ddC 3') is purchased from IBA Lifesciences (Germany) which in this case is dideoxy terminated at the 3' end, to surface and incubate for 2 minutes and then wash 2× with Buffer B+. Add 1 in 2000 dilution of neat 1 mM YOYO-1 in Buffer B+ to visualize the locations of the template.

5) Attaching Fiducial Markers randomly on surface: Add 1 in 100 dilution in B+ of 100 nm size Tetraspeck beads and incubate for 5 minutes and wash 3× with B+

6) Add 3 uM of Atto 655 dUTP in a reaction mix containing Klenow fragment (NEB, USA) and 1 uM YOYO-1; optionally seal the ends of the channel e.g. with cow gum (done after initial imaging in this case). The reaction comprises: 10 ul NEB buffer 2; 1 ul (5 units) Klenow Fragment (3'-5' exo-); 3 ul (3 uM final) dUTP Atto655; (NEB) 1 ul of 100 uM YOYO-1; 84 ul H20. The reaction mix is pipetted and sucked into the flow cell and the reaction is allowed proceed in the flow cell at room temperature.

7) Imaging Transient Binding: Place the flow cell on a Nikon Ti-E microscope with the cover glass facing the 100×1.49 NA TIRF Objective lens and finding the focus by using the Perfect Focus mechanism of the microscope. Excite with 488 nM laser (IBeam Smart, Toptica, Germany) at close to full power (around 100 mW input into the input of a fiber optical scrambler (Laser Quantum, UK), ~10-20 mW at closely above the output of the objective). Set the TIRF angle low, at 1693 on the dial, set a further 1.5× magnification, set the EM gain on the Hammamatus back-thinned ImageEM to 170 and the exposure time to 400 ms. Project the image through an Optical Insights Quad View fitted with the following dichroics and emission filters:

T575 LPXR
T640 LPXR
T690 LPXR
ET550/20M
ET590/33M
ET670/30M
ET710/40M

Figure 23:
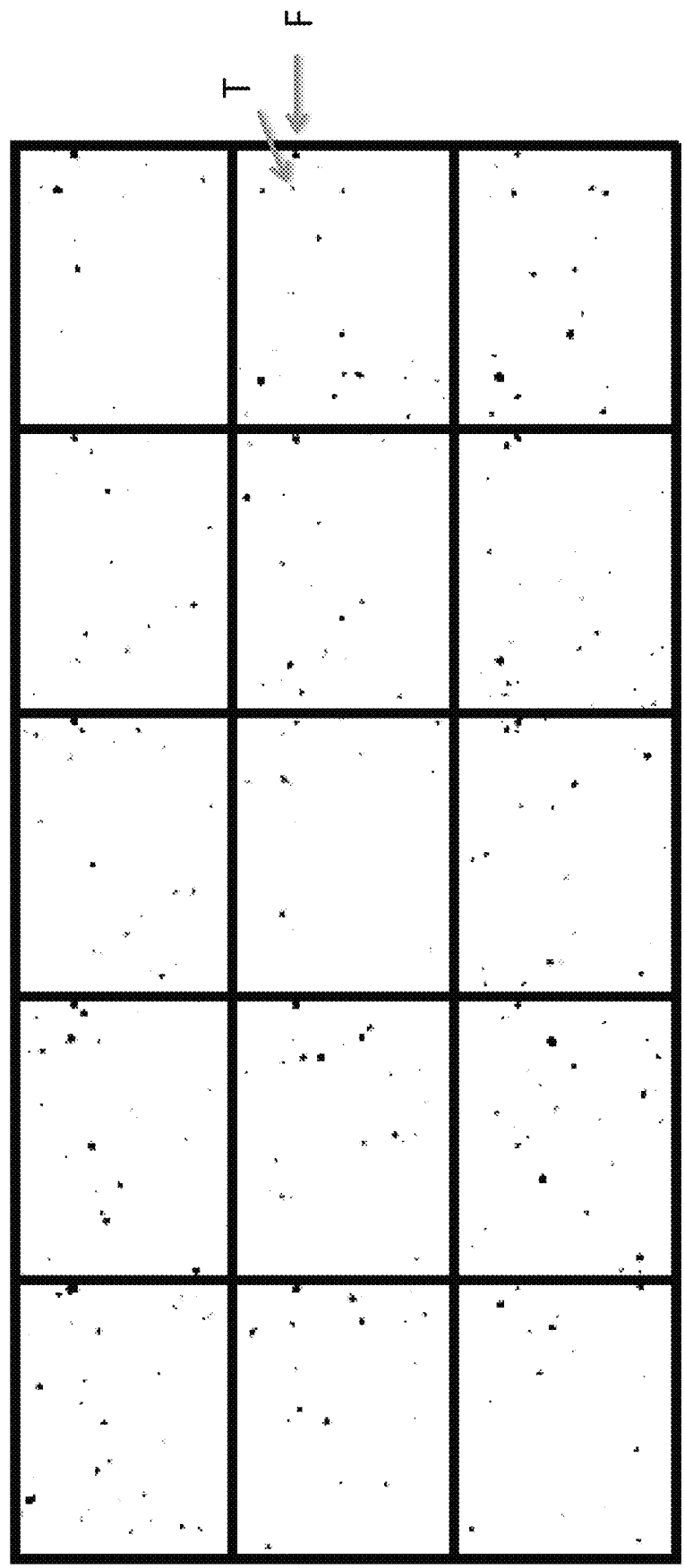
FIG. 23 Transiently binding nucleotide. 24 frames of 400 milliseconds each from a region on Hammamtsu ImageEM camera (0.11 uM/pixel) ordered left to right, top row to bottom row of Atto655 labelled dUTP binding to dideoxy terminated self-priming hairpin. F indicates a fiducial tetraspeck 100 nm bead and T indicates transient signal that is repeated again in the frame set after it has not been detected for a number of frames. The consecutive frames show the appearance and disappearance of signal due to transient binding of the nucleotides. The nucleotide binding is detected via FRET from YOYO-1 intercalant in the duplex part of the hairpin and the transiently associating Atto655-dUTP (3 uM) in the presence of 0.05 Units/ul of Klenow and 10 mM $MgCl_2$.

Use NIS-Elements software on Nikon Ti-E to take a movie of the transient binding events across the 4 split quadrants of the camera. The on-off signals can be seen in the ET710 and ET670 quadrants suggesting effective FRET is occurring by the YOYO-1 intercalant excited by the 488 nM laser and the transiently binding dUTP-Atto655. FIG. 23 shows a montage of 24 frames showing a fiducial tetraspeck marker and multiple occurrence of a transient signal. 8) Single Molecule Localization. The ET710 or ET670 quadrant is cropped from the stack of movie images and subjected to Thunderstorm to produce a super-resolution image.

This experimental demonstration of interrogation of a base by a transiently binding nucleotide is extended to complete sequencing by first incorporating a reversible terminator (e.g. from the above set from Jena Biosciencs) at a concentration of 5 uM onto the 3'OH of a primer bound to the template using Therminator™ III DNA polymerase (0.1 unit/ul) at 65 degrees C., then adding the transiently binding nucleotides and imaging (as described above) and then removing the solution containing the transiently binding nucleotides, reversing termination (by addition of 100 mM TCEP for 25 minutes at 65 degrees C.), washing in buffer and adding the reversible terminators again to shift to the next position in the sequence. Protocols described in Palla et al RSC Adv. 2014 Jan. 1; 4(90):49342-49346 and Ju et al *Proc Natl Acad Sci USA*. 2006 Dec. 26; 103(52): 19635-19640 are incorporated incorporated herein by reference in its entirety. The full cycle can be automated on an Illumina GAII Genome Analyzer. The cycle of incorporation of reversible terminators for A, C, G and T, transient binding and imaging of differently labelled base-labelled A, C, G, T/U nucleotides, reversal of termination is repeated multiple times (e.g. 10) to obtain data for the sequencing of an array of templates on the surface (it should be noted that optionally where the reaction is not carried out in Homogenous mode, washes can be included in between steps).

Beyond the sequencing of the self priming hairpin template, real-world samples such a templates prepared from plasma (e.g. using MagMAX™ Cell-Free DNA isolation Kit, ThermoFisher), which are polyA tailed at the 3' end can be hybridized to an array of biotinylated oligo(t) oligos, which are 5' immobilized via the biotin onto a streptavidin coated surface and have a free 3' OH end which is used to initiate sequencing by synthesis using the transient nucleotide binding approach described in this section or any of the other methods described in this invention specification.

Preparation of Populations of Polynucleotide Species

In all the sequencing methods of the invention, the intention usually is to provide an array of polynucleotides representing a sample In the case of an RNA sample this will include many species and there may be multiple copies of each species. In the case of genomic DNA, if it is from humans then there will be multiple fragments from the diploid genome; and if a single cell is examined there will be two copies of the genome.

The genomic DNA can be tailed with A nucleotide using terminal transferase, using a single nucleotide and a terminal transferase enzyme. The population of fragments can then be captured by a biotinylated oligo dT arrayed at between 10 and 300 pM depending on the density required. Similarly oligo dT is able to capture a polyA RNA or a tailed RNA.

Imaging Solutions

During imaging in non-homogeneous reactions and in homogeneous reactions, oxygen scavengers can be used to reduce photobleaching and dark states. Many formulations will be known to those familiar with the state of art. These typically include oxygen scavengers and can change depending on the nature of sequencing biochemistry being implemented. For example when the dye used is Cy5 the following solution can be used:

30% acetonitrile and scavenger buffer (100 mM HEPES, 67 mM NaCl, 25 mM MES, 12 mM Trolox, 5 mM DABCO, 80 mM glucose, 5 mM NaI, and 0.1 U/L glucose oxidase (USB), pH 7.0). In some cases reducing agents such as 2-mercaptoethanol and vitamin C can be added. Special formulations can be used with Qdots to promote blinking or to suppress it depending on sequencing approach.

Illuminating the nucleotide binding and/or nucleotide incorporation reactions with electromagnetic radiation can induce formation of reactive oxygen species from the fluorophore or other components in the reaction. The reactive oxygen species can cause photo-damage to the fluorophores, polymerases, or any other component of the binding or incorporation reactions. The nucleotide binding or nucleotide incorporation reactions can include compounds which are capable of reducing photo-damage, including: protocatechuate-3,4-dioxygenase, protocatechuic acid; 6-Hydroxy-2,5,7,8-tetramethylchroman-2-carboxylic Acid (TROLOX); or cyclooctatetraene (COT).

Other compounds for reducing photo-damage include: ascorbic acid, astazanthin, bilirubin, biliverdin, bixin, captopril, canthazanthin, carotene (alpha, beta, and gamma), cysteine, beta-dimethyl cysteine, N-acetyl cysteine, diazo-bicyclooctane (DABCO), dithiothreitol (DTT), ergothioneine, glucose oxidase/catalase (GO/Cat), glutathione, glutathione peroxidase, hydrazine (N2H4), hydroxylamine, lycopene, lutein, polyene dialdehydes, melatonin, methionine, mercaptopropionylglycine, 2-mercaptoethane sulfonate (MESNA), pyridoxinel and its derivatives, mercaptoethylamine (MEA), 3-mercaptoethanol (BME), n-propyl gallate, p-phenylenediamene (PPD), hydroquinone, sodium azide (NaN3), sodium sulfite (Na2SO3), superoxide dismutase, tocopherols, α-tocopheryl succinate and its analogs, and zeaxanthin.

Imaging and Image Processing

Imaging can be done without moving the sample stage (holding the flow cell) in relation to the camera. This can be done during real-time, continuous sequencing or optionally when superresolution data is taken. Cameras described elsewhere in this invention can be used. Ideally the camera has low electron noise, such as below 1 or 2 electrons per pixels. Cameras containing Sony IMX253 sensor which comprises 12 million 3.5 micron pixels and low electron noise can be used. This sensor is coupled to a 10 GigE interface fro fast data transfer (allowing 80 frames per second in the HR1200 by Emergent Vision Technologies (Canada). When coupled with a 20× objective this sensor is capable of imaging ~2 Megabase length of stretched DNA in one axis of the sensor. Alternatively to cover a large area, when the sequencing involves a pause or termination step, the sample stage is translated in relation to the camera. This allows a larger array of molecules to be covered. A translation stage with linear encoders enable precise alignment from cycle to cycle and drift correction for example fiducial markers (e.g. Tetraspeck beads, NanoDiamond (Adamas nanotechnologies, Rayleigh, N.C., USA) can be used to assist alignment of images. In some embodiments a line scanner or TDI imaging is used which involves continuous translation of the stage in synchrony with camera readout. TDI sensors are available for Hamamatsu and other vendors.

Image processing can be done using and adapted SWIFT (Whiteford et al) and can use tools in Fiji including plug-ins such as ThunderSTORM. Optionally DNA origami drift markers (~100 pM) can be added to the experiment. As an alternative to origami 100 nm gold nanoparticles, (Sigma Aldrich; 10 nM in buffer C, added before imaging), 100 nM Tetrasppeck beads (Thermofisher) can be used as drift and alignment markers. The drift correction involves tracking the position of each marker through the duration of each movie, averaging the trajectory of all detected markers to globally correct drift in the image. Also Fiji/Thunder-STORM as well as MatLab have inherent drift correction algorithms which are reasonably effective and do not require fiduciary markers but rather correct drift by autocorrelation. The Nikon Ti microscopes have Perfect Focus and Olympus have Z drift compensation module (IX3-ZDC2). Also a a low tech method for avoiding drift is to robustly attach the sample stage to the objective. Also if thermal environment is well controlled, drift can be made negligible and/or stabilizes after a few minutes. Off the shelf cameras such as Photometrics Prime 95B include particle tracking capability that can be used to keep the fiducial markers in focus.

Compiling Sequence Reads Form Single Molecule Data

Once the desired number of cycles is completed, the image stack data or the single molecule localization stack data (i.e., positions of the raw signals or those produced after running a single molecule localization algorithm across the array or each color) are aligned to produce the individual sequence reads.

The invention claimed is:

1. A method for template-directed sequencing-by-synthesis of an array of target polynucleotides, the method comprising:
   (a) providing an array of target polynucleotides in a fluidic vessel;
   (b) contacting the array of polynucleotides with a solution comprising (i) polymerization complex and (ii) reversibly terminating and differently labeled A,C,G, and T/U nucleotides;
   (c) incorporating one of the differently labeled nucleotides, using the polymerization complex, into a chain complementary to at least one of the array of polynucleotides;
   (d) binding imaging tags to the differently labeled nucleotides of step (c);
   (e) imaging by single molecule localization and/or stochastic optical reconstruction and storing the identity and position of the imaging tags of step (d);
   (f) reversing termination (b)-(e);
   (g) repeating steps (b)-(e) and assembling a sequence for each of the array of target polynucleotides from the stored identity and position of the imaging tags, optionally as a homogeneous or one pot reaction.

2. The method of claim 1, wherein binding the tags comprises multiple, stochastic on/off binding events.

3. The method of claim 1, wherein the target polynucleotide is disposed on a surface.

4. The method of claim 1, wherein the target polynucleotide is stretched and/or elongated.

5. The method of claim 4, further comprising seeding the incorporation at multiple locations on the stretched and/or elongated target polynucleotide.

6. The method of claim 1, wherein the incorporation comprises extension from a nick, extension from an oligonucleotide, use of a DNA polymerase not requiring a primer, or transcription from a promoter.

7. The method of claim 1, wherein an intercalating dye or a fluorescent/luminescent entity is provided as a RET donor and the label on the nucleotide is a RET acceptor.

8. The method of claim 1, further comprising sequencing two or more polynucleotides simultaneously.

9. The method of claim 1, wherein the labeled nucleotide comprises a fluorescent organic dye or fluorescent nanoparticle.

10. The method of claim 1, wherein the labeled nucleotide comprises a quencher.

11. The method of claim 1, wherein the label comprises a first partner of a binding pair.

12. The method of claim 11, wherein the second partner of a binding pair comprises a fluorescently labeled transiently binding oligonucleotide.

13. The method of claim 1, wherein the label is superresolved.

14. The method of claim 1, wherein the imaging or illuminating step further comprises providing electromagnetic radiation via an evanescent wave.

15. The method of claim 1, wherein the imaging or illuminating step further comprises enhancing the fluorescence by proximity related effects with metals.

16. The method of claim 1, wherein the imaging or illuminating step further comprises controlling the attraction and repulsion of the labeled nucleotides using an electric field.

17. The method of claim 1, wherein assembling the sequence comprises single molecule localization, stochastic optical reconstruction microscopy (STORM), points accumulation for imaging in nanoscale topography (PAINT), or stimulated emission depletion (STED).

* * * * *

```
                         SEQUENCE LISTING

<160> NUMBER OF SEQ ID NOS: 33

<210> SEQ ID NO 1
    <211> LENGTH: 11
    <212> TYPE: PRT
    <213> ORGANISM: Artificial Sequence
    <220> FEATURE:
    <223> OTHER INFORMATION: Synthetic

<400> SEQUENCE: 1

Thr Thr Ala Thr Ala Cys Ala Thr Cys Thr Ala
    1               5                   10

<210> SEQ ID NO 2
    <211> LENGTH: 94
    <212> TYPE: PRT
    <213> ORGANISM: Artificial Sequence
    <220> FEATURE:
    <223> OTHER INFORMATION: Synthetic

<400> SEQUENCE: 2

Thr Thr Thr Thr Thr Gly Thr Thr Thr Thr Thr Thr Thr Thr Cys
    1               5                   10                  15

Thr Ala Gly Ala Gly Gly Ala Cys Thr Ala Ala Gly Gly Cys Gly
                20                  25                  30

Cys Thr Thr Gly Cys Gly Cys Cys Thr Thr Ala Ala Gly Thr Cys Thr
                35                  40                  45

Thr Thr Thr Thr Gly Thr Thr Thr Thr Thr Thr Thr Thr Cys Thr
        50                  55                  60

Ala Gly Ala Gly Gly Ala Cys Thr Thr Ala Ala Gly Gly Cys Gly Cys
    65                  70                  75                  80

Thr Thr Gly Cys Gly Cys Cys Thr Thr Ala Ala Gly Thr Cys
                    85                  90

<210> SEQ ID NO 3
    <211> LENGTH: 9
    <212> TYPE: PRT
    <213> ORGANISM: Artificial Sequence
    <220> FEATURE:
```

<223> OTHER INFORMATION: Synthetic

<400> SEQUENCE: 3

Thr Thr Ala Cys Thr Thr Thr Cys Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Ala Thr Cys Cys Gly Gly Gly Gly Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Thr Ala Cys Cys Ala Ala Gly Gly Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gly Gly Ala Ala Ala Gly Thr Ala Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Gly Cys Cys Ala Ala Gly Gly Ala Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Cys Gly Gly Thr Thr Cys Cys Thr Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Thr Thr Ala Thr Ala Cys Ala Thr Cys Thr Ala
1               5                   10

<210> SEQ ID NO 10
<211> LENGTH: 48
<212> TYPE: PRT
<213> ORGANISM: Artificial Sequence
<220> FEATURE:
<223> OTHER INFORMATION: Synthetic

<400> SEQUENCE: 10

Thr Thr Thr Thr Thr Gly Thr Thr Thr Thr Thr Thr Thr Thr Thr Cys
1               5                   10                  15

Gly Thr Ala Asn Cys Gly Ala Cys Thr Thr Ala Ala Gly Gly Cys Gly
            20                  25                  30

Cys Thr Thr Gly Cys Gly Cys Cys Thr Thr Ala Ala Gly Thr Cys Gly
        35                  40                  45

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Thr Thr Ala Thr Cys Thr Ala Cys Ala Thr Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Thr Thr Thr Cys Thr Thr Cys Ala Thr Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Thr Thr Ala Thr Gly Ala Ala Thr Cys Thr Ala
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Thr Thr Thr Thr Ala Gly Gly Thr Ala Ala Ala
1               5                   10

<210> SEQ ID NO 15

```
<211> LENGTH: 11
<212> TYPE: PRT
<213> ORGANISM: Artificial Sequence
<220> FEATURE:
<223> OTHER INFORMATION: Synthetic

<400> SEQUENCE: 15

Thr Thr Ala Ala Thr Thr Gly Ala Gly Thr Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Thr Thr Ala Ala Thr Thr Ala Gly Gly Ala Thr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic

<400> SEQUENCE: 17

Thr Thr Ala Thr Ala Ala Thr Gly Gly Ala Thr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Thr Thr Thr Ala Ala Thr Ala Ala Gly Gly Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic

<400> SEQUENCE: 19

Thr Thr Ala Thr Ala Gly Ala Gly Ala Ala Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Thr Thr Thr Thr Gly Ala Thr Gly Ala Thr Ala
1               5                   10

<210> SEQ ID NO 21
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 21

Thr Thr Ala Thr Ala Gly Thr Gly Ala Thr Thr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Cys Thr Ala Gly Ala Thr Gly Thr Ala Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Thr Ala Thr Gly Thr Ala Gly Ala Thr Cys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Gly Thr Ala Ala Thr Gly Ala Ala Gly Ala
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Gly Thr Ala Gly Ala Thr Thr Cys Ala Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic

<400> SEQUENCE: 26

Cys Thr Thr Thr Ala Cys Cys Thr Ala Ala
1               5                   10

<210> SEQ ID NO 27
<211> LENGTH: 10
<212> TYPE: PRT
```

<213> ORGANISM: Artificial Sequence
<220> FEATURE:
<223> OTHER INFORMATION: Synthetic

<400> SEQUENCE: 27

Gly Thr Ala Cys Thr Cys Ala Ala Thr Thr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Cys Ala Thr Cys Cys Thr Ala Ala Thr Thr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Gly Ala Thr Cys Cys Ala Thr Thr Ala Thr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic

<400> SEQUENCE: 30

Cys Ala Cys Cys Thr Thr Ala Thr Thr Ala
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Cys Cys Thr Thr Cys Thr Cys Thr Ala Thr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gly Thr Ala Thr Cys Ala Thr Cys Ala Ala
1               5                   10

<210> SEQ ID NO 33
<211> LENGTH: 10
<212> TYPE: PRT
<213> ORGANISM: Artificial Sequence

```
<220> FEATURE:
<223> OTHER INFORMATION: Synthetic

<400> SEQUENCE: 33

Gly Ala Ala Thr Cys Ala Cys Thr Ala Thr
1               5                   10
```